US009005632B2

(12) United States Patent
Stinchcomb et al.

(10) Patent No.: US 9,005,632 B2
(45) Date of Patent: *Apr. 14, 2015

(54) COMPOSITIONS, METHODS AND USES FOR POXVIRUS ELEMENTS IN VACCINE CONSTRUCTS AGAINST INFLUENZA VIRUS SUBTYPES OR STRAINS

(75) Inventors: Dan T. Stinchcomb, Fort Collins, CO (US); Jorge E. Osorio, Mount Horeb, WI (US); Timothy D. Powell, Fort Collins, CO (US); Jeremy C. Jones, Memphis, TN (US); Joseph N. Brewoo, Madison, WI (US)

(73) Assignee: Takeda Vaccines, Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/555,026

(22) Filed: Jul. 20, 2012

(65) Prior Publication Data

US 2013/0209513 A1  Aug. 15, 2013

Related U.S. Application Data

(63) Continuation-in-part of application No. 13/510,601, filed as application No. PCT/US2010/057682 on Nov. 22, 2010.

(60) Provisional application No. 61/263,327, filed on Nov. 20, 2009.

(51) Int. Cl.
| | |
|---|---|
| A61K 49/00 | (2006.01) |
| A61K 39/38 | (2006.01) |
| A61K 39/295 | (2006.01) |
| A61K 39/145 | (2006.01) |
| A61K 39/245 | (2006.01) |
| C12Q 1/70 | (2006.01) |
| C12N 15/863 | (2006.01) |
| A61K 39/12 | (2006.01) |
| C07K 14/005 | (2006.01) |
| A61K 39/00 | (2006.01) |

(52) U.S. Cl.
CPC .............. *C12N 15/863* (2013.01); *A61K 39/12* (2013.01); *A61K 2039/5256* (2013.01); *C12N 2760/16034* (2013.01); *A61K 39/00* (2013.01); *A61K 39/145* (2013.01); *C12N 2760/16134* (2013.01); *C07K 14/005* (2013.01); *C07K 2319/02* (2013.01); *C12N 2710/24143* (2013.01); *C12N 2760/16122* (2013.01)

(58) Field of Classification Search
None
See application file for complete search history.

(56) References Cited

U.S. PATENT DOCUMENTS

2007/0231348 A1* 10/2007 Kawaoka et al. .......... 424/209.1

FOREIGN PATENT DOCUMENTS

| WO | WO 97/02355 A1 | 1/1997 |
|---|---|---|
| WO | WO 01/68820 A1 | 9/2001 |
| WO | WO 2008/061939 A1 | 5/2008 |
| WO | 2011063359 A1 | 5/2011 |

OTHER PUBLICATIONS

Patel et al., The N-terminal 22 amino acids encoded by the gene specifying the major secreted protein of vaccinia virus, strain Lister, can function as a signal sequence to direct the export of a foreign protein, 1992, Virus Research, vol. 26, No. 3, abstract.*
Gaeda et al., Movements of vaccinia virus intracellular enveloped virions with GFP tagged to the F13L envelope protein, 2001, Journal of General Virology, vol. 82, pp. 2747-2760.*
Kreijtz et al., MVA-Based H5N1 Vaccine Affords Cross-Clade Protection in Mice against Influenza A/H5N1 Viruses at Low Doses and after Single Immunization, 2009, PLoS One, vol. 4, No. 11, pp. 1-8.*
Sutter et al., A recombinant vector derived from the host range-restricted and highly attenuated MVA strain of vaccinia virus stimulates protective immunity in mice to influenza virus, 1994, Vaccine, vol. 12, No. 11, pp. 1032-1040.*
GenBank Accession # P21044, RecName: Full=Protein C13 [Vaccinia virus Copenhagen], Apr. 2013.*
Breathnach et al., Use of recombinant modified vaccinia Ankara viral vectors for equine influenza vaccination, 2004, Veterinary Immunology and Immunopathology, vol. 98, pp. 127-136.*
Brewoo Joseph H et al: "Efficacy and safety of a modified vaccinia Ankara (MVA) vectored plague vaccine in mice", Vaccine vol. 28, No. 36, Aug. 2010, pp. 5891-5899, XPOO2718191, ISSN: 0264-410X.
Brewoo Joseph H et al: "Cross-protective immunity against multiple influenza virus subtypes by a novel modified vaccinia Ankara (MVA) vectored vaccine in mice", Vaccine vol. 31 No. 14, Apr. 2013 pp. 1848-1855, XPOO2718190.
International Search Report and Written Opinion for PCT/US2013/041353 dated Jan. 14, 2014, 14 pages.
Patel et al., The N-terminal 22 amino acids encoded by the gene specifying the major secreted protein of vaccinia virus, strain Lister, can function as a signal sequence to direct the export of a foreign protein, 1992, Virus Research, vol. 26 No. 3, pp. 197-212.
Blanchard et al., Modified *vaccinia virus*Ankara undergoes limited replication in human cells and lacks several immunomodulatory proteins: implications for use as a human vaccine. Journal of General Virology, 1998, vol. 79, pp. 1159-1167.

* cited by examiner

*Primary Examiner* — Benjamin P Blumel
(74) *Attorney, Agent, or Firm* — Faegre Baker Daniels LLP

(57) ABSTRACT

Embodiments of the present invention generally disclose methods, compositions and uses for generating and expressing poxvirus constructs. In some embodiments, constructs may contain an influenza virus gene segment. In certain embodiments, methods generally relate to making and using compositions of constructs including, but not limited to, poxvirus vaccine compositions having two or more influenza gene segments. In other embodiments, vaccine compositions are reported of use in a subject.

18 Claims, 33 Drawing Sheets

Fig. 1B

Lung Titers (4 dpi)

Fig. 3

Survival (ID Vaccinations)

Weights (ID Vaccinations)

- MVA/HA Prime (ID)
- MVA/HA Prime/Boost (ID)
- MVA/HA Prime + MVA/Flagel (
- MVA/GFP
- MVA/GFP + MVA/Flagellin
- Form.Inact. VN/1203

- Sacrificed 3 mice from each group D4 p.i
- Homogenized lungs – titered on MDCKs
- Log virus titer is represented

Fig. 10C

Table 1: MVA influenza transfer vectors and MVA constructs

| Transfer Vector designation | Se/l IRES | IRES | Secretory signal tP78484A | C13L | B8R | Flu, HA | Flu, HA native | flu, HA1 | flu, Ha1 nat | Flu, NA | Flu, NP | Flu, NA trunc | Recombinant construct |
|---|---|---|---|---|---|---|---|---|---|---|---|---|---|
| pI52 | X |   |   |   |   |   | X |   |   |   |   |   | MVA/52-1B1A1 |
| pI53 | X | X | X |   |   | X |   |   |   |   |   |   | MVA/53-3A1A |
| pI54 | X |   | X |   |   | X |   |   |   |   |   |   | MVA/54-1A1A |
| pI69 | X |   |   | X |   | X |   |   |   |   |   |   | MVA/69-1A1A |
| pI70 | X |   |   |   | X | X |   |   |   |   |   |   | MVA/70-1A1A |
| pI71 | X | X |   | X |   | X |   |   |   |   |   |   | MVA/71-1A1A |
| pI72 | X | X |   |   | X | X |   |   |   |   |   |   | MVA/72-1A1A |
| pI73 | X |   |   |   |   |   |   |   | X |   |   |   | MVA/73-1A1A |
| pI74 | X |   | X |   |   |   |   | X |   |   |   |   | MVA/74-1A1A |
| pI75 | X |   |   | X |   |   |   | X |   |   |   |   | MVA/75-1A1A |
| pI76 | X |   |   |   | X |   |   | X |   |   |   |   | MVA/76-1A1A |
| pI77 | X | X | X |   |   |   |   | X |   |   |   |   | MVA/77-1A1A |
| pI78 | X | X |   | X |   |   |   | X |   |   |   |   | MVA/78-1A1A |
| pI79 | X | X |   |   | X |   |   | X |   |   |   |   | MVA/79-1A1A |
| pI80 | X |   |   |   |   |   |   |   |   |   |   | X | MVA/80-2A1A |
| pI81 | X |   |   |   |   |   |   |   |   | X |   |   | MVA/81-1A1A |
| pI83 | X |   | X |   |   |   |   |   |   | X |   |   | MVA/83-1A1A |
| pI84 | X |   |   | X |   |   |   |   |   | X |   |   | MVA/84-1A1A |
| pI85 | X |   |   |   | X |   |   |   |   | X |   |   | MVA/85-1A1A |
| pI86 | X | X | X |   |   |   |   |   |   | X |   |   | MVA/86-1A1A |
| pI87 | X | X |   | X |   |   |   |   |   | X |   |   | MVA/87-1A1A |
| pI88 | X | X |   |   | X |   |   |   |   | X |   |   | MVA/88-1A1A |
| pI89 | X |   | X |   |   |   |   |   |   |   | X |   | MVA/89-2A1A |
| pI90 | X |   |   | X |   |   |   |   |   |   | X |   | MVA/90-1A1A |
| pI91 | X |   |   |   | X |   |   |   |   |   | X |   | MVA/91-1A1A |
| pI92 | X | X | X |   |   |   |   |   |   |   | X |   | MVA/92-1A1A |
| pI93 | X | X |   | X |   |   |   |   |   |   | X |   | MVA/93-1A1A |
| pI94 | X | X |   |   | X |   |   |   |   |   | X |   | MVA/84-1A1A |
| pI95 | X |   |   | X |   |   |   |   |   |   |   | X | MVA/95-1A1A |
| pI96 | X | X |   | X |   |   |   |   |   |   |   | X | MVA/96-1A1A |

Fig. 11A

[Graph: MVA/IRES/C13L/HA Native — % Weight Change vs dpi (0–12), with curves for 5x10^7, 5x10^6, 5x10^5]

Fig. 11B

[Graph: MVA-GFP — % Weight Change vs dpi (0–12)]

Fig. 12A

*MVA/IRES/tpa/HAt* — % Weight Change vs dpi; curves for 5x10^7, 5x10^6, 5x10^5.

Fig. 12B

*MVA/IRES/C13L/HAt* — % Weight Change vs dpi; curves for 5x10^7, 5x10^6, 5x10^5.

Fig. 15A

[Graph: MVA/IRES/tpa/HAt — % Survival vs dpi (0–12), series: 5x10^7, 5x10^6, 5x10^5]

Fig. 15B

[Graph: MVA/IRES/C13L/HAt — % Survival vs dpi (0–12), Series1, Series2, Series3]

Fig. 17A

MVA/IRES/C13L/HA Native

Fig. 17B

MVA/IRES/tPA/HAt

Fig. 26A
Fig. 26B
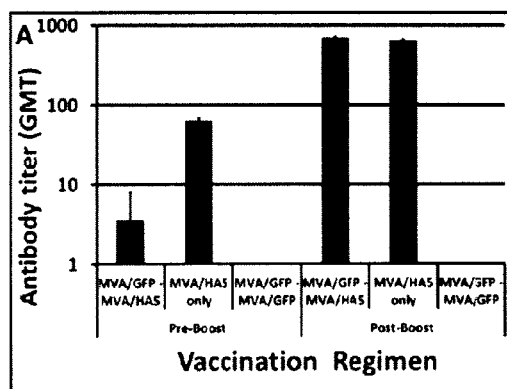
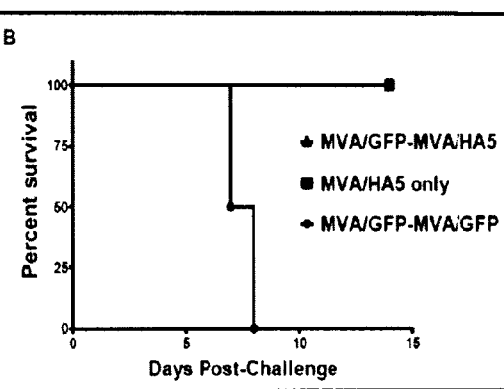

Fig. 27

SEQUENCE LISTING

<160> NUMBER OF SEQ ID NOS: 20

<210> SEQ ID NO 1
<211> LENGTH: 18
<212> TYPE: PRT
<213> ORGANISM: Artificial Sequence
<220> FEATURE:
<223> OTHER INFORMATION: vaccinia virus secretory signal

<400> SEQUENCE: 1

Met Met Ile Tyr Gly Leu Ile Ala Cys Leu Ile Phe Val Thr Ser Ser
1               5                   10                  15

Ile Ala

<210> SEQ ID NO 2
<211> LENGTH: 17
<212> TYPE: PRT
<213> ORGANISM: Artificial Sequence
<220> FEATURE:
<223> OTHER INFORMATION: vaccinia virus secretory signal

<400> SEQUENCE: 2

Met Arg Tyr Ile Ile Ile Leu Ala Val Leu Phe Ile Asn Ser Ile His
1               5                   10                  15

Ala

<210> SEQ ID NO 3
<211> LENGTH: 32
<212> TYPE: DNA
<213> ORGANISM: Artificial Sequence
<220> FEATURE:
<223> OTHER INFORMATION: primer

<400> SEQUENCE: 3
tcgtcccggg ttattttcca ccatattgcc gt 32

<210> SEQ ID NO 4
<211> LENGTH: 94
<212> TYPE: DNA
<213> ORGANISM: Artificial Sequence
<220> FEATURE:
<223> OTHER INFORMATION: primer

<400> SEQUENCE: 4
tcgtgccggc tggactagcg atggatgaag tcacgaatat aagacacgct attaatccgt 60
atatcatcat attatcatcg tgtttttcaa agga 94

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
tcgtcccggg ttattttcca ccatattgcc gt 32

<210> SEQ ID NO 6
<211> LENGTH: 88
<212> TYPE: DNA
<213> ORGANISM: Artificial Sequence
<220> FEATURE:
<223> OTHER INFORMATION: primer

<400> SEQUENCE: 6

-continued

```
tcgtgccggc tttagcgtgt atactattaa tgaacaaaac tgcgagaatt ataatatatc    60
tcatattatc atcgtgtttt tcaaagga                                      88

<210> SEQ ID NO 7
<211> LENGTH: 72
<212> TYPE: DNA
<213> ORGANISM: Artificial Sequence
<220> FEATURE:
<223> OTHER INFORMATION: primer

<400> SEQUENCE: 7
ccgggatgat gatatacgga ttaatagcgt gtcttatatt cgtgacttca tccatcgcta    60
gtccagccgg cg                                                       72

<210> SEQ ID NO 8
<211> LENGTH: 72
<212> TYPE: DNA
<213> ORGANISM: Artificial Sequence
<220> FEATURE:
<223> OTHER INFORMATION: primer

<400> SEQUENCE: 8
ctagcgccgg ctggactagc gatggatgaa gtcacgaata taagacacgc tattaatccg    60
tatatcatca tc                                                       72

<210> SEQ ID NO 9
<211> LENGTH: 66
<212> TYPE: DNA
<213> ORGANISM: Artificial Sequence
<220> FEATURE:
<223> OTHER INFORMATION: primer

<400> SEQUENCE: 9
ccgggatgag atatattata attctcgcag ttttgttcat taatagtata cacgctaaag    60
ccggcg                                                              66

<210> SEQ ID NO 10
<211> LENGTH: 66
<212> TYPE: DNA
<213> ORGANISM: Artificial Sequence
<220> FEATURE:
<223> OTHER INFORMATION: primer

<400> SEQUENCE: 10
ctagcgccgg ctttagcgtg tatactatta atgaacaaaa ctgcgagaat tataatatat    60
ctcatc                                                              66

<210> SEQ ID NO 11
<211> LENGTH: 82
<212> TYPE: DNA
<213> ORGANISM: Artificial Sequence
<220> FEATURE:
<223> OTHER INFORMATION: primer sequence

<400> SEQUENCE: 11
tctccccggg atggagaaaa tagtgcttct ttttgcaata gtcagtcttg ttaaaagtga    60
tcagatttgc attggttacc at                                            82

<210> SEQ ID NO 12
<211> LENGTH: 31
<212> TYPE: DNA
```

<213> ORGANISM: Artificial Sequence
<220> FEATURE:
<223> OTHER INFORMATION: primer sequence

<400> SEQUENCE: 12
ggcggatcct taaatgcaaa ttctgcattg t                                31

<210> SEQ ID NO 13
<211> LENGTH: 82
<212> TYPE: DNA
<213> ORGANISM: Artificial Sequence
<220> FEATURE:
<223> OTHER INFORMATION: primer sequence

<400> SEQUENCE: 13
gtgacccggg atgaaggcca tcctggtcgt gctgctgtac accttcgcca ccgccaacgc    60
cgacacactg tgtatcgggt at                                            82

<210> SEQ ID NO 14
<211> LENGTH: 23
<212> TYPE: DNA
<213> ORGANISM: Artificial Sequence
<220> FEATURE:
<223> OTHER INFORMATION: primer sequence

<400> SEQUENCE: 14
gatccgctag ctcagataca gat                                           23

<210> SEQ ID NO 15
<211> LENGTH: 28
<212> TYPE: DNA
<213> ORGANISM: Artificial Sequence
<220> FEATURE:
<223> OTHER INFORMATION: primer sequence

<400> SEQUENCE: 15
gtgagccggc gcgtctcaag gcaccaaa                                      28

<210> SEQ ID NO 16
<211> LENGTH: 34
<212> TYPE: DNA
<213> ORGANISM: Artificial Sequence
<220> FEATURE:
<223> OTHER INFORMATION: primer sequence

<400> SEQUENCE: 16
gcgaattctt aattgtcata ctcctctgca ttgt                               34

<210> SEQ ID NO 17
<211> LENGTH: 72
<212> TYPE: DNA
<213> ORGANISM: Artificial Sequence
<220> FEATURE:
<223> OTHER INFORMATION: primer sequence

<400> SEQUENCE: 17
ccgggatgat gatatacgga ttaatagcgt gtcttatatt cgtgacttca tccatcgcta    60
gtccagccgg cg                                                       72

<210> SEQ ID NO 18
<211> LENGTH: 72
<212> TYPE: DNA
<213> ORGANISM: Artificial Sequence
<220> FEATURE:
<223> OTHER INFORMATION: primer sequence

<400> SEQUENCE: 18

```
ctagcgccgg ctggactagc gatggatgaa gtcacgaata taagacacgc tattaatccg      60
tatatcatca tc                                                          72
```

<210> SEQ ID NO 19
<211> LENGTH: 8385
<212> TYPE: DNA
<213> ORGANISM: Artificial Sequence
<220> FEATURE:
<223> OTHER INFORMATION: MVA construct

<400> SEQUENCE: 19

```
gaattaattc gttggtggtc gccatggatg gtgttattgt atactgtcta aacgcgttag      60
taaaacatgg cgaggaaata aatcatataa aaaatgattt catgattaaa ccatgttgtg     120
aaaaagtcaa gaacgttcac attggcggac aatctaaaaa caatacagtg attgcagatt     180
tgccatatat ggataatgcg gtatccgatg tatgcaattc actgtataaa agaatgtat      240 caagaatatc cagatttgct aatttgataa agatagatga cgatgacaag actcctactg     300
gtgtatataa ttatttttaaa cctaaagatg ccattcctgt tattatatcc ataggaaagg    360
atagagatgt ttgtgaacta ttaatctcat ctgataaagc gtgtgcgtgt atagagttaa     420
attcatataa agtagccatt cttcccatgg atgtttcctt ttttaccaaa ggaaatgcat     480
cattgattat tctcctgttt gatttctcta tcgatgcggc acctctctta agaagtgtaa     540
ccgataataa tgttattata tctagacacc agcgtctaca tgacgagctt ccgagttcca    600
attaattggt tcaagtttta cataagtata agtccgact attgttctat attatatatg     660
gttgttgatg gatctgtgat gcatgcaata gctgataata gaacttacgc aaatattagc     720
aaaaatatat tagacaatac tacaattaac gatgagtgta gatgctgtta ttttgaacca    780
cagattagga ttcttgatag agatgagatg ctcaatggat catcgtgtga tatgaacaga    840
cattgtatta tgatgaattt acctgatgta ggcgaatttg gatctagtat gttggggaaa    900
tatgaacctg acatgattaa gattgctctt tcggtggctg ggtaccttgc ggccgcttac    960
ttgtacagct cgtgcatgcc gagagtgatc ccggcggcgg tcacgaactc cagcaggacc   1020
atgtgatcgc gcttctcgtt ggggtctttg ctcagggcgg actgggtgct caggtagtgg   1080
ttgtcgggca gcagcacggg gccgtcgccg atggggtgt tctgctggta gtggtcggcg    1140
agctgcacgc tgccgtcctc gatgttgtgg cggatcttga agttcacctt gatgccgttc   1200
ttctgcttgt cggccatgat atagacgttg tggctgttgt agttgtactc cagcttgtgc   1260
cccaggatgt tgccgtcctc cttgaagtcg atgcccttca gctcgatgcg gttcaccagg   1320
gtgtcgccct cgaacttcac ctcggcgcgg gtcttgtagt tgccgtcgtc cttgaagaag   1380
atggtgcgct cctggacgta gccttcgggc atggcggact tgaagaagtc gtgctgcttc   1440
atgtggtcgg ggtagcggct gaagcactgc acgccgtagg tcagggtggt cacgagggtg   1500
ggccagggca cgggcagctt gccggtggtg cagatgaact tcagggtcag cttgccgtag   1560
gtggcatcgc cctcgccctc gccggacacg ctgaacttgt ggccgtttac gtcgccgtcc   1620
agctcgacca ggatgggcac cacccggtg aacagctcct cgcccttgct caccattat     1680 agcatagaaa aaacaaaat gaaaggcgcg cctggtaccg caataccaac caggaagaca   1740
cgaacattta ctgttctgtg ttccggtaca gaaaacaat tgataattct taattgtcat    1800
actcctctgc attgtctccg aagaaataag atccttcatt attcatgtca aggaaggca    1860
```

-continued

```
cgatcgggtt cgttgccttt tcgtccgaga gctcgaagac tccccgcccc tggaatgaca  1920
catcttctgg tctggcactt tccatcattc ttatgatttc agtcctcatg tcagacgttc  1980
tgccctcagt atttcctgta aatgctgcca taatggtcgc tctttcaaag ggaaggtttc  2040
tctggaccga gaaagtgggc tgaacgctga tctgtcctgc agatgccctc tgctggttgg  2100
tgtttcctcc gcttctggtt cttatagccc aatatctgct tctcagttca agagtgttgg  2160
agtccattgc ctccatgttc tcatttgaag caatttgaac ccctctggtg gatagctgtc  2220
ctcttgggac cactcttgtc cctctgatga aacttgagac tctaaggtcc tcaaatgctg  2280
cagagtggca tgccatccac actaattgac tcttatgtgc tggattctca tttggtctaa  2340
tgagactaaa gacctggctg ttttgaagca ggcggaaagg atctattcca accagagagt  2400
acccttctct ctcaaagtca tatccactgg ccactgcaag tccgtacaca caagcaggca  2460
agcaggactt atgggccact gatcctctca ggatgagtgc agaccgtgcc agaaaaatga  2520
gatcttcaat ttcagcattc ccaggatttc tgctctctcg cacttgatcc atcattgctc  2580
tttgtgctgc tgtttggaat ttccctttga ggatgttgca cattctctca tatgcaatcc  2640
ttgttcttct tccattttcg cctctccaga aattccggtc gttgatccct cgttttatca  2700
tccgaatcag ctccatcacc attgtcccta ccccctttac tgctgcaccg gcagctccag  2760
atctcctcgg gagagttgac ccttgcatca gagagcacat ccttgggtcc attccagtac  2820
gcacgagagc tctcgttctc tgatatgtgg catcatttag attggaatgc catatcatca  2880
ggtgggtaag accagcagtt gcgtcctctc cattgttcgc ttgacgccaa atcctcctga  2940
tctcctcttt gtcgtacaga attagctctc tcacccattt cccgtctctc ctccgataaa  3000
ttggacctcc agtcttcttc gggtcctttc ccgcactggg gtgttcttcc aggtatctgt  3060
tccttctttc atcaaatgca gagagtacca ttctctctat tgttatgctg ttctggatca  3120
gcctcccttc atagtcactg agtttgagtt ctgtgcacat ctgtatgtag aacctcccaa  3180
tgccactaac cattcttcca acagatgccc tgatctcagt agcattctgg cgttccccac  3240
cagtttccat ctgttcataa gatcgtttgg tgccttgaga cgcgccggct ggactagcga  3300
tggatgaagt cacgaatata agacacgcta ttaatccgta tatcatcatc ccggtcttat  3360
ttatattcca aaaaaaaaa ataaaatttc aattttccg gaaaaattga aattttattt  3420
ttttttttg gaatataaat aagcccggga tgaaggccat cctggtcgtg ctgctgtaca  3480
ccttcgccac cgccaacgcc gacacactgt gtatcgggta tcacgcaaac aatagtactg  3540
ataccgtcga cacagtgctg gagaagaacg tcactgtgac ccattcagtc aatctgctgg  3600
aagataaaca caacggaaag ctgtgcaaac tgcggggcgt ggcccctctg catctgggga  3660
agtgtaatat tgctggatgg atcctgggca acccagagtg cgaaagcctg tccacagcat  3720
ctagttggtc atacattgtc gagactccca gctccgacaa tgggacctgt tatcctggag  3780
attttatcga ctacgaagag ctgagagaac agctgtctag tgtgtcaagc ttcgagaggt  3840
tgaaatttt cccaaaaaca tcctcttggc ccaaccacga tagtaataag ggcgtcactg  3900
ccgcttgccc tcatgcaggg gccaaatcat tttataagaa cctgatctgg ctggtgaaaa  3960
agggaaatag ctacccaaaa ctgtccaagt cttatattaa cgacaaaggc aaggaggtcc  4020
tggtgctgtg ggggatccac catcccagta cctcagctga tcagcagagc ctgtaccaga  4080
atgcagacac atatgtcttc gtgggatcct ctcgctacag taaaaagttt aaacctgaaa  4140
ttgccatccg accaaaggtc cgggatcagg agggcagaat gaactattac tggactctgg  4200
tggaacctgg agacaaaatt accttcgagg ctacaggaaa tctggtcgtg cctagatatg  4260
```

```
catttgccat ggaacgcaac gctggctcag ggatcattat cagcgatact ccagtccacg    4320
actgtaatac cacatgccag actcccaagg gagcaattaa cacctccctg cctttccaga    4380
atatccatcc aattacaatc ggcaaatgtc ccaagtacgt gaaatctact aagctgcgac    4440
tggccaccgg gctgcggaac attcctagta tccagtcaag aggactgttt ggcgctattg    4500
cagggttcat cgagggaggc tggacaggga tggtcgatgg atggtatggc taccaccatc    4560
agaatgaaca ggggagcgga tatgccgctg acctgaaatc cactcagaac gcaattgatg    4620
agatcaccaa taaggtgaac tctgtcattg aaaaaatgaa tacacagttt actgccgtgg    4680
gcaaggagtt caaccacctg gaaaaaagga tcgagaatct gaacaagaaa gtggacgatg    4740
ggtttctgga catttggacc tacaatgctg aactgctggt gctgctggag aacgaacgca    4800
cactggatta tcatgacagt aatgtgaaga acctgtacga gaaagtgcga agccagctga    4860
agaataacgc caaagaaatc ggaaatggct gcttcgagtt ttatcacaag tgtgataaca    4920
cctgcatgga aagcgtgaag aatgggacat acgactatcc caagtactcc gaggaggcta    4980
agctgaaccg cgaggagatt gatggcgtga agctggagtc taccagaatc taccagatcc    5040
tggccatcta cagcaccgtg gccagctccc tggtgctggt ggtgtctctg ggcgccatca    5100
gcttctggat gtgtagcaac ggctccctgc agtgccggat ctgtatctga gctagcggat    5160
ccgaattcct gcagggaaag ttttataggt agttgataga acaaaataca aattttgta    5220 aaaataaatc acttttata ctaatatgac acgattacca atacttttgt tactaatatc    5280
attagtatac gctacacctt ttcctcagac atctaaaaaa ataggtgatg atgcaacttt    5340
atcatgtaat cgaaataata caaatgacta cgttgttatg agtgcttggt ataaggagcc    5400
caattccatt attcttttag ctgctaaaag cgacgtcttg tattttgata attataccaa    5460
ggataaaata tcttacgact ctccatacga tgatctagtt acaactatca caattaaatc    5520
attgactgct agagatgccg gtacttatgt atgtgcattc tttatgacat cgcctacaaa    5580
tgacactgat aaagtagatt atgaagaata ctccacagag ttgattgtaa atacagatag    5640
tgaatcgact atagacataa tactatctgg atctacacat tcaccagaaa ctagttaagc    5700
ttgtctccct atagtgagtc gtattagagc ttggcgtaat catggtcata gctgtttcct    5760
gtgtgaaatt gttatccgct cacaattcca cacaacatac gagccggaag cataaagtgt    5820
aaagcctggg gtgcctaatg agtgagctaa ctcacattaa ttgcgttgcg ctcactgccc    5880
gctttcgagt cgggaaacct gtcgtgccag ctgcattaat gaatcggcca acgcgcgggg    5940
agaggcggtt tgcgtattgg gcgctcttcc gcttcctcgc tcactgactc gctgcgctcg    6000
gtcgttcggc tgcggcgagc ggtatcagct cactcaaagg cggtaatacg gttatccaca    6060
gaatcagggg ataacgcagg aaagaacatg tgagcaaaag gccagcaaaa ggccaggaac    6120
cgtaaaaagg ccgcgttgct ggcgtttttc cataggctcc gcccccctga cgagcatcac    6180
aaaaatcgac gctcaagtca gaggtggcga aacccgacag gactataaag ataccaggcg    6240
tttccccctg gaagctccct cgtgcgctct cctgttccga ccctgccgct taccggatac    6300
ctgtccgcct ttctcccttc gggaagcgtg gcgctttctc atagctcacg ctgtaggtat    6360
ctcagttcgg tgtaggtcgt tcgctccaag ctgggctgtg tgcacgaacc cccgttcag    6420 cccgaccgct gcgccttatc cggtaactat cgtcttgagt ccaacccggt aagacacgac    6480
ttatcgccac tggcagcagc cactggtaac aggattagca gagcgaggta tgtaggcggt    6540
gctacagagt tcttgaagtg gtggcctaac tacggctaca ctagaaggac agtatttggt    6600
```

```
atctgcgctc tgctgaagcc agttaccttc ggaaaaagag ttggtagctc ttgatccggc      6660
aaacaaacca ccgctggtag cggtggtttt tttgtttgca agcagcagat tacgcgcaga      6720
aaaaaaggat ctcaagaaga tcctttgatc ttttctacgg ggtctgacgc tcagtggaac      6780
gaaaactcac gttaagggat tttggtcatg agattatcaa aaaggatctt cacctagatc      6840
cttttaaatt aaaaatgaag ttttaaatca atctaaagta tatatgagta aacttggtct      6900
gacagttacc aatgcttaat cagtgaggca cctatctcag cgatctgtct atttcgttca      6960
tccatagttg cctgactccc cgtcgtgtag ataactacga tacgggaggg cttaccatct      7020
ggccccagtg ctgcaatgat accgcgagac ccacgctcac cggctccaga tttatcagca      7080
ataaaccagc cagccggaag ggccgagcgc agaagtggtc ctgcaacttt atccgcctcc      7140
atccagtcta ttaattgttg ccgggaagct agagtaagta gttcgccagt taatagtttg      7200
cgcaacgttg ttggcattgc tacaggcatc gtggtgtcac gctcgtcgtt tggtatggct      7260
tcattcagct ccggttccca acgatcaagg cgagttacat gatcccccat gttgtgcaaa      7320
aaagcggtta gctccttcgg tcctccgatc gttgtcagaa gtaagttggc cgcagtgtta      7380
tcactcatgg ttatggcagc actgcataat tctcttactg tcatgccatc cgtaagatgc      7440
ttttctgtga ctggtgagta ctcaaccaag tcattctgag aatagtgtat gcggcgaccg      7500
agttgctctt gcccggcgtc aatacgggat aataccgcgc cacatagcag aactttaaaa      7560
gtgctcatca ttggaaaacg ttcttcgggg cgaaaactct caaggatctt accgctgttg      7620
agatccagtt cgatgtaacc cactcgtgca cccaactgat cttcagcatc ttttactttc      7680
accagcgttt ctgggtgagc aaaaacagga aggcaaaatg ccgcaaaaaa gggaataagg      7740
gcgacacgga aatgttgaat actcatactc ttcctttttc aatattattg aagcatttat      7800
cagggttatt gtctcatgag cggatacata tttgaatgta tttagaaaaa taaacaaata      7860
ggggttccgc gcacatttcc ccgaaaagtg ccacctgacg tctaagaaac cattattatc      7920
atgacattaa cctataaaaa taggcgtatc acgaggccct ttcgtctcgc gcgtttcggt      7980
gatgacggtg aaaacctctg acacatgcag ctcccggaga cggtcacagc ttgtctgtaa      8040
gcggatgccg ggagcagaca agcccgtcag ggcgcgtcag cgggtgttgg cgggtgtcgg      8100
ggctggctta actatgcggc atcagagcag attgtactga gagtgcacca tatgcggtgt      8160
gaaataccgc acagatgcgt aaggagaaaa taccgcatca ggcgccattc gccattcagg      8220
ctgcgcaact gttgggaagg gcgatcggtg cgggcctctt cgctattacg ccagctggcg      8280
aaagggggat gtgctgcaag gcgattaagt tgggtaacgc cagggttttc ccagtcacga      8340
cgttgtaaaa cgacggccag tgaattggat taggtgaca ctata                      8385
```

<210> SEQ ID NO 20
<211> LENGTH: 3361
<212> TYPE: DNA
<213> ORGANISM: Artificial Sequence
<220> FEATURE:
<223> OTHER INFORMATION: MVA construct

<400> SEQUENCE: 20

```
ttaattgtca tactcctctg cattgtctcc gaagaaataa gatccttcat tattcatgtc       60
aaaggaaggc acgatcgggt tcgttgcctt ttcgtccgag agctcgaaga ctccccgccc      120
ctggaatgac acatcttctg gtctggcact ttccatcatt cttatgattt cagtcctcat      180
gtcagacgtt ctgccctcag tatttcctgt aaatgctgcc ataatggtcg ctcttttcaaa     240 gggaaggttt ctctggaccg agaaagtggg ctgaacgctg atctgtcctg cagatgccct      300
```

```
ctgctggttg gtgtttcctc cgcttctggt tcttatagcc caatatctgc ttctcagttc    360
aagagtgttg gagtccattg cctccatgtt ctcatttgaa gcaatttgaa cccctctggt    420
ggatagctgt cctcttggga ccactcttgt ccctctgatg aaacttgaga ctctaaggtc    480
ctcaaatgct gcagagtggc atgccatcca cactaattga ctcttatgtg ctggattctc    540
atttggtcta atgagactaa agacctggct gttttgaagc aggcggaaag gatctattcc    600
aaccagagag tacccttctc tctcaaagtc atatccactg ccactgcaa gtccgtacac     660 acaagcaggc aagcaggact tatgggccac tgatcctctc aggatgagtg cagaccgtgc    720 cagaaaatg agatcttcaa tttcagcatt cccaggattt ctgctctctc gcacttgatc     780
catcattgct ctttgtgctg ctgtttggaa tttcccttttg aggatgttgc acattctctc    840
atatgcaatc cttgttcttc ttccattttc gcctctccag aaattccggt cgttgatccc    900 tcgtttatc atccgaatca gctccatcac cattgtccct accccttta ctgctgcacc      960 ggcagctcca gatctcctcg ggagagttga cccttgcatc agagagcaca tccttgggtc    1020
cattccagta cgcacgagag ctctcgttct ctgatatgtg gcatcattta gattggaatg    1080
ccatatcatc aggtgggtaa gaccagcagt tgcgtcctct ccattgttcg cttgacgcca    1140
aatcctcctg atctcctctt tgtcgtacag aattagctct ctcacccatt tccgtctct     1200 cctccgataa attggacctc cagtcttctt cgggtccttt cccgcactgg ggtgttcttc    1260
caggtatctg ttccttcttt catcaaatgc agagagtacc attctctcta ttgttatgct    1320
gttctggatc agcctccctt catagtcact gagtttgagt tctgtgcaca tctgtatgta    1380
gaacctccca atgccactaa ccattcttcc aacagatgcc ctgatctcag tagcattctg    1440
gcgttcccca ccagtttcca tctgttcata agatcgtttg gtgccttgag acgcgccggc    1500
tggactagcg atggatgaag tcacgaatat aagcacgct attaatccgt atatcatcat     1560
cccggtctta tttatattcc aaaaaaaaaa aataaaattt caatttttcc ggaaaaattg    1620
aaattttatt tttttttttt ggaatataaa taagcccggg atgaaggcca tcctggtcgt    1680
gctgctgtac accttcgcca ccgccaacgc cgacacactg tgtatcgggt atcacgcaaa    1740
caatagtact gataccgtcg acacagtgct ggagaagaac gtcactgtga cccattcagt    1800
caatctgctg gaagataaac acaacggaaa gctgtgcaaa ctgcggggcg tggcccctct    1860
gcatctgggg aagtgtaata ttgctggatg gatcctgggc aacccagagt gcgaaagcct    1920
gtccacagca tctagttggt catacattgt cgagactccc agctccgaca atgggacctg    1980
ttatcctgga gattttatcg actacgaaga gctgagagaa cagctgtcta gtgtgtcaag    2040
cttcgagagg tttgaaattt tcccaaaaac atcctcttgg cccaaccacg atagtaataa    2100
gggcgtcact gccgcttgcc ctcatgcagg gccaaatca ttttataaga acctgatctg     2160
gctggtgaaa aagggaaata gctacccaaa actgtccaag tcttatatta acgacaaagg    2220
caaggaggtc ctggtgctgt ggggggatcc ccatcccagt acctcagctg atcagcagag    2280
cctgtaccag aatgcagaca catatgtctt cgtgggatcc tctcgctaca gtaaaaagtt    2340
taaacctgaa attgccatcc gaccaaaggt ccgggatcag gagggcagaa tgaactatta    2400
ctggactctg gtggaacctg gagacaaaat taccttcgag gctacaggaa atctggtcgt    2460
gcctagatat gcatttgcca tggaacgcaa cgctggctca gggatcatta tcagcgatac    2520
tccagtccac gactgtaata ccacatgcca gactcccaag ggagcaatta cacctcccta    2580 gccttccag aatatccatc caattacaat cggcaaatgt cccaagtacg tgaaatctac      2640
```

-continued

```
taagctgcga ctggccaccg ggctgcggaa cattcctagt atccagtcaa gaggactgtt   2700
tggcgctatt gcagggttca tcgagggagg ctggacaggg atggtcgatg gatggtatgg   2760
ctaccaccat cagaatgaac aggggagcgg atatgccgct gacctgaaat ccactcagaa   2820
cgcaattgat gagatcacca ataaggtgaa ctctgtcatt gaaaaaatga atacacagtt   2880
tactgccgtg ggcaaggagt tcaaccacct ggaaaaaagg atcgagaatc tgaacaagaa   2940
agtggacgat gggtttctgg acatttggac ctacaatgct gaactgctgg tgctgctgga   3000
gaacgaacgc acactggatt atcatgacag taatgtgaag aacctgtacg agaaagtgcg   3060
aagccagctg aagaataacg ccaaagaaat cggaaatggc tgcttcgagt tttatcacaa   3120
gtgtgataac acctgcatgg aaagcgtgaa gaatgggaca tacgactatc ccaagtactc   3180
cgaggaggct aagctgaacc gcgaggagat tgatggcgtg aagctggagt ctaccagaat   3240
ctaccagatc ctggccatct acagcaccgt ggccagctcc ctggtgctgg tggtgtctct   3300
gggcgccatc agcttctgga tgtgtagcaa cggctccctg cagtgccgga tctgtatctg   3360
a                                                                    3361
```

COMPOSITIONS, METHODS AND USES FOR POXVIRUS ELEMENTS IN VACCINE CONSTRUCTS AGAINST INFLUENZA VIRUS SUBTYPES OR STRAINS

CROSS REFERENCE TO RELATED APPLICATION

The present application is a continuation-in-part application of U.S. Non Provisional application Ser. No. 13/510,601 filed as a 371 application on May 17, 2012 that claims priority to PCT Application No. PCT/US10/057,682 filed on Monday Nov. 22, 2010 (Nov. 20, 2010 fell on a Saturday) which claims the benefit of U.S. Provisional Patent Application Ser. No. 61/263,327, filed on Nov. 20, 2009. These applications are incorporated herein in their entirety for all purposes.

FEDERALLY FUNDED RESEARCH

Some embodiments disclosed herein were supported in part by grant number 1R43AI061940-01 from the National Institutes of Health and grant number 5R41AI074308-02 also from the National Institutes of Health. The U.S. Government has certain rights to practice the subject invention.

FIELD

Embodiments of the present invention report methods, compositions and uses for generating vaccine compositions. In some embodiments, poxvirus elements can be used in viral constructs, for example, a construct of use in vaccines. In some embodiments, a poxvirus element may be a secretory signal. In certain embodiments, methods for making and using constructs for vaccine preparations that include, but are not limited to, using attenuated or modified vaccinia virus vectors that can express peptides derived from different organisms or different subtypes of organisms. In other embodiments, constructs may be generated for use in vaccination against influenza. In yet other embodiments, compositions and methods herein report pre-exposing a subject to a construct composition prior to administering a vaccine to the subject. In yet other embodiments, compositions and methods herein concern generating constructs of use in vaccinations for cross-protection against more than one subtype or strain of influenza virus.

BACKGROUND

Vaccines to protect against viral infections have been effectively used to reduce the incidence of human disease. One of the most successful technologies for viral vaccines is to immunize animals or humans with a weakened or attenuated strain of the virus (a "live, attenuated virus"). Due to limited replication after immunization, the attenuated strain does not cause disease. However, the limited viral replication is sufficient to express the full repertoire of viral antigens and generates potent and long-lasting immune responses to the virus. Thus, upon subsequent exposure to a pathogenic strain of the virus, the immunized individual is protected from disease. These live, attenuated viral vaccines are amongst the most successful vaccines used in public health.

Influenza is an orthomyxovirus with three genera, types A, B, and C. The types are distinguished by the nucleoprotein antigenicity. Influenza B is a human virus and does not appear to be present in an animal reservoir. Type A viruses exist in both human and animal populations, with significant avian and swine reservoirs.

Annual influenza A virus infections have a significant impact in terms of human lives, between 500,000 and 1,000,000 die worldwide each year, and economic impact resulting from direct and indirect loss of productivity during infection. Of even greater concern is the ability of influenza A viruses to undergo natural and engineered genetic change that could result in the appearance of a virus capable of rapid and lethal spread within the population.

One of the most dramatic events in influenza history was the so-called "Spanish Flu" pandemic of 1918-1919. In less than a year, between 20 and 40 million people died from influenza, with an estimated one fifth of the world's population infected. The US military was devastated by the virus near the end of World War I, with 80% of US army deaths between 1918 and 1919 due to influenza infection. Because it is a readily transmitted, primarily airborne pathogen, and because the potential exists for the virus to be genetically engineered into novel forms, influenza A represents a serious biodefense concern.

The past two decades have seen the emergence of highly virulent avian H5N1 influenza viruses. H5N1 avian influenza first emerged in the human population when the virus crossed the avian to human species barrier in 1997. These viruses are currently endemic to poultry populations in South East Asia, where they initially emerged. Over the past decade, they have significantly broadened their host and geographic range with a current human mortality rate of approximately 60%. Compounding this threat is the resistance displayed by H5N1 viruses to both classes of influenza antivirals.

Current public and scientific concern over the possible emergence of a pandemic strain of influenza, poxviruses or other pathogenic or non-pathogenic viruses requires effective preventative measures. Another challenge regarding generating vaccines has been to generate vaccines that protects against more than one strain of a virus

SUMMARY

Embodiments of the present invention report methods, compositions and uses for generating novel vaccine compositions. In some embodiments, poxvirus elements can be used in vaccine constructs. In other embodiments, compositions and methods for administering poxvirus elements prior to receiving a vaccine can be used, for example, to circumvent interference from pre-exposure to poxvirus elements. In some embodiments, a poxvirus element may be a secretory signal or other poxvirus element. In certain embodiments, methods for making and using constructs for vaccine preparations including, but not limited to, using attenuated or modified vaccinia virus vectors expressing viral-bacterial, protozoal, fungal, or mammalian peptides to induce an immune response in a subject. In other embodiments, constructs may be generated for use in vaccines that protect against infectious diseases or in vaccines used as therapies (e.g. for cancer, diabetes, Alzheimer's disease, etc.). Some embodiments are of use as a therapeutic or as a prophylactic against a medical condition in a subject. In other embodiments, constructs may be generated for use in vaccination against viral diseases. In further embodiments, constructs may be generated for use in vaccines to protect from influenza.

Embodiments of the present invention generally relate to methods, compositions and uses for expressing peptides (e.g. poxvirus associated peptides and non-poxvirus peptides) to stimulate immune responses. In some embodiments, viral peptide formulations presented herein can be used to boost an immune response in a subject before, during and/or after vaccination of the subject or to overcome pre-existing immunity (e.g. previous poxvirus exposure) in the subject. Certain embodiments report making and using constructs of the present invention for treating or protecting a subject having been exposed or likely to be exposed to a pathogen. In accordance with these embodiments a pathogen can include a bacterial, viral, protozoal or fungal pathogen. In some embodiments, a pathogen can be influenza virus.

In accordance with embodiments disclosed herein, constructs may include, but are not limited to, attenuated or modified vaccinia virus vectors expressing bacterial-, viral-, fungal-, protozoal-associated gene segments (e.g. non-poxvirus peptides). For example, certain methods and compositions report making and using compositions having constructs including, but not limited to, attenuated or modified vaccinia virus vectors expressing influenza-associated gene segments in order to induce an immune response in a subject against the influenza. Certain compositions report constructs having antigens or peptides derived from influenza and associated with or combined with poxviruses related elements. Influenza gene or gene segments can include, but are not limited to, hemagglutinin (HA gene segment), neuraminidase (NA gene segment), nucleoprotein (NP gene segment), matrix protein (M gene segment), polymerase (P) and a combination thereof. Some embodiments report vaccine compositions capable of reducing or preventing infection in a subject caused by exposure to a poxvirus and/or influenza virus. Some embodiments concern using a fragment of one or more influenza gene segments for example, a fragment can include at least 6, or at least 8, or at least 10, or at least 15, or at least 20 contiguous etc amino acids of an influenza gene segment, up to the full length of the gene segment.

In other embodiments, influenza fragments in a single construct can be from more than one influenza subtype or strain. In certain examples, a construct of use in a vaccine can contain one or more of the same gene segments of different strains or one or more different gene segments from different strains of influenza (e.g. HA, NA, NP and M). Some embodiments include constructs having one or more influenza gene segments from different strains where each segment has an associated signal sequence (e.g. naturally-occurring or artificial (e.g. from a different organism)). Some embodiments concern constructs that require a signal sequence in close proximity to one or more gene segments of the construct (e.g. C13L next to NP). Other embodiments concern secretory signal sequences fused to one or more influenza gene segments of constructs described herein (e.g. fused to either end of the gene segment). In other embodiments, certain naturally-occurring influenza gene segments used in constructs described are already associated with a secretory signal (e.g. HA). Constructs contemplated herein can further include a modified viral vector (e.g. MVA). In accordance with these embodiments, pharmaceutical compositions containing one or more of these constructs can be use to generate a vaccine capable of conferring protection in a subject from more than one influenza strain or variety. For example, a subject may be conferred protection from H1NI, H5N1, H3N2 or any other influenza strain or variety in a single composition vaccine.

In some aspects, constructs of use as vaccine compositions, can include a secretory signal sequence alone or in combination with a translation control region sequence. In accordance with these embodiments, the secretory signal sequence can be one or more signal sequences from a poxvirus. In other embodiments, the secretory signal sequence can include, but are not limited to, tissue plasminogen activator (WA) leader sequence, the co-factor leader sequence, the preproinsulin leader sequence, the invertase leader sequence, the immunoglobulin A leader sequence, the ovalbumin leader sequence, and the P-globin leader sequence or other proleader sequences and combinations thereof In certain embodiments, a pre-boost of a construct may be used to induce a greater immune response in a subject to a subsequent vaccination. In some embodiments, a vaccinia virus derived gene sequence may be used to pre-boost a subject. In accordance with these embodiments, a pre-boost construct can contain modified vaccinia Ankara (MVA). It is contemplated that these pre-boosts can be administered to a subject by any method. For example, the pre-boost can be introduced intramuscularly or intradermally or by another method. In addition, a pre-boost may be administered to a subject followed by introduction of a construct having one or more elements derived from a pathogen or associated with a condition to boost an immune response in the subject. In certain examples, a pre-boost could be 6 months or less prior to a vaccination, or 5 months or less, or 4 months or less, or 3 months or less, or 1 month or less or a few weeks or immediately prior to administering a vaccine to a subject. Administration regimens are readily determinable by one skilled in the art for pre-boosts, boost and post-boosts related to vaccinating a subject against an infection or a condition.

Other embodiments concern kits for making or using compositions disclosed. It is reported that a kit may include constructs having a modified vaccinia viral vector and one or more enterobacterial antigen.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

FIGS. 1A and 1B represent exemplary plots of parameters in mice after intramuscular (IM) or intradermal (ID) introduction of various constructs of some embodiments described herein to the mice followed by challenge with influenza, FIG. 1A) Weight loss and FIG. 1B) Viral Lung titers on day 4 post-challenge.

FIGS. 2A-2C represent exemplary plots of experiments where mice were vaccinated intradermal (ID) with various influenza challenge concentration and then examined on day 63 post-vaccination. Weight loss curves are displayed for some of the constructs FIG. 2A) MVA/IRES/tPA/HA, FIG. 2B) MVA/IRES/C13L/HA, and FIG. 2C) MVA/HA native.

FIG. 3 represents an exemplary plot that illustrates various constructs and effects on long-term immune protection in mice against a viral insult.

FIG. 4 represents an exemplary plot that illustrates cross-clade protection using various viral-derived antigens.

FIG. 5 represents an exemplary plot of mice tested with certain constructs described herein, described herein to the mice followed by a viral challenge.

FIGS. 6A and 6B represent exemplary plots of parameters in mice after intramuscular (IM) introduction of various constructs of some embodiments described herein to the mice followed by challenge with influenza, FIG. 6A) Weight loss and FIG. 6B) Survival post-challenge.

FIGS. 7A and 7B represent exemplary plots of parameters in mice after intradermal (ID) introduction of various constructs of some embodiments described herein to the mice followed by challenge with influenza, FIG. 7A) Weight loss and FIG. 7B) Survival post-challenge.

FIGS. 8A and 8B represent exemplary plots of parameters in mice after (FIG. 8A) intramuscular (IM) or (FIG. 8B)

intradermal (ID) introduction of various constructs of some embodiments described herein to the mice followed by challenge with influenza.

FIG. 10A represents construct MVA/HA and FIG. 10B represents construct MVA/IRES/tpa/HA.

FIG. 10C illustrates Table 1 which represents MVA influenza transfer vectors and constructs.

FIGS. 11A and 11B represent exemplary plots of percent weight change in mice after introduction of 2 different constructs of some embodiments described herein followed by challenge with influenza. FIG. 11A represents construct MVA/IRES/C13L/HA and FIG. 11B represents construct MVA-GFP.

FIGS. 12A and 12B represent exemplary plots of percent weight change in mice after introduction of 2 different constructs at various concentrations of some embodiments described herein followed by challenge with influenza. FIG. 12A. represents construct MVA/IRES/tpa/Hat and FIG.12B represents construct MVA/IRES/C13L/Hat.

FIG. 13A represents construct MVA/HA and FIG. 13B represents construct MVA/IRES/tpa/HA.

FIG. 14A represents construct MVA/IRES/tpa/HA and FIG. 14B represents construct MVA/IRES/C13L/HA.

FIGS. 15A and 15B represent exemplary plots of survival in mice after introduction of 2 different constructs at various concentrations of some embodiments described herein followed by challenge with influenza (dpi represents days post infection). FIG. 15A represents construct MVA/IRES/tpa/HAt and FIG. 15B represents construct MVAIRES/C13L/HAt.

FIG. 16A represents construct MVA/HA and FIG. 16B represents construct MVA/IRES/tpa/HA.

FIGS. 17A and 17B represent exemplary plots of clinical scores (e.g. physical and physiological parameters) in mice after introduction of 2 different constructs at various concentrations of some embodiments described herein followed by challenge with influenza. FIG. 17A represents construct MVA/IRES/C13L/HA and FIG. 17B represents construct MVA/IRES/tpa/HAt.

FIG. 18 represents an exemplary plot of clinical scores (e.g. physical and physiological parameters) in mice after introduction of a construct at various concentrations of some embodiments described herein followed by challenge with influenza.

FIG. 20 represents an exemplary plot of survival of mice challenged above after exposure to the same constructs as in FIGS. 19A and 19B.

FIG. 21 is a schematic representation of a recombinant plasmid construct.

Figures 22A, 22B, 22C, 22D, 22E:
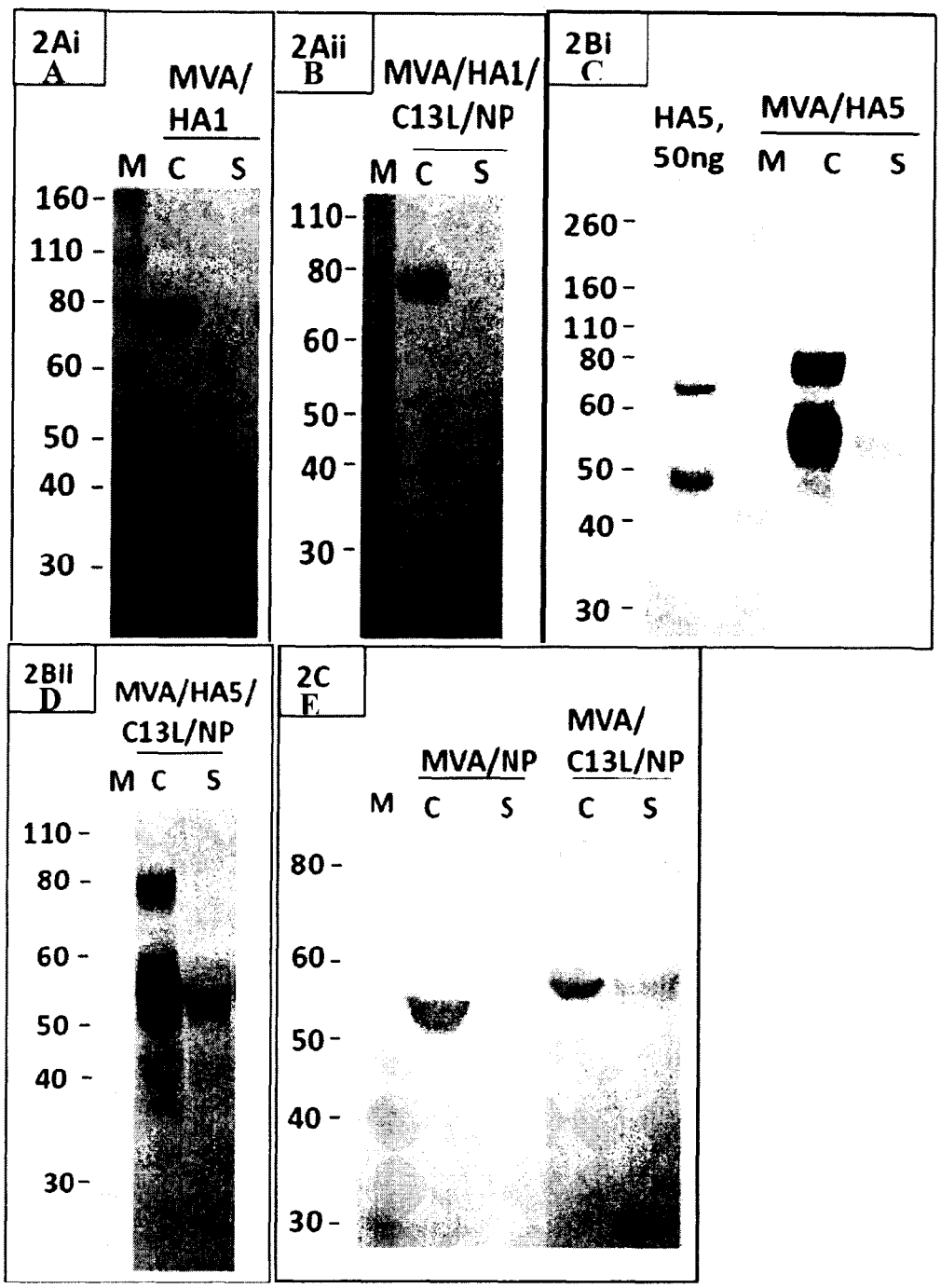

FIGS. 22A-22E represent gel electrophoresis separation of constructs of certain embodiments contemplated herein. FIG. 22A represents construct MVA/HA1; FIG. 22B represents construct MVA/HA1/C13L/NP; FIG. 22C represents HA5 and construct MVA/HA5; FIG. 22D represents construct MVA/HA5/C13L/NP and FIG. 22E represents constructs MVA/NP and MVA/C13L/NP.

Figure 23A:
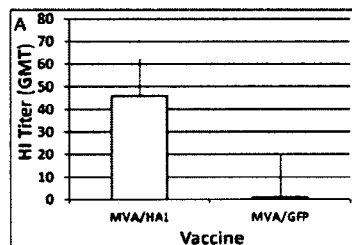
Figure 23C:
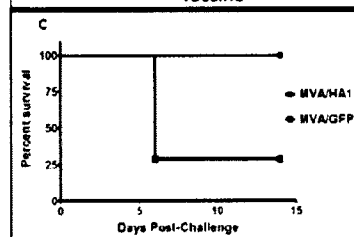
Figure 23E:
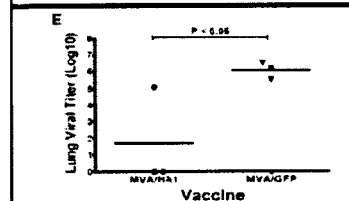
Figure 23G:
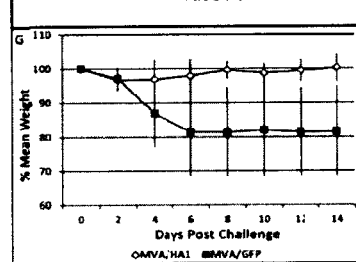
Figure 23B:
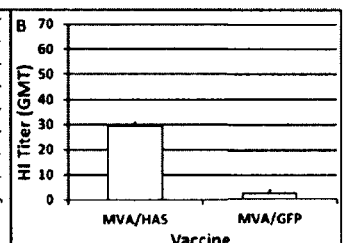
Figure 23D:
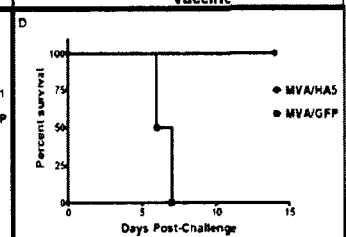
Figure 23F:
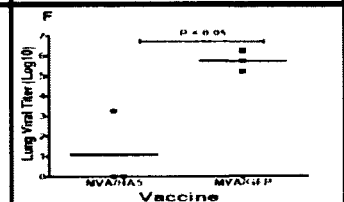
Figure 23H:
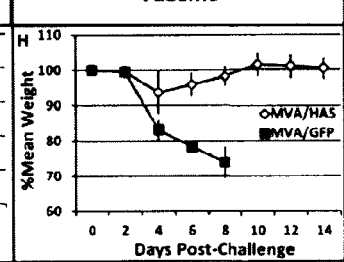

FIGS. 23A-23H represent vaccine efficacy against homologous challenge of influenza virus. FIGS. 23A and 23B represents histogram plots of construct MVA/HA1 and MVA/GFP; FIG. 23C and 23D represents days post challenge of various constructs; FIGS. 23E and 23F represents lung viral titer post challenge with various constructs and FIG. 23G and 23H represents weight loss in an animal model post challenge after exposure to various constructs.

Figure 24:
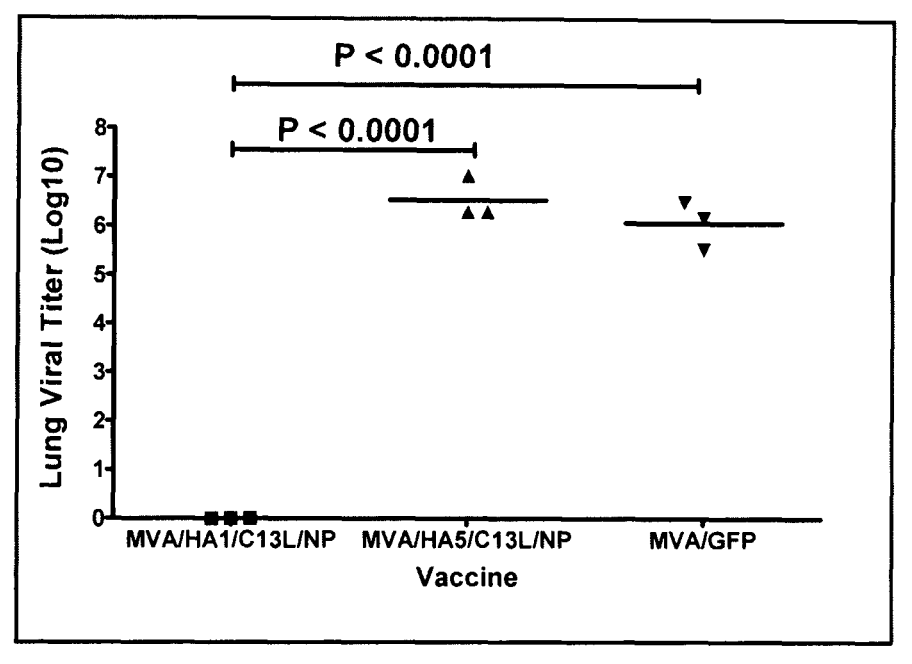

FIG. 24 represents lung viral titers in vaccinated and control animals following challenge with an influenza virus.

FIGS. 25A-25D represents grafts representing exemplary immune responses following vaccinations of various constructs contemplated herein. FIGS. 25A, 25B, 25C and 25D represents weight loss in an animal model post challenge after exposure to various constructs.

FIGS. 26A-26B represent effects of vector immunity on vaccine efficacy. FIG. 26A represents various vaccinations regiments in an animal model. FIG. 26B represents percent survival post challenge using various vaccination regiments in the animal model.

Figure 27:
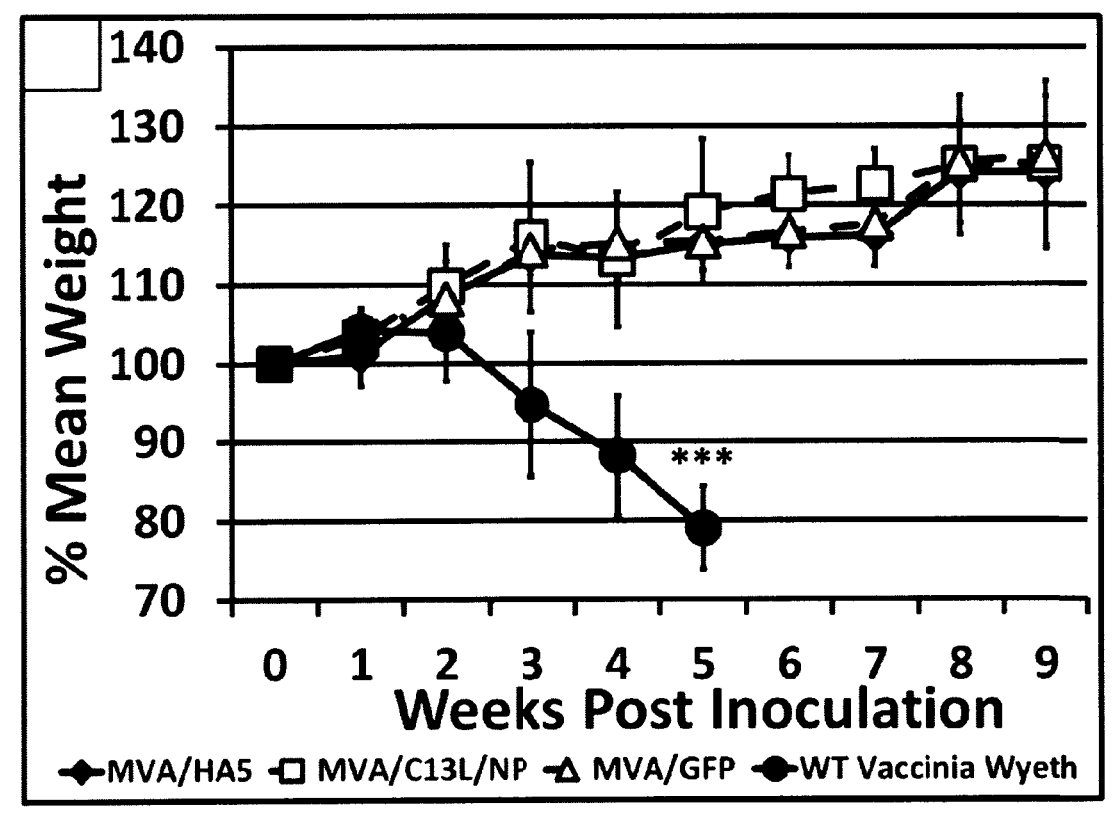

FIG. 27 is a graphic representation of examination of safety of vectored vaccine compositions of some embodiments herein.

Figure 28:
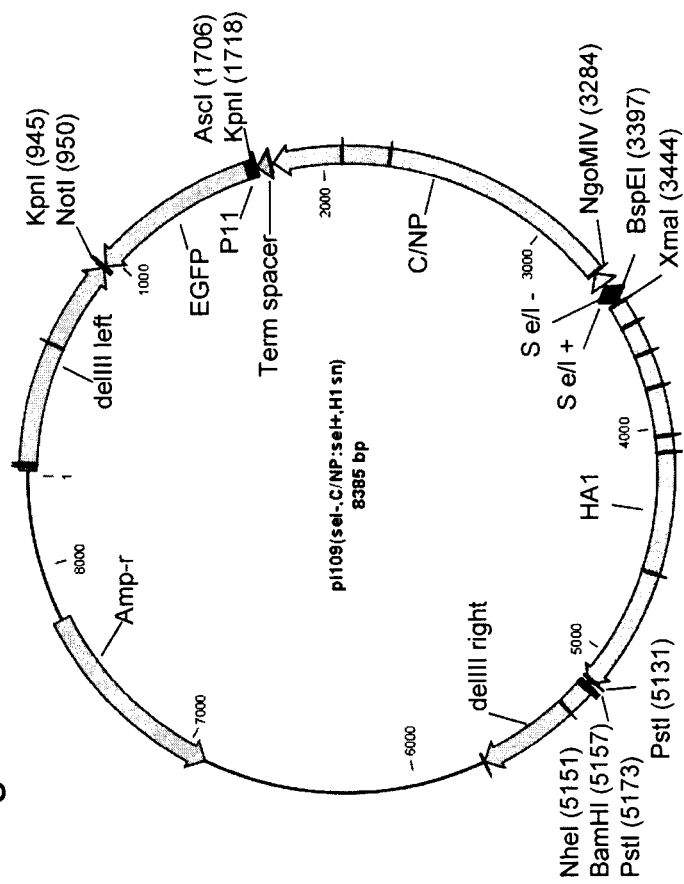

FIG. 28 represent an exemplary plasmid construct of some embodiments herein.

Figure 29:
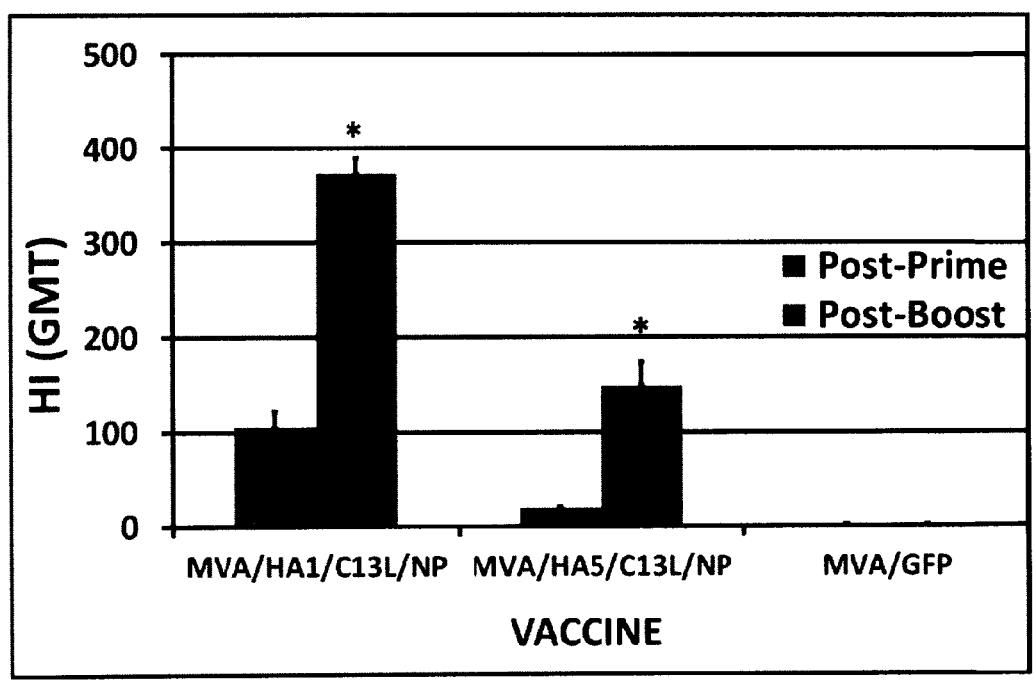

FIG. 29 represents a histogram plot of exemplary immune responses following prime and booster vaccinations of various constructs contemplated herein.

DEFINITIONS

As used herein, "a" or "an" can mean one or more than one of an item.

As used herein the specification, "subject" or "subjects" can include, but are not limited to, mammals such as humans or mammals, domesticated or wild, for example dogs, cats, other household pets (e.g. hamster, guinea pig, mouse, rat), ferrets, rabbits, pigs, horses, cattle, prairie dogs, wild rodents, or zoo animals. A subject can be an adult or a child.

As used herein, "about" can mean plus or minus ten percent.

As used herein, "attenuated virus" can mean a virus that demonstrates reduced or no clinical signs of disease when administered to a subject such as a mammal (e.g. human or an animal).

As used herein, "MSC" can mean multiple cloning site.

As used herein, "dSP" can mean divergent vaccinia promoter.

As used herein, "MVA" can mean modified vaccinia Ankara.

As used herein, "EMCV" can mean encephalomyocarditis virus.

As used herein, "IRES" can mean internal ribosome entry site from encephalomyocarditis virus or other viruses.

As used herein, "IRES(A7)" can mean IRES from encephalomyocarditis virus with 7 adenosine residues in bifurcation loop; source-pCITE-1.

As used herein, "IRES(A6)" can mean IRES from encephalomyocarditis virus mutated to have 6 adenosine residues in bifuraction loop.

As used herein, "pDIIIgfp" can mean MVA del III gfp marker transfer plasmid.

As used herein, "pI*" can mean transfer vector plasmids.

As used herein, "tPA" can mean secretory signal from tissue plaminogen activator.

As used herein, "se/l" can mean synthetic optimized early late poxvirus promoter.

As used herein, "H6" can mean the vaccinia gene H6 early/late native poxvirus promoter.

As used herein, "del III" can mean modified vaccinia Ankara deletion region III.

As used herein, "GFP" can mean enhanced green fluorescent protein.

As used herein, "CEF" can mean chicken embryo fibroblasts.

As used herein, "RCN" can mean raccoon pox virus.

DESCRIPTION

In the following sections, various exemplary compositions and methods are described in order to detail various embodiments. It will be obvious to one skilled in the art that practicing the various embodiments does not require the employment of all or even some of the details outlined herein, but rather that concentrations, times and other details may be modified through routine experimentation. In some cases, well-known methods or components have not been included in the description.

Embodiments of the present invention concern methods, compositions and uses for generating novel vaccine compositions. In some embodiments, poxvirus elements can be used in vaccine constructs or in pre-immunization constructs for introduction to a subject. In certain embodiments, poxvirus elements can be used to pre-immunize a subject prior to receiving a vaccine. In some embodiments, a poxvirus element can be a secretory signal or other poxvirus element. Other embodiments concern methods for making and using constructs including, but not limited to, attenuated or modified vaccinia virus vectors expressing viral, bacterial, protozoal fungal, or mammalian derived peptides. In other embodiments, constructs may be generated for use in vaccines that protect against infectious diseases or in vaccines used as therapies (e.g. for cancer, diabetes, Alzheimer's disease, etc.) to boost an immune response in a subject. Some embodiments are of use as a therapeutic or as a prophylactic against a medical condition in a subject. In other embodiments, constructs may be generated for use in vaccination against viral diseases. In further embodiments, constructs may be generated for use in vaccines to protect from a pathogen. Some embodiments described herein concern constructs to protect against and/or treat a subject exposed to or having an influenza infection.

Influenza Virus

Influenza is an orthomyxovirus. Three genera, types A, B, and C of influenza currently exist. Types A and B are the most clinically significant, causing mild to severe respiratory illness. Type A viruses exist in both human and animal populations, with significant avian and swine reservoirs. Although relatively uncommon, it is possible for nonhuman influenza A strains to infect humans by jumping from their natural host. In one specific example, the highly lethal Hong Kong avian influenza outbreak in humans in 1997 was due to an influenza A H5N1 virus that was an epidemic in the local poultry population at that time. In this case, the virus killed six of the 18 patients shown to have been infected.

Annual seasonal influenza A or B virus infections have a significant impact on humanity both in terms of death, between 500,000 and 1,000,000 worldwide each year and economic impact resulting from direct and indirect loss of productivity during infection.

In 2009, an influenza pandemic erupted. The virus isolated from patients in the United States was found to be made up of genetic elements from four different flu viruses—North American Mexican influenza, North American avian influenza, human influenza, and swine influenza virus typically found in Asia and Europe. This new strain appears to be a result of reassortment of human influenza and swine influenza viruses, in all four different strains of subtype H1N1.

In certain embodiments, a virus can include an influenza virus infection, for example, influenza type A, B or C or subtype or strain thereof. Some embodiments include, but are not limited to, influenza A, H1N1 subtype or H1N1 of swine origin and strains. Other influenza A viruses may include, but are not limited to, H2N2, which caused Asian Flu in 1957; H3N2, which caused Hong Kong Flu in 1968; H5N1, a current pandemic threat; H7N7, which has unusual zoonotic potential; H1N2, endemic in humans and pigs; H9N2; H7N2; H7N3, H10N7 or combinations thereof. Other varieties can include, but are not limited to, ANietnam/1203/04 (H5N1), A/Norway/3487-2/09 (pandemic H1N1), A/Influenza/Puerto Rico/8/34 (seasonal H1N1) and seasonal H3N2 virus (A/Aichi/68) or others In certain embodiments, constructs having two or more influenza gene segments from different subtypes or strains can be directed toward prevention or treatment of seasonal influenza virus outbreaks. In other embodiments, construct having two or more influenza gene segments from different subtypes or strains can be directed toward prevention or treatment of pandemic influenza virus outbreaks. Other constructs can be used to target both seasonal and pandemic outbreaks of different subtypes or strains of influenza virus by using influenza gene segments specific for a given subtype or strain.

Influenza A and B each contain 8 segments of negative sense ssRNA. Type A viruses can also be divided into antigenic subtypes on the basis of two viral surface glycoproteins, hemagglutinin (HA) and neuraminidase (N). There are currently 15 identified HA subtypes (designated H1 through H15) and 9 NA subtypes (N1 through N9) all of which can be found in wild aquatic birds. Embodiments of the present invention can include constructs having one or more of any influenza gene segment subtype or strain known in the art. Of all the possible (e.g. over 135) combinations of HA and NA, four (H1N1, H1N2, H2N2, and H3N2) have widely circulated in the human population since the virus was first isolated in 1933. Two of the more common subtypes of influenza A currently circulating in the human population are H3N2 and H1N1.

Some embodiments include constructs having one or more influenza gene segments from different subtypes or strains where each gene segment has an associated signal sequence (e.g. naturally-occurring or artificial (e.g. from a different organism)). Some embodiments concern constructs that require a signal sequence in close proximity to one or more gene segments of the construct (e.g. C13L next to an NP influenza gene segment). Other embodiments concern secretory signal sequences fused to one or more influenza gene segments of constructs described herein (e.g. fused to either end of the gene segment). In other embodiments, certain naturally-occurring influenza gene segments used in constructs described are already associated with a secretory signal (e.g. HA).

New type influenza A strains emerge due in part to genetic drift that can result in slight changes in the antigenic sites on the surface of the virus. This shift can lead to the human population experiencing epidemics of influenza infection every year. More drastic genetic changes can result in an antigenic shift (a change in the subtype of HA and/or NA) resulting in a new subtype capable of rapidly spreading in a susceptible population.

Subtypes are sufficiently different as to make them non-crossreactive with respect to antigenic behavior; prior infection with one subtype (e.g. H1N1) can lead to no immunity to another (e.g. H3N2). It is this lack of crossreactivity that in certain cases allows a novel subtype to become pandemic as it spreads through an immunologically naïve population. In some embodiments, development of novel vaccine vectors and production techniques are disclosed herein for generating effective vaccine with broad cross-protective efficacy against various influenza subtypes or strains. Modified vaccinia Ankara (MVA) vector offers several advantages in such a vaccine such as; 1) safety, 2) stability, 3) rapid induction of humoral and cellular responses, and 4) multiple routes of inoculation. While several vaccines have been created using an MVA vector, most of them have been tested against homologous or closely related challenge viruses and provided limited to no protection against genetically divergent strains. In certain embodiments, vaccine constructs concern recombinant MVA vaccines expressing antigens (e.g. influenza gene segments) from two or more subtypes of influenza. Some embodiments concern influenza gene segments that are the same or different regions (e.g. HA, NA, M, NP) from two or more subtypes or strains. In certain embodiments, use of an NP segment can require a secretory signal sequence in close proximity to the gene segment in a construct. For example, certain embodiments concern fusing a secretory signal sequence to an influenza gene segment in a construct having one or more additional influenza gene segments within the same construct from different or the same influenza subtype. In certain embodiments, the constructs can be plasmid constructs.

Although relatively uncommon, it is possible for nonhuman influenza A strains to transfer from their "natural" reservoir to humans. In one example, the highly lethal Hong Kong avian influenza outbreak in humans in 1997 was due to an influenza A H5N1 virus that was an epidemic in the local poultry population at that time. This virus transferred to other hosts (e.g. humans) from contaminated chickens.

Some embodiments of the present invention report vaccine compositions including, but not limited a poxvirus and one or more poxvirus secretory signals associated with one or more non-poxvirus peptides. In certain embodiments, a vaccine composition may include a modified or attenuated poxvirus associated with one or more secretory poxvirus secretory signals associated with one or more non-poxvirus peptides. In other embodiments, recombinant modified vaccinia Ankara (MVA) vector associated with one or more poxvirus secretory signals associated with one or more non-poxvirus peptides. In other embodiments, a vaccine composition may include a recombinant modified vaccinia Ankara (MVA) vector associated with one or more influenza-associated peptides where at least one of the one or more influenza-associated peptides is associated with a poxvirus secretory signal. For example, a vaccine composition can include recombinant modified vaccinia Ankara (MVA) vector expressing influenza virus components. In accordance with this vaccine composition, an MVA construct expressing one or more influenza-associated antigens may be generated (e.g. HA, NP, NA, M, P, etc.) for use to vaccinate a subject against influenza. It is contemplated that vaccine constructs can contain a more conserved or highly conserved influenza genetic region or influenza associated peptide alone or in combination with a more variable influenza associated peptide. Alternatively, a vaccine construct contemplated herein can contain a peptide or the entire segment of an internal influenza gene region (e.g. M) or an externally (e.g. HA) exposed gene region.

In one embodiment contemplated herein, a vaccine construct can contain two influenza gene segments from different subtypes. In accordance with this embodiment, the vaccine construct can contain a hemagglutinin (HA) gene segment from H1N1 and a nucleoprotein (NP) from H5N1 each associated with a secretory signal sequence (e.g. MVA/HA$_1$/C13L/NP).

In certain embodiments, influenza virus is selected from the group consisting of any influenza A subtype or strain, influenza A H3N2, influenza A H1N1, influenza A H1N1 swine-origin, avian influenza A H5N1, and influenza B.

Certain embodiments of the present invention report compositions having constructs directed against poxviruses. For example, vaccine compositions may be directed to the prevention or reduced incidence of conditions associated with poxvirus or influenza viruses.

Poxyiridae

Poxviruses (members of the family Poxyiridae) are viruses that can, as a family, infect both vertebrate and invertebrate animals. There are four known genera of poxviruses that may infect humans: orthopox, parapox, yatapox, molluscipox. Orthopox include, but are not limited to, variola virus, vaccinia virus, cowpox virus, monkeypox virus, and smallpox. Parapox include, but are not limited to, orf virus, pseudocowpox, bovine papular stomatitis virus; Yatapox: tanapox virus, yaba monkey tumor virus. Molluscipox include, but are not limited to, molluscum contagiosum virus (MCV). Some of the more common oixviruses are vaccinia and molluscum contagiousum, but monkeypox infections seem to be on the rise.

Poxvirus family, vaccinia virus, has been used to successfully vaccinate against smallpox virus. Vaccinia virus is also used as an effective tool for foreign protein expression to elicit strong host immune response. Vaccinia virus enters cells mainly by cell fusion, although currently the receptor is not known. Virus contains three classes of genes, early, intermediate and late that are transcribed by viral RNA polymerase and associated transcription factors. Diseases caused by pox viruses have been known about for centuries.

Orthopoxviruses

Certain embodiments of the present invention may include using modified or attenuated orthopoxviruses or orthopoxvirus associated genetic elements or peptides in vaccine compositions. Orthopoxvirus is a genus of the Poxyiridae family, that includes many agents isolated from mammals, including, but not limited to, vaccinia, monkeypox, cowpox, camelpox, seal poxvirus, buffalo poxvirus, raccoon poxvirus, skunk poxvirus, vole poxvirus and ectromelia viruses. Members of Poxyiridae have large linear double-stranded DNA, with genome sizes ranging from 130 to 300 kbp. One of the members of the genus is variola virus, which causes smallpox. Smallpox was previously eradicated using another orthopoxvirus, the vaccinia virus, as a vaccine.

Modified Vaccinia Virus Ankara (MVA)

Some embodiments in the present invention report compositions and methods of use of recombinant vaccinia viruses derived from attenuated poxviruses that are capable of expressing predetermined or preconstucted genes or gene segments. Those skilled in the art recognize that other attenuated poxviruses can be generated by serial passage in cell culture or by deliberate deletion of poxyiral genes. In certain embodiments, predetermined genes may be inserted at the site of a naturally occurring deletion in the MVA genome. In other embodiments, recombinant MVA viruses can be used, for example, for the production of polypeptides (e.g. antigens) or for encoding antigens of use for vaccine compositions capable of inducing an immune response in a subject administered the vaccine compositions.

In certain embodiments, modified or attenuated poxviruses (e.g. modified vaccinia Ankara (MVA), NYVAC, LC16 m8, or CVI-78), can be used in a subject (e.g. mammals such as humans) as a delivery system for pre-boost, boost or post-boost vaccination in order to induce immunity to a pathogen in the subject. It is contemplated herein that a subject may benefit from having more than one administration of a compositions disclosed herein. Previously, MVA was administered to over 120,000 individuals and proven to be a safe and effective vaccine against smallpox. In certain embodiments, recombinant MVA vaccine candidates have been shown to induce protective humoral and cellular immunity against diseases caused by viruses, bacteria, parasites, or tumors from which antigens or peptides were derived. Additional features that make MVA a suitable vector include its ability to induce protective immune responses when administered by different routes and its genetic and physical stability properties.

Translational Control Sequences

Some embodiments may include an optional enhancer, for example, a translation control sequence. In certain embodiments, a translation control sequence may include an internal ribosomal entry site (IRES) (e.g. EMCV-IRES). Viral IRESs are classified into four groups: Group 1 (Cricket paralysis virus (CrPV), Plautia stali intestine virus (PSIV) and Taura syndrome virus (TSV)); Group 2 (Hepatitis C virus, (HCV), classical swine fever virus (CSFV) and porcine teschovirus 1 (PTV-1)); Group 3 (encephalomyocarditis virus (EMCV), foot-and-mouth-disease virus (FMDV) and Theiler's Murine Encephalomyelitis virus (TMEV)); and Group 4 (poliovirus (PV) and rhinovirus (RV)). In other embodiments, viral untranslated regions (UTRs) found 5' to viral coding sequences can be used to direct translation. Any translation control sequence of use in viral constructs known in the art is contemplated.

Secretory Signals

Alternatively, embodiments of the present invention may include constructs having one or more poxvirus secretory signal sequences in combination with other elements. Translation control sequences and/or poxvirus secretory signals were demonstrated to increase efficacy of certain vaccine constructs. In some embodiments, one or more poxvirus secretory signal sequences of constructs disclosed herein can include, but are not limited to, secretory signal sequence in the poxvirus genes C13L (putative), B8R (soluble interferon gamma receptor), B19R (interferon a/b receptor), A39R (semaphoring), M2L (putative), C13L (putative), C19L or other secretory signal sequences known in the art. Constructs disclosed herein can contain one or more secretory signal sequence.

In some embodiments, when designing a construct, such that a protein is expressed, it may be necessary to incorporate into a first nucleic acid region a DNA sequence encoding a signal sequence, for example, in cleavable form, where the expressed protein is desired to be secreted. Without limiting embodiments of the present invention to any one theory or mode of action, a signal sequence can be a peptide that is present on proteins destined either to be secreted or to be membrane bound. These signal sequences can be found at the N-terminus of the protein and are generally cleaved from a mature form of a protein. The signal sequence generally interacts with the signal recognition particle and directs the ribosome to the endoplasmic reticulum where co-translational insertion takes place. Where the signal sequence is cleavable, it is generally removed by for example, a signal peptidase. The choice of signal sequence which is to be utilized may depend on the requirements of the particular situation and can be determined by the person of skill in the art. In the context of the exemplification provided herein, but without being limited in that regard, tPA, a poxvirus signal sequences from C13L or B8R may be used to facilitate secretion of a peptide, protein, gene segment or construct of interest. If a membrane protein is desired, both a 5' cleavable signal sequence at the amino end of the protein and a non-cleavable membrane anchor at the 3'(carboxy) end of the protein may be needed. These could be provided within the vector or one or both could be encoded by the DNA of the protein of interest.

Some embodiments of the present invention include, but are not limited to, compositions including one or more constructs. A construct may be designed to produce proteins that are cytoplasmically retained, secreted or membrane bound. Deciding what form a protein of interest may need to take can depend on the functional requirement of the protein. For example, anchored cell surface expression of a protein of interest can provide a convenient way for screening for molecules that interact with a protein or peptide of interest such as antibodies, antagonists, agonists or the like particularly to the extent that the protein is expressed on the membrane of an adherent cell type. Still further membrane anchored forms of proteins may be suitable for administration to a subject for example, for generating monoclonal antibodies to the protein. This may be due to host cells providing a convenient source of the protein that is likely to be correctly folded and have appropriate post-translational modifications, for example, glycosylation and disulphide bond formation. In addition, a host cell may provide adjuvant properties, for example, antigenic differences from a recipient subject, notably in major histocompatibility complexes (MHC).

Alternatively, secreted proteins can be suitable where a protein is to be harvested and purified. A nucleic acid molecule encoding a signal sequence may be positioned in the construct at any suitable location which can be determined as a matter of routine procedure by a person of skill in the art. In some embodiments, a signal sequence may be positioned immediately 5' to the nucleic acid sequence encoding a peptide, protein or construct of interest (such that it can be expressed as an immediately adjacent fusion with the protein of interest) but 3' to a promoter such that expression of a signal sequence is placed under control of the promoter. A nucleic acid sequence encoding a signal sequence can form part of a first nucleic acid region of a construct.

It is contemplated herein that constructs and vaccine compositions disclosed can be used as therapies for conditions such as diabetes, Alzheimer's and cancer or other condition. Constructs may be generated for use in vaccines that protect against or as therapies for certain conditions (e.g. for cancer, diabetes, Alzheimer's disease, etc.). In addition, vaccine compositions and pre-boost compositions described herein can be used in subjects to boost their immune system.

Tumor Markers

Tumor markers and associated tumor peptides are contemplated for using in constructs described herein. Tumor markers and peptides associated with tumors (e.g. non-poxvirus peptides) can be used in combination with elements described herein in order to develop vaccines to treat or prevent cancer in a subject. Some tumor markers include, but are not limited to the following, 707-AP=707 alanine proline AFP=alpha (α)-fetoprotein, ART-4=adenocarcinoma antigen recognized by T cells 4, BAGE=B antigen; b-catenin/m, β-catenin/mutated, Bcr-abl=breakpoint cluster region-Abelson, CAMEL=CTL-recognized antigen on melanoma, CAP-1=carcinoembryonic antigen peptide-1, CASP-8=caspase-8, CDC27m=cell-divisioncycle, 27 mutated, CDK4/m=cycline-dependent kinase 4 mutated, CEA=carcinoembryonic antigen, CT=cancer/testis (antigen), Cyp-B=cyclophilin B, DAM=differentiation antigen melanoma (the epitopes of DAM-6 and DAM-10 are equivalent, but the gene sequences are different. DAM-6 and DAM-10, ELF2M=elongation factor 2 mutated, ETV6-AML1=Ets, variant gene 6/acute myeloid leukemia 1 gene ETS, G250=glycoprotein 250 GAGE=G antigen, GnT-V=N-acetylglucosaminyltransferase V, Gp100=glycoprotein 100 kD, HAGE=helicose antigen, HER-2/neu=human epidermal receptor-2/neurological, HLA-A*0201-R1701=arginine (R) to isoleucine (I) exchange at residue 170 of the α-helix of the α2-domain in the HLA-A2 gene, HPV-E7=human papilloma virus E7, HSP70-2M=heat shock protein 70-2 mutated, HST-2=human signet ring tumor-2, hTERT or hTRT=human telomerase reverse transcriptase, iCE=intestinal carboxyl, sterase, KIAA0205=name of the gene as it appears in databases, LAGE=L antigen, LDLR/FUT=low density lipid receptor/GDP-L-fucose: β-D-galactosidase 2-α-Lfucosyltransferase, MAGE=melanoma antigen, MART-1/Melan-A=melanoma, antigen recognized by T cells-1/Melanoma antigen A, MC1R=melanocortin 1 receptor, Myosin/m=myosin mutated, MUC1=mucin, MUM-1, -2, -3=melanoma, ubiquitous mutated 1, 2, 3 NA88-A=NA cDNA clone of patient M88, NY-ESO-1=New York-esophageous 1, P15=protein 15, p190 minor bcr-ab1=protein of 190, KD bcr-ab1, Pm1/RARa=promyelocytic leukaemia/retinoic acid receptor α, PRAME=preferentially expressed antigen of melanoma, PSA=prostate-specific antigen, PSM=prostate-specific membrane antigen, RAGE=renal antigen, RU1 or RU2=renal, ubiquitous 1 or 2, SAGE=sarcoma antigen, SART-1 or SART-3=squamous antigen, rejecting tumor 1 or 3, TEL/AML1=translocation Ets-family leukemia/acute myeloid, leukemia 1, TPI/m=triosephosphate isomerase mutated, TRP-1=tyrosinase related, protein 1, or gp75, TRP-2=tyrosinase related protein 2, TRP-2/INT2=TRP-2/intron, WT1=Wilms' tumor gene and any other tumor antigen known in the art. In certain embodiments, a pre-boost having an MVA construct can be used alone or prior to administering a vaccine having a tumor antigen derived peptide to a subject in need thereof.

Anti-microbial peptides are contemplated of use in constructs disclosed herein. Anti-microbial peptides can be expressed in constructs described and used alone or after a subject is administered a pre-immune boost to treat or prevent an infection.

Selection Markers

In certain embodiments, additional selection markers may be used, for example, one may insert any number of selection markers which may be designed, for example, to facilitate the use of the vectors in a variety of ways, such as purification of a molecule of interest. For example, glutathione S-transferase (GST) gene fusion system provides a convenient means of harvesting a construct, protein or peptide of interest. Without limiting to any one theory or mode of action, a GST-fusion protein can be purified, by virtue of the GST tag, using glutathione agarose beads. Embodiments of the present invention should be understood to extend to constructs encoding secretable CST-molecule fusion. This could be achieved, for example, by designing the sequence of a first nucleic acid region such that it encodes a cleavable signal sequence fused to a cleavable GST which is, in turn, fused to the molecule of interest. In another example, a fusion tag could be used. In accordance with these embodiments, a fusion tag can be between 360 bp of protein A (allowing purification of the secreted product) and beta lactamase (a bacterial enzyme which allows testing of supernatants by a simple colour reaction). Beta lactamase facilitates selection of an assay for a molecule of interest in the absence of an assay for molecule of interest. The protein A/beta lactamase fusion can be separated from the molecule of interest by a cleavage site to facilitate cleavage, so that after the molecule is purified, the tag can be easily removed.

Other fusion tags that could be included to facilitate purification of a molecule or construct of interest of use for embodiments disclosed herein can include, but are not limited to, staphylococcal protein A, streptococcal protein G, hexahistidine, calmodulin-binding peptides and maltose-binding protein (e.g. the latter is also useful to help ensure correct folding of a molecule of interest). Yet another selectable marker may include an antibiotic resistance gene. Other embodiments may include an antibiotic resistance gene. These genes have previously been utilized in the context of bicistronic vectors as the selection marker or HAT-based selectable bicistronic vector may be used.

Electrophoresis

Electrophoresis may be used to separate molecules (e.g. large molecules such as proteins or nucleic acids) based on their size and electrical charge. There are many variations of electrophoresis known in the art. A solution through which the molecules move may be free, usually in capillary tubes, or it may be embedded in a matrix. Common matrices include polyacrylamide gels, agarose gels, and filter paper.

Proteins, peptides and/or antibodies or antibody fragments thereof may be detected partially or wholly purified, or analyzed by any means known in the art. In certain embodiments, methods for separating and analyzing molecules may be used such as gel electrophoresis and elution or column chromatography or other separation/purification methods.

Any method known in the art for detecting, analyzing and/or measuring levels of antibodies or antibody fragments may be used in embodiments reported herein. For example, assays for antibodies or antibody fragments may include, but are not limited to, ELISA assays, chemiluminescence assays, flow cytometry, electroelution and other techniques known in the art.

Imaging Agents and Radioisotopes

In certain embodiments, the claimed proteins or peptides may be linked to a secondary binding ligand or to an enzyme (an enzyme tag) that will generate a fluorescent, a luminescent, or a colored product upon contact with a substrate. Examples of suitable enzymes include luciferase, green fluorescent protein, urease, alkaline phosphatase, (horseradish) hydrogen peroxidase and glucose oxidase. The use and identification of such labels is well known to those of skill in the art.

In other embodiments, labels or molecules capable of detecting peptides, antigens, constructs, antibodies or antibody fragments may include using aptamers. Methods for making and using aptamers are well known in the art and these methods and uses are contemplated herein. In addition, aptamers may be generated against construct elements disclosed herein and used for any purpose (e.g. purification, detection, modifying effects of the construct etc).

Some embodiments can include methods for detecting and/ or making polyclonal or monoclonal antibodies produced by a subject exposed to vaccine compositions disclosed in some embodiments of the present invention. For example, antibodies produced capable of inducing passive immunity to a subject may be isolated, analyzed and/or produced as a whole antibody or fragment thereof, or a polyclonal or a monoclonal antibody. Any means for producing or analyzing these antibodies or antibody fragments known in the art are contemplated.

Nucleic Acid Amplification

Nucleic acid sequences used as a template for amplification can be isolated from viruses, bacteria, cells or cellular components contained in the biological sample, according to standard methodologies. A nucleic acid sequence may be genomic DNA or fractionated or whole cell RNA. Where RNA is used, it may be desired to convert the RNA to a complementary cDNA. In one embodiment, the RNA is whole cell RNA and is used directly as the template for amplification. Any method known in the art for amplifying nucleic acid molecules are contemplated (e.g. PCR, LCR, Qbeta Replicase etc).

Expressed Proteins or Peptides

Genes can be expressed in any number of different recombinant DNA expression systems to generate large amounts of the polypeptide product, which can then be purified and used in methods and compositions reported herein. Any method known in the art for generating and using constructs is contemplated. In certain embodiments, genes or gene fragments encoding one or more polypeptide mays be inserted into an expression vector by standard cloning or subcloning techniques known in the art.

Some embodiments, using a gene or gene fragment encoding a polypeptide may be inserted into an expression vector by standard subcloning techniques. An expression vector may be used which produces the recombinant polypeptide as a fusion protein, allowing rapid affinity purification of a peptide or protein. Examples of such fusion protein expression systems are the glutathione S-transferase system (Pharmacia, Piscataway, N.J.), the maltose binding protein system (NEB, Beverley, Mass.), the FLAG system (MI, New Haven, Conn.), and the 6×His system (Qiagen, Chatsworth, Calif.).

Pharmaceutical Compositions and Routes of Administration

Aqueous compositions of some embodiments herein can include an effective amount of a therapeutic protein, peptide, construct, epitopic core region, stimulator, inhibitor, and the like, dissolved or dispersed in a pharmaceutically acceptable carrier or aqueous medium. Aqueous compositions of vectors expressing any of the foregoing are also contemplated. The phrases "pharmaceutically or pharmacologically acceptable" refer to molecular entities and compositions that do not produce an adverse, allergic or other untoward reaction when administered to an animal, or a human, as appropriate.

Aqueous compositions of some embodiments herein can include an effective amount of a therapeutic protein, peptide, construct, an effective amount of the compound, dissolved or dispersed in a pharmaceutically acceptable carrier or aqueous medium. Such compositions can also be referred to as inocula. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds or constructs will then generally be formulated for parenteral administration, e.g., formulated for injection via the intravenous, intramuscular, sub-cutaneous, intralesional, intranasal or even intraperitoneal routes. Any route used for vaccination or boost of a subject can be used. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Pharmaceutical forms suitable for injectable use can include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

If formulations or constructs disclosed herein are used as a therapeutic to boost an immune response in a subject, a therapeutic agent can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions can be prepared by incorporating the active compounds or constructs in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions can be administered in a manner compatible with the dosage formulation and in such amount as is therapeutically effective. The formulations are easily administered in a variety of dosage forms, such as the type of injectable solutions described above, but slow release capsules or microparticles and microspheres and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, intradermal, intranasal, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580).

The term "unit dose" refers to physically discrete units suitable for use in a subject, each unit containing a predetermined quantity of the construct composition or boost compositions calculated to produce desired responses, discussed above, in association with its administration, e.g., the appropriate route and treatment regimen. The quantity to be administered, both according to number of treatments or vaccinations and unit dose, depends on the subject to be treated, the state of the subject and the protection desired. The person responsible for administration will, in any event, determine the appropriate dose for the individual subject. For example, a subject may be administered a construct composition disclosed herein on a daily or weekly basis for a time period or on a monthly, bi-yearly or yearly basis depending on need or exposure to a pathogenic organism or to a condition in the subject (e.g. cancer).

The active therapeutic agents may be formulated within a mixture to comprise about 0.0001 to 1.0 milligrams, or about 0.001 to 0.1 milligrams, or about 0.1 to 1.0 or even about 10 milligrams per dose or so. Alternatively active agents (e.g. constructs) may be formulated to comprise a certain number of constructs per dose known to produce a desired effect in a subject. Multiple doses can also be administered.

In addition to the compounds formulated for parenteral administration, such as intravenous, intradermal or intramuscular injection, other pharmaceutically acceptable forms include, e.g., tablets or other solids for oral administration; liposomal formulations; time release capsules; biodegradable and any other form currently used.

One may also use intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and can include, for example, antibiotics and antihistamines and are used for asthma prophylaxis.

Additional formulations which are suitable for other modes of administration can include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

Kits

Further embodiments concerns kits for use with the methods and compositions described herein. Some embodiments concern kits having one or more vaccine or boost compositions of use to prevent or treat subjects having or exposed to a pathogen or have a condition. In certain embodiments, a pathogen can include a viral, bacterial, fungal, or protozoan derived pathogen. A condition can include a chronic condition or a condition like cancer. Other embodiments concern kits having vaccine compositions of use to prevent or treat subjects having or exposed to influenza or poxvirus. Kits can be portable, for example, able to be transported and used in remote areas. Other kits may be of use in a health facility to treat a subject having been exposed to a virus or suspected of being at risk of exposure to a pathogen (e.g. viral pathogen). Kits can include one or more construct compositions that can be administered before, during and/or after exposure to a pathogen. Other kits can include dehydrated formulations of constructs contemplated herein in order to prolong the half-life of the constructs (e.g. for stockpiling the vaccinations in the event of an outbreak or providing treatments to remote areas).

Other embodiments can concern kits for making and using molecular constructs described herein. In certain embodiments, compositions can include constructs having one or more of, attenuated or modified MVA and poxvirus secretory signals. Other constructs can also include at least one secretory signal sequence. Yet other embodiments can have a construct that includes translation control sequences (e.g. IRES). Other reagents for making and using constructs are contemplated.

Kits can also include a suitable container, for example, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the agent, composition and any other reagent containers in close confinement for commercial sale. Such containers may include injection or blow-molded plastic containers into which the desired vials are retained. Optionally, one or more additional agents such as other anti-viral agents, anti-fungal or anti-bacterial agents may be needed for compositions described, for example, for compositions of use as a vaccine.

Dose ranges used during vaccination can vary depending on the nature of the live attenuated vaccine and viral vector used. For recombinant poxviruses these doses can range between $10^5$-$10^7$ PFUs. In certain embodiments of the present invention, immunogenic doses can be as low as $10^2$ pfu. Frequency of vaccination can vary depending on the nature of the vaccine, the condition of the subject and also the route of administration used. One regimen can include a primary immunization (prime) followed up by a boost administration four to six weeks post-prime immunization. In certain embodiments of the present invention, improvements in antigen translation and expression can permit fewer and/or lower doses to be administered to a subject. Some embodiments concern intramuscular administration and/or intradermal vaccination of a subject.

Any method known to one skilled in the art may be used for large scale production of recombinant peptides or proteins. In accordance with these embodiments, large-scale production of MVA can be used. For example, master and working seed stocks may be prepared under GMP conditions in qualified primary CEFs. Cells may be plated on large surface area flasks, grown to near confluence and infected at selected MOI and vaccine virus purified. Cells may be harvested and intracellular virus released by mechanical disruption, cell debris removed by large-pore depth filtration and host cell DNA digested with endonuclease. Virus particles may be subsequently purified and concentrated by tangential-flow filtration, followed by diafiltration. The resulting concentrated bulk vaccine may be formulated by dilution with a buffer containing stabilizers, filled into vials, and lyophilized. For use, the lyophilized vaccine may be reconstituted by addition of diluent.

Poxviruses are known for their stability. The ability to lyophilize vaccinia for long term, room temperature storage and distribution was one of the key attributes that permitted widespread use of the vaccine and eradication of smallpox. Recently, it was demonstrated that Dryvax vaccinia virus stockpiled in the 60's was still potent after several decades. Procedures for lyophilization and storage of poxviruses are well know in the art and could be applied to the recombinant poxvirus vaccines for some embodiments disclosed herein.

The following examples are included to demonstrate certain embodiments presented herein. It should be appreciated by those of skill in the art that the techniques disclosed in the examples that follow represent techniques discovered to function well in the practices disclosed herein. However, those of skill in the art should, in light of the present disclosure, appreciate that many changes can be made in the certain embodiments which are disclosed and still obtain a like or similar result without departing from the spirit and scope herein.

EXAMPLES

Many constructs described herein were generated, separated and purified by methods disclosed herein (data not shown) for use in various studies. Some of these constructs are detailed in the descriptions below. In certain methods, constructs with and without influenza gene segments and peptides were generated and used in mouse models exposed to influenza challenges.

Example 1

Figure 1A:
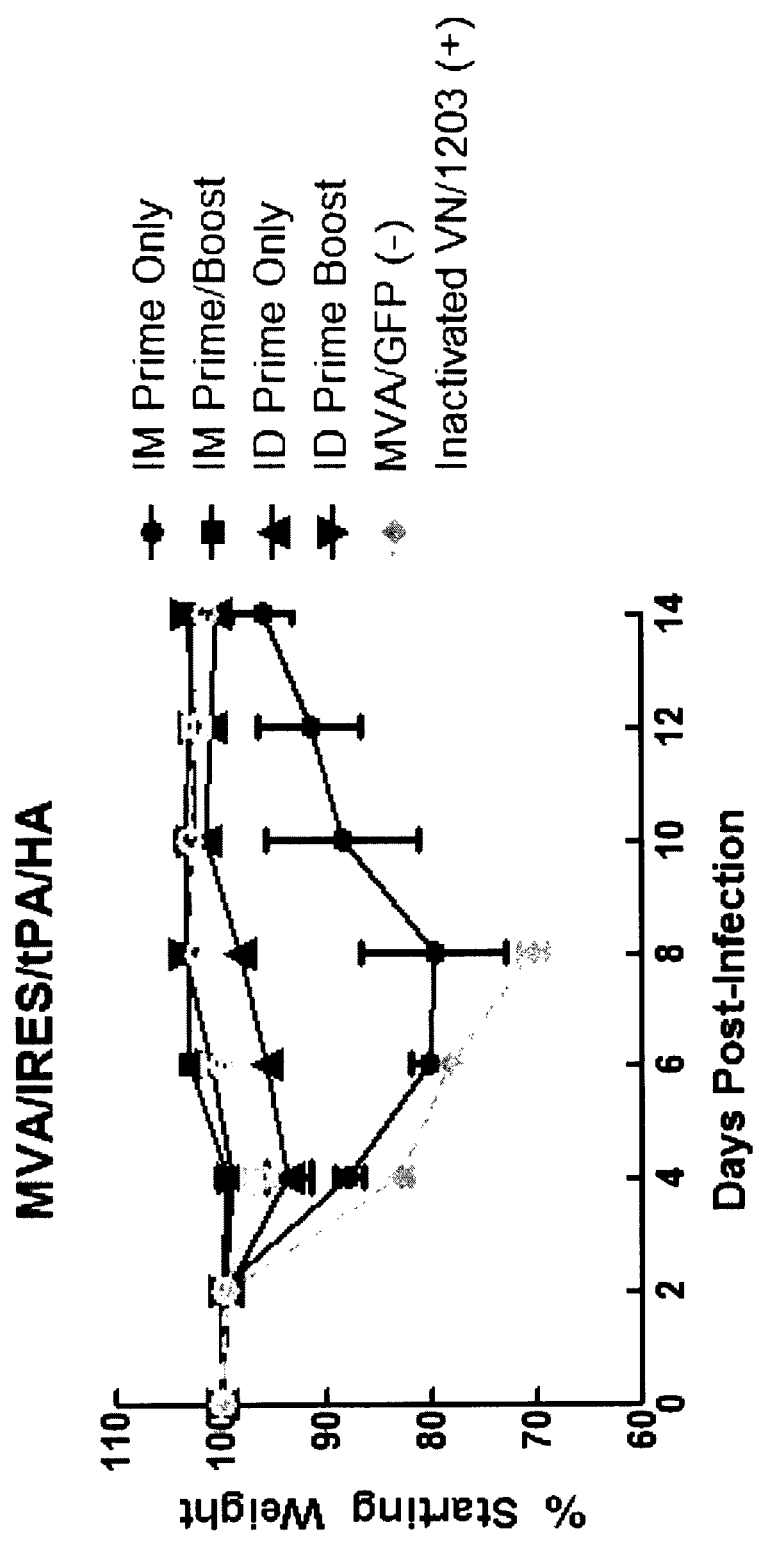
Figure 1B:
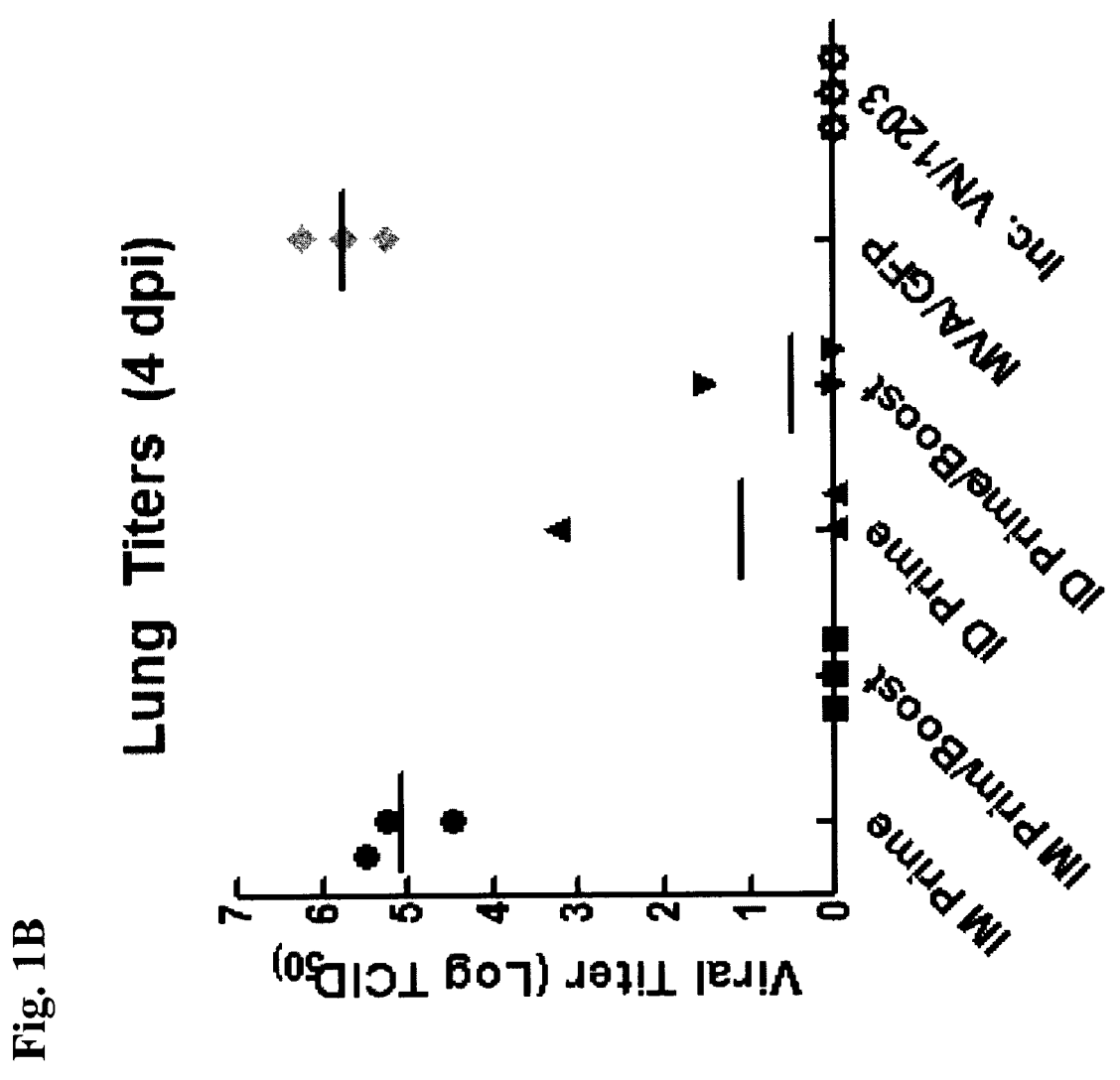

In one exemplary method, a construct composition including an influenza segment and a vaccinia secretory segment was tested for induction of immune protection against influenza challenge. FIGS. 1A and 1B illustrate a mouse model vaccinated and challenged with a virus. Here, Balb/C mice were vaccinated with MVA/IRES/tPA/HA (107 pfu) and challenged with VN/1203 63 (A/Vietnam/1203/04 (H5N1)-$10^4$ TCID$_{50}$) days post-vaccination. A) Weight loss, and B) Lungs titers, day 4 post-challenge. An MVA construct expressing an influenza segment elicited protection against the viral challenge. All the MVA vectored plague vaccines tested in this study were shown to be completely safe in severe combined immuno-deficient (SCID) mice. MVA has been stockpiled for use as a second-generation smallpox vaccine, with superior safety to the original live, attenuated vaccinia strains. Thus, a recombinant MVA/IRES/tPA/influenza segment vaccine has the potential to simultaneously provide protection against smallpox and influenza.

Example 2

Figure 2A:
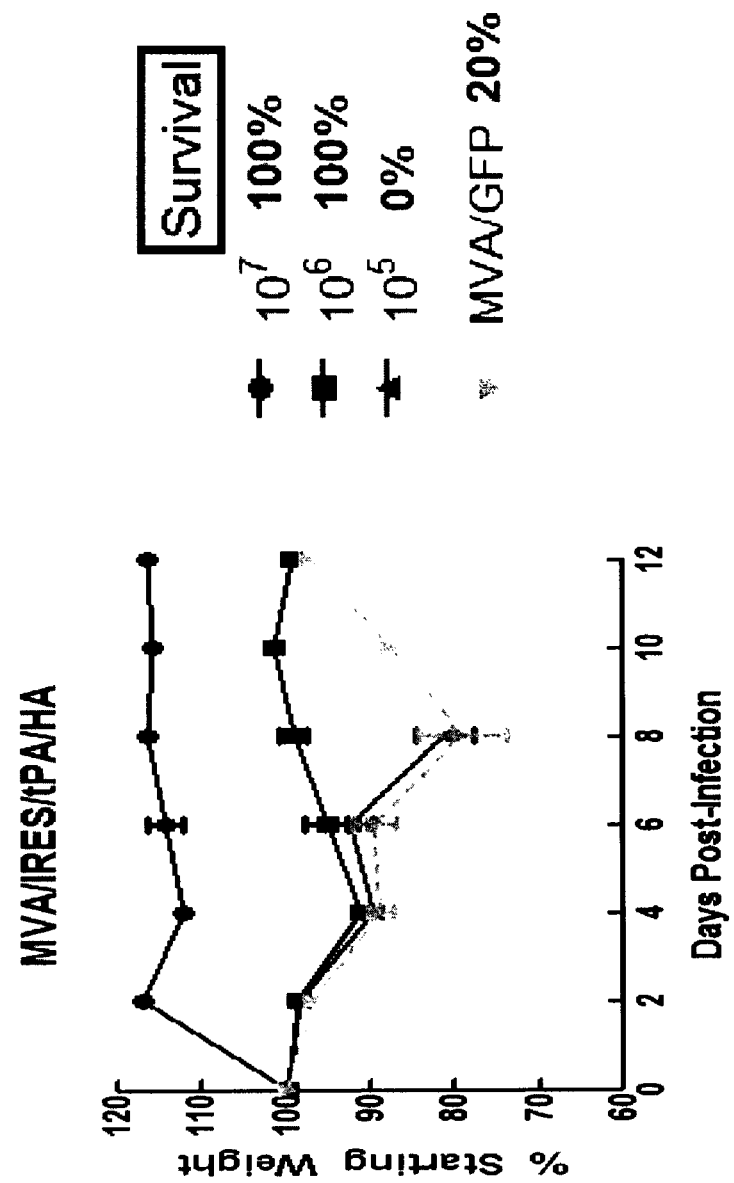
Figure 2B:
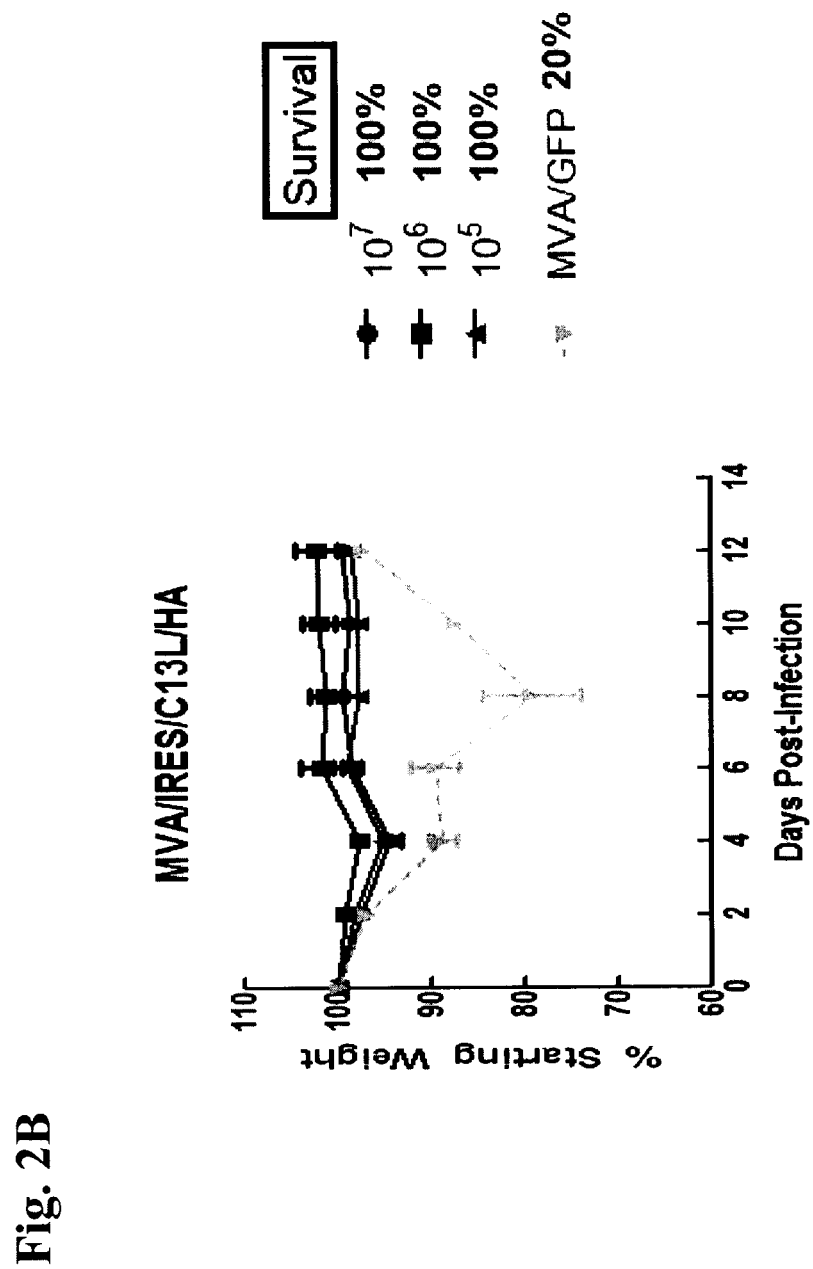
Figure 2C:
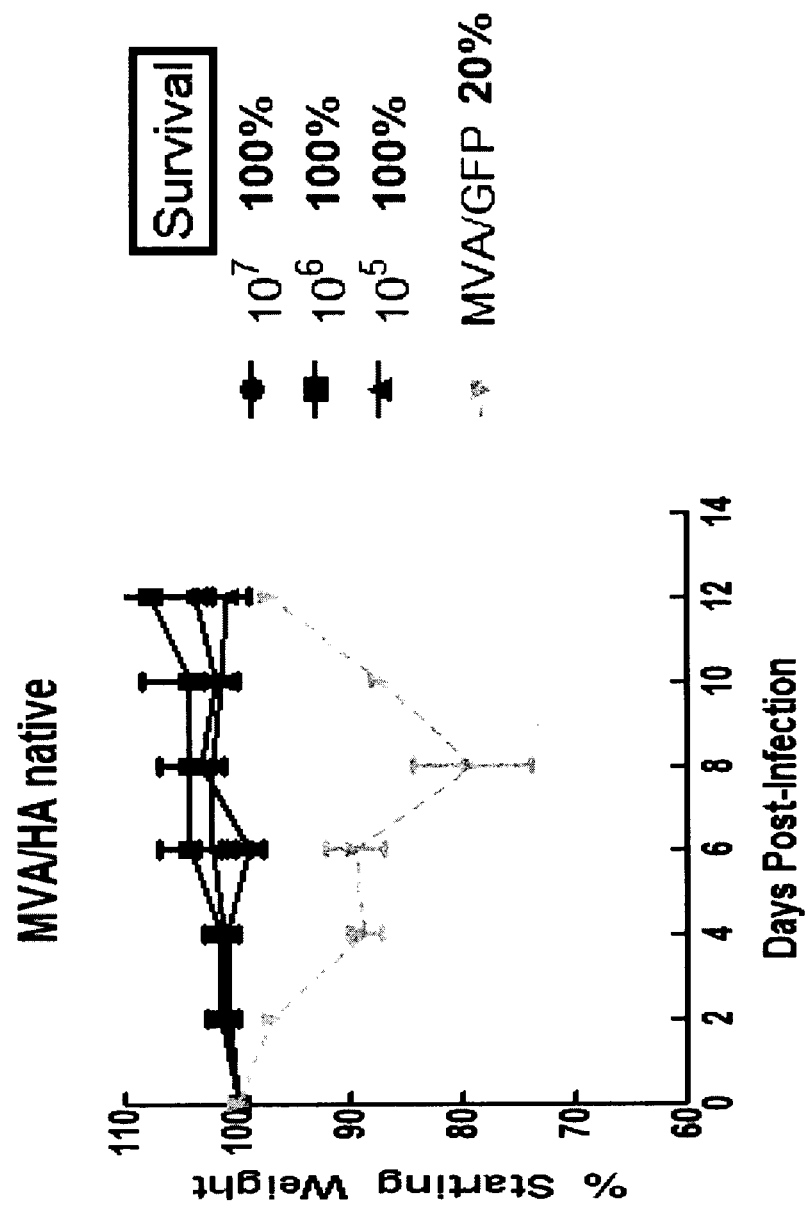

Dose Sparing: In another exemplary method, various constructs were tested in a range of doses to analyze their protective effects and to test some of the limitations in these dose ranges. FIGS. 2A-2C represents Balb/C mice (n=10) vaccinated ID with 105, 6 or 7 pfu and challenged with VN/1203 on day 63 post-vaccination. Weight loss curves are displayed for A) MVA/IRES/tPA/HA, B) MVA/IRES/C13L/HA, and C) MVA/HA native.

Example 3

Long-Term and Cross-Clade Protection

Figure 3:
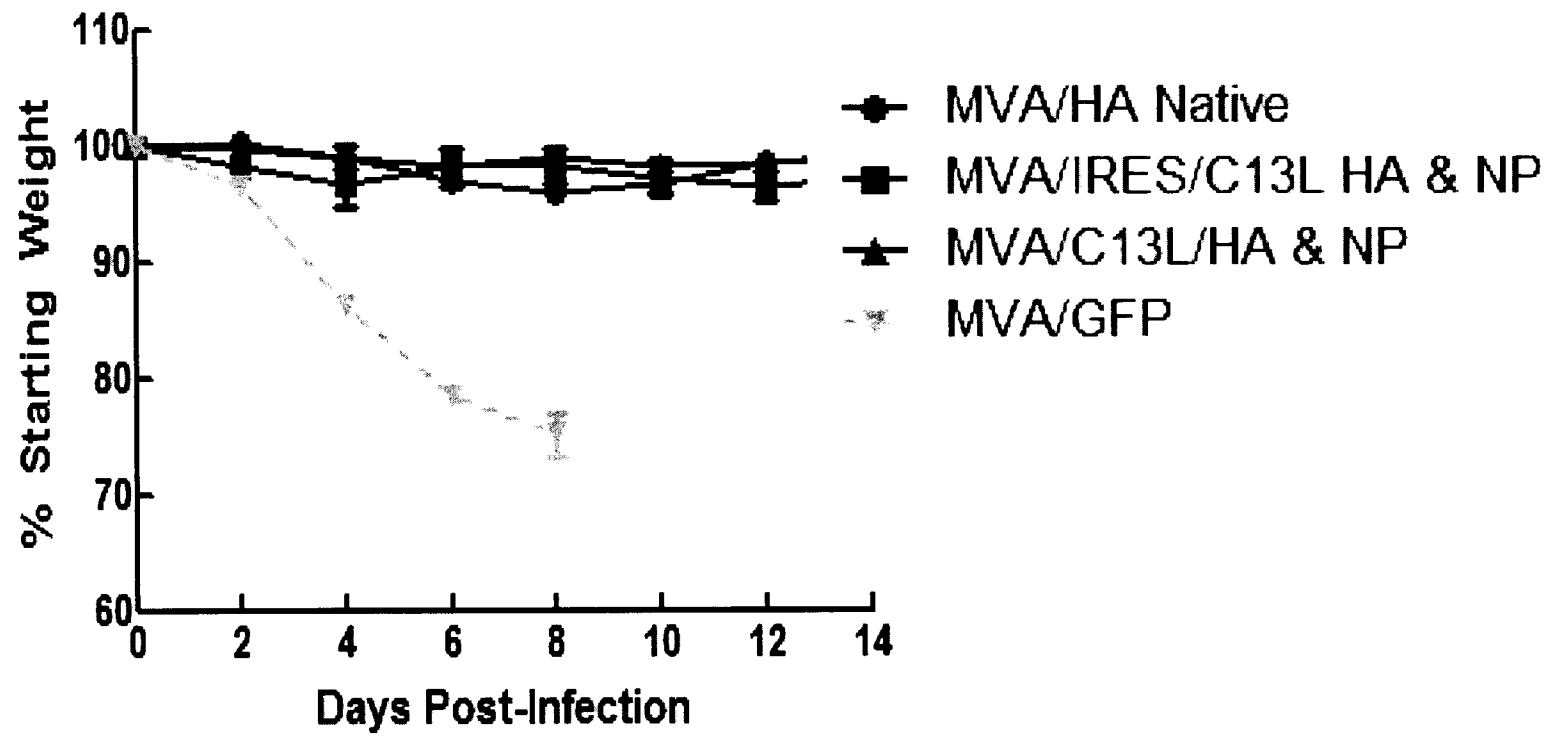

FIG. 3 illustrates that certain vaccine constructs presented herein provide long-Term Immunity. Balb/C mice (n=7) were intradermally (ID) vaccinated with 105 (HA) and/or 107 (NP) pfu and challenged with VN/1203 at 28 wks post-vaccination

Example 4

Figure 4:
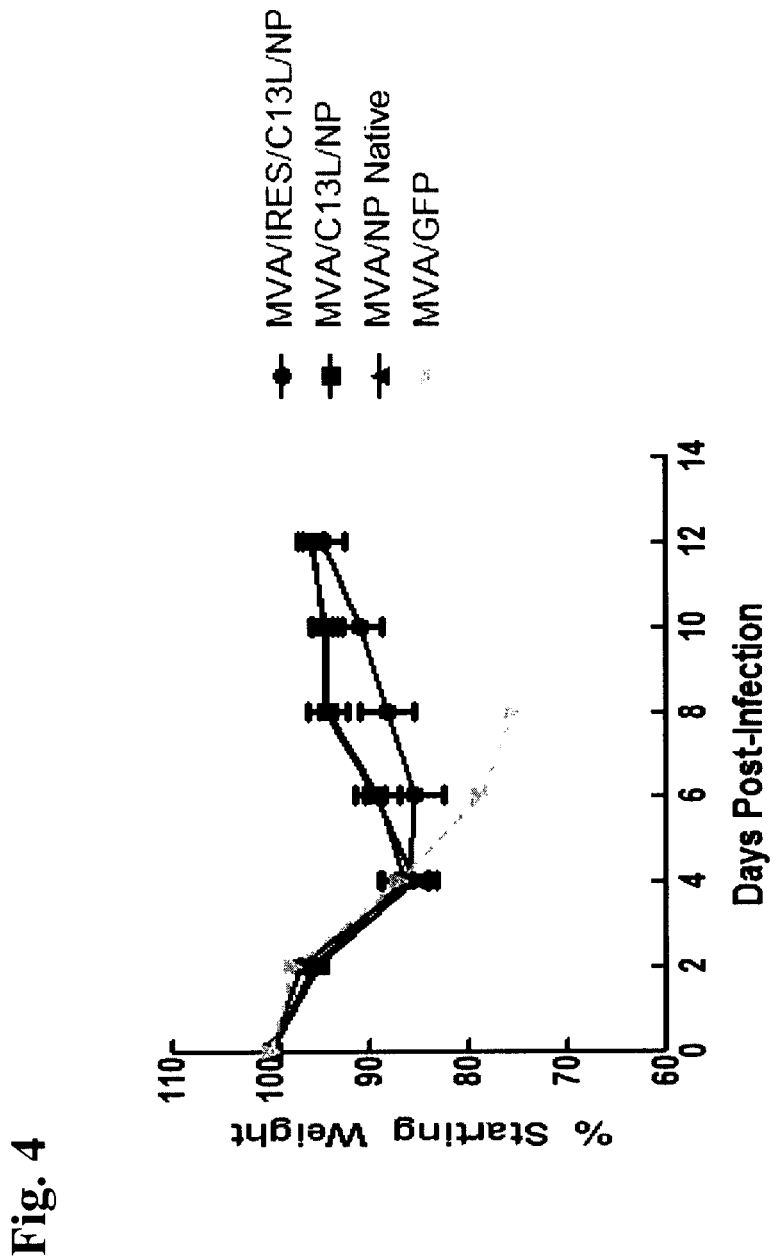

Heterologous Clade 2 Challenge:

FIG. 4 illustrates cross-clade protection. Here, Balb/C mice (n=7) ID were vaccinated with $10^5$ (HA) or $10^7$ (NP) pfu/mouse, and challenged with VN/UT 28 wks post-vaccination.

Safety

Figure 5:
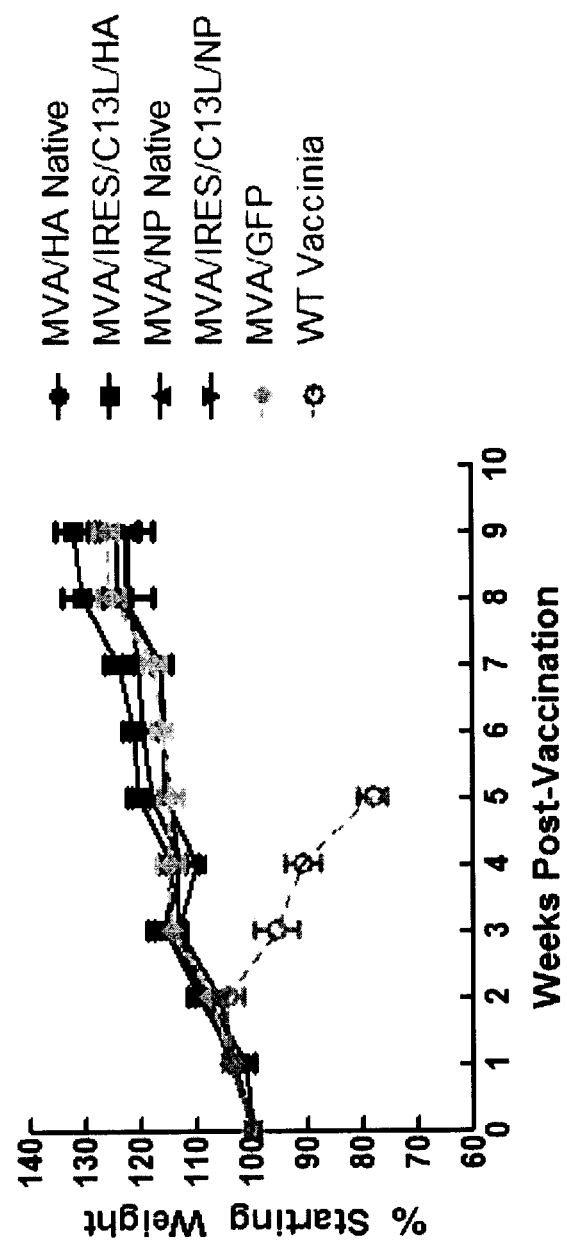
Figure 6A:
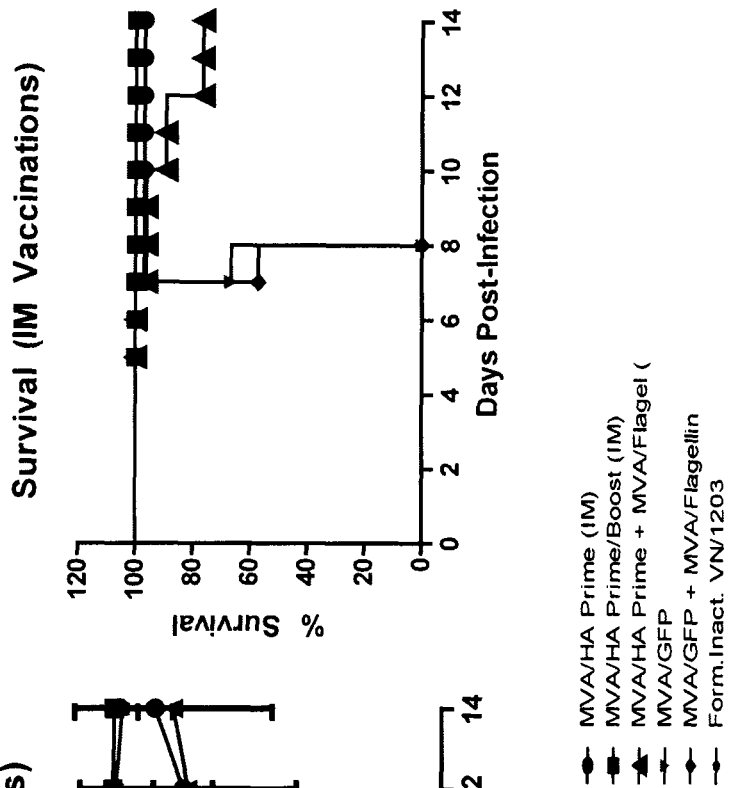
Figure 6B:
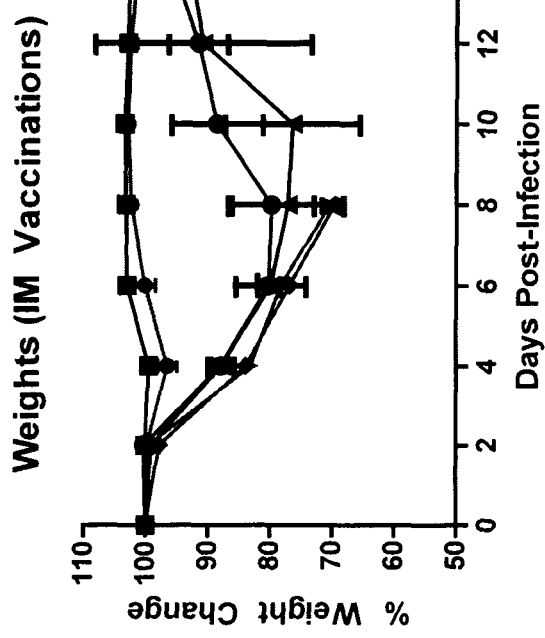
Figure 7B:
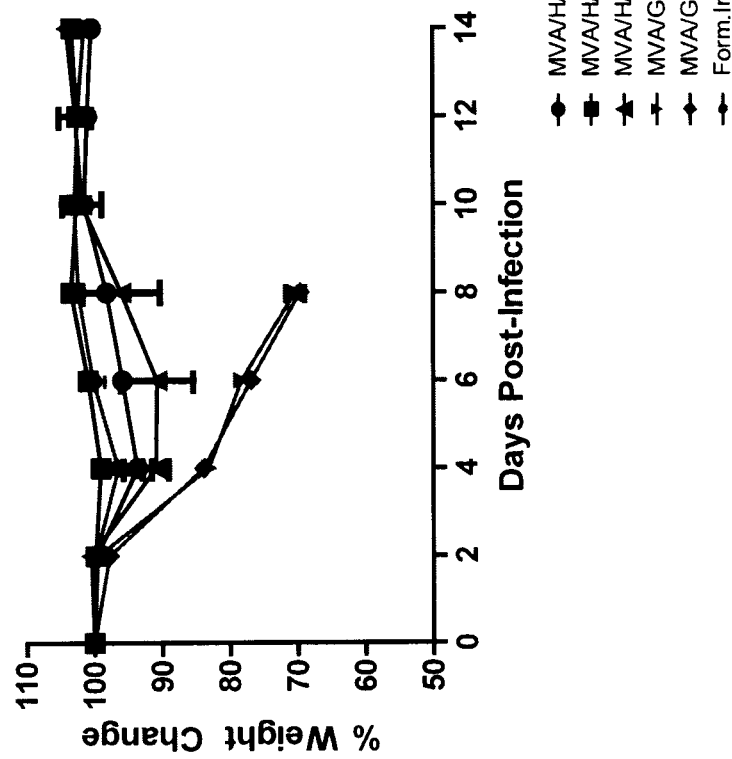
Figure 7A:
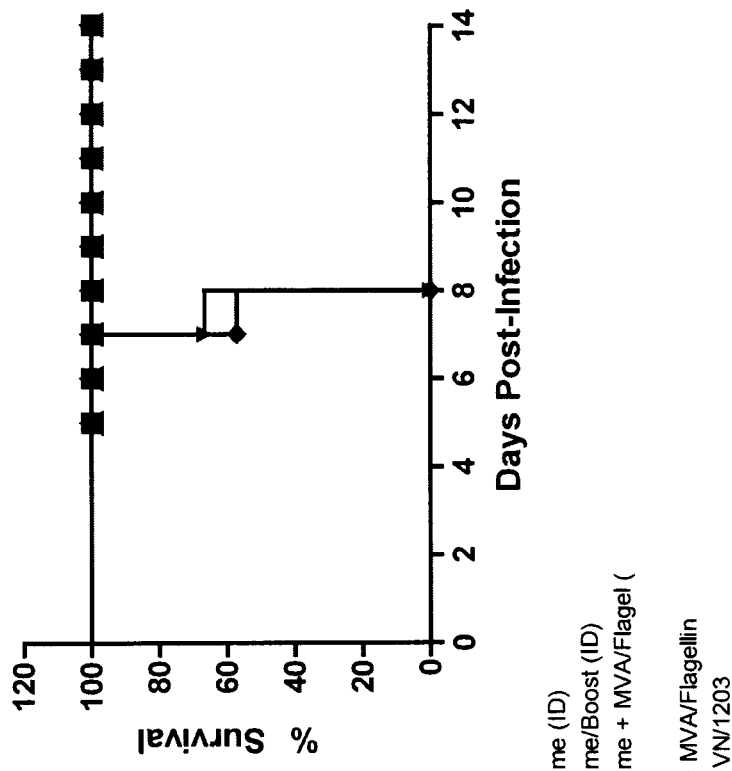
Figure 8B:
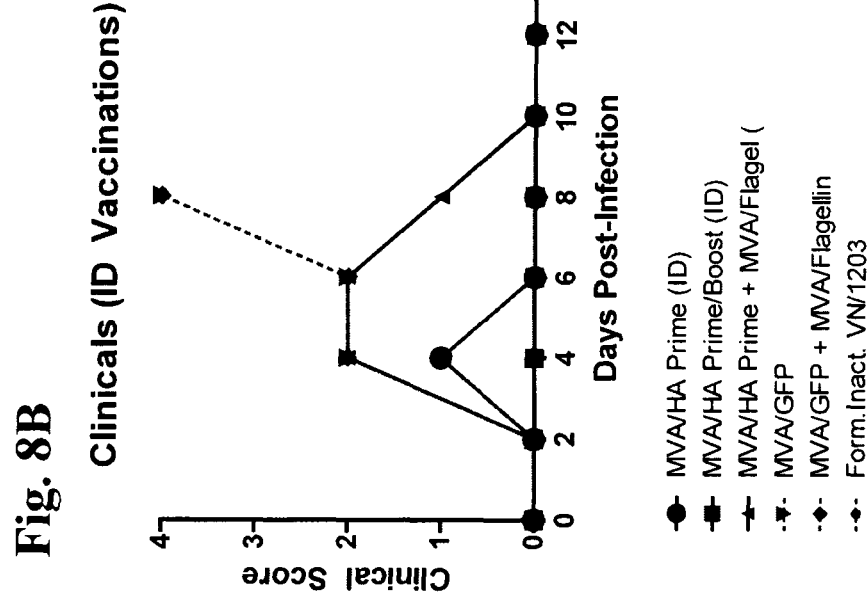
Figure 8A:
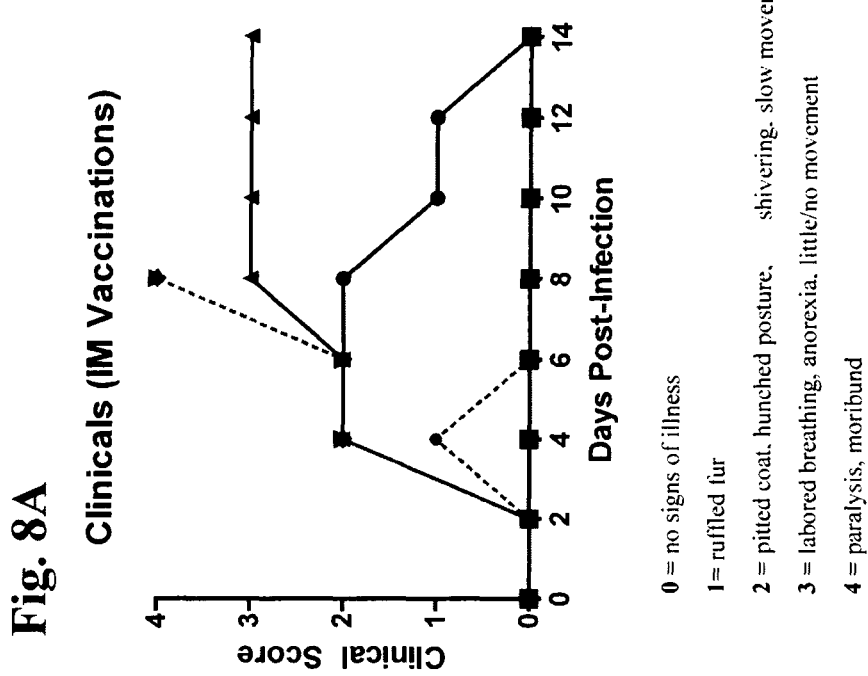
Figure 9:
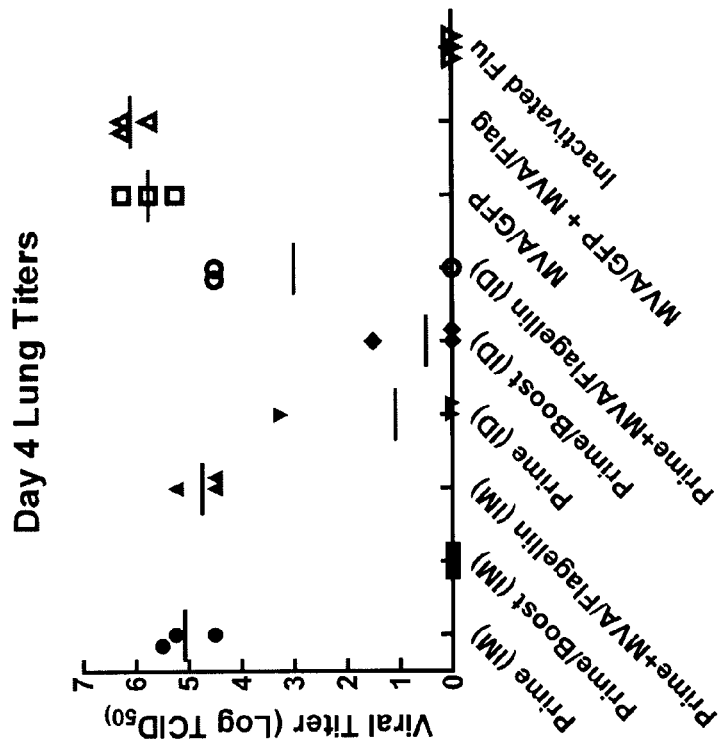
FIG. 9 represents an exemplary plot that illustrates viral titers in lung after introduction of various constructs of some embodiments described herein to the mice followed by challenge with influenza.

In another example, safeties of some of the vaccine constructs were assessed. FIG. 5 represents mice tested with certain constructs described herein. In this example, SCID/Balb/C mice (n=6) were IP inoculated with $10^8$ pfu/animal MVA-influenza constructs or $10^6$ pfu/animal Wild Type Vaccinia and monitored for morbidity and pox lesions for 6 weeks.

Experiments conducted in herein demonstrate that recombinant MVA influenza vaccines are safe & efficacious. It was demonstrated that single dose intradermal injection was able to provides 100% protection from lethal challenge. In addition, dose sparing introductions at about $5 \times 10^5$ offers 100% protection. In certain examples, protection was demonstrated to last up to 28 weeks. Other examples demonstrate that including NP in the constructs may provide cross-clade protection. Using a mouse model, it was demonstrated that recombinant MVA influenza vaccines are safe in SCID mice. These experiments demonstrate that MVA construct vaccinations may provide viable alternatives to traditional influenza vaccination, particularly for emerging virus subtypes.

B8R was used as a Vaccinia IFN-gamma soluble receptor. C13L is associated with a non-expressed protein in Vaccinia that may be a serpin homologue. As indicated these sequences are not present in MVA. The signal scores are equivalent or better than those for tPA. The scores are similar and not significantly different in the context of other antigens.

Putative Vaccinia signal sequences were analyzed and C13L signal was identified as a potent element for constructs generated and used herein. B8R signal could be more obvious as it is part of a known secreted Vaccinia protein.

Poxvirus Alternative Secretory Signals.

Alternative signal sequences from *orthopox* virus have been identified to replace tPA in certain constructs for example, for secretion enhancement from MVA. In this example, tPA cleavage site is correctly identified in F1 construct according to program signal P 3.0. Predicted cleavage after AG of NgoMIV site. Hidden Markov model (HMM) score of 98.8%.

Example 5

Exemplary Secretory Signal Sequences and Constructs
   Some Options for constructs are outlined below.
   C13L, exemplary secretory signal sequence
   i. VV-cop: 12510-12313 (complete DNA sequence: 12510-11971).
   ii. Unknown protein function. Located near serpin homologues.
   iii. VV-cop version has a deletion following the signal peptide that causes a frame shift and unrelated protein sequence prior to termination 44 aa later. The DNA sequence is present in comparison to *orthopox* orthologs. The last 100 bp are present at 179670-179767 as an inverted repeat. Full coding sequence equivalent to VV-WR, loci 206.
   iv. Secretory signal:

```
                                      (SEQ ID NO: 1)
     1. 1 MMIYGLIACLIFVTSSIA^SP 20
```

2. Signal peptide score=10.3, probability=$6.1 \times 10^{-5}$, VV-WR $1.1 \times 10^{-3}$.
   3. Cleavage in F1 either AGA-DL (neural network) or SIA-SPAGAD (HMM) with 99.8% signal probability.

B8R exemplary secretory signal sequence
i. VV-cop:
ii. IFN-gamma soluble receptor gene:
   1. B8R is secreted from the cell to bind host IFN-gamma.
   2. Secretory signal:

```
                                      (SEQ ID NO: 2)
     a.1 MRYIIILAVLFINSIHA^KI
``` b. Signal peptide score=10.5, probability=$4.1 \times 10^{-4}$
   3. Cleavage with F1 either KAG-ADL (neural network) or HA-KAGAD (HMM) with 99.1% signal probability.

Signal sequence design with and without IRES.
a. tPA without IRES.
b. With IRES, insert into XmaI site, not SalI site:
   i. C13L:

```
1) For, 5' IRES, Xma, tm = 64.7:
                                      (SEQ ID NO: 3)
a)    5' TCGTCCCGGGGTTATTTTCCACCATATTGCCGT 3'

2) Rev, 3' C13L-Ngom, tm = 64.7 with IRES
   sequences:
                                      (SEQ ID NO: 4)
a)    5'TCGTGCCGGCTGGACTAGCGATGGATGAAGTCACGAATATAAGA
      CACGCTATTAATCCGTATATCATCATATTATCATCGTGTTTTCAA
      AGGA 3'

3) pI41(pI4, C13L) created and annotated in CLC.
``` ii. B8R:

```
1) For, 5' IRES, Xma, tm = 64.7:
                                      (SEQ ID NO: 5)
a)    5' TCGTCCCGGGGTTATTTTCCACCATATTGCCGT 3'

2) Rev, 3' B8R-Ngom, tm = 64.7 with IRES
   sequence:
                                      (SEQ ID NO: 6)
a)    5'TCGTGCCGGCTTTAGCGTGTATACTATTAATGAACAAAAC
      TGCGAGAATTATAATATATCTCATATTATCATCGTGTTTTC
      AAAGGA 3'

3) pI42(pI4, C13L) created and annotated in CLC.
``` c. Without IRES:
   i. C13L

```
1) For: 5' C13L-Xma, Ngom, Nhe
                                      (SEQ ID NO: 7)
a)    5'CCGGGATGATGATATACGGATTAATAGCGTGTCTTATATTCGT
      GACTTCATCCATCGCTAGTCCAGCCGGCG 3'
```

-continued

```
2) Rev: 3' C13L-Xma, Ngom, Nhe
                                              (SEQ ID NO: 8);
a)    5'CTAGCGCCGGCTGGACTAGCGATGGATGAAGTCACGAATATA
      AGACACGCTATTAATCCGTATATCATCATC 3'

3) pI44(sel, C13L) created and annotated in CLC.
``` ii. B8R

```
1) For: 5' B8R-Xma, Ngom, Nhe
                                              (SEQ ID NO: 9)
a)    5'CCGGGATGAGATATATTATAATTCTCGCAGTTTTGTTCATTAA
      TAGTATACACGCTAAAGCCGGCG 3'

2) Rev: 3' B8R-Xma, Ngom, Nhe
                                              (SEQ ID NO: 10)
a)    5'CTAGCGCCGGCTTTAGCGTGTATACTATTAATGA
      ACAAAACTGCGAGAATTATAATATATCTCATC 3'

3) pI45(sel, B8R) created and annotated by CLC.
```

Materials and Methods

Construction of MVA Recombinant Vaccines

The transfer plasmid was used to generate recombinant MVA expressing influenza gene segments. Any method known in the art can be used to generate these constructs.

Some Construct Test Groups include the following in the presence or absence of various native and non-IRES constructs (e.g. IRES, tPA, C13L and B8R).

1. MVA/HA (IM) prime
2. MVA/HA (IM) prime/boost
3. MVA/HA (IM) prime+MVA/flagellin (Adjuvant)
4. MVA/HA (ID) prime
5. MVA/HA (ID) prime/boost
6. MVA/HA (ID) prime+MVA/flagellin (Adjuvant)
7. MVA/GFP prime/boost (IM)
8. MVA/GFP prime/boost (IM) flagellin
9. Formalin Inactivated VN/1203 5 μg (IM) prime/boost Some of these constructs have been generated in *E. coli*. Some constructs were expressed in CEF (chicken embryo fibroblasts, data not shown). Some constructs include one or more influenza gene segment(s) (e.g. HA, NA, NP, Hat, Some constructs include native or IRES or non-IRES constructs. Other constructs include native, C13L and IRES/C13L constructs with and without an pathogen associated gene segment.

Immunization and Challenge

Groups of mice (e.g. Harlan Sprague Dawley, Indianapolis, Ind.) received primary and booster immunizations with each vaccine candidate via intramuscular injections into hind legs. Then the mice were challenges with various viruses disclosed herein for protection.

Serology

Serum samples were collected post-primary vaccination and post-boost (pre-challenge) by means known in the art to assess antibody titers against influenza or poxvirus.

Statistical Analysis

The Student's t-test and the Logrank test were used to compare groups of data. Probability values<0.05 were considered significant using the GraphPad Prism 5 software (La Jolla, Calif.) for all statistical analyses.

Possible Secretory Signal Sequences of Use for Constructs Disclosed Herein

| VV-cop | |
|---|---|
| have SSP | IN MVA |
| A13L | |
| A14L | |
| A39R | |
| A41L | |
| A56R | yes |
| B19R | no |
| B25R | |
| B5R | |
| B7R | |
| B8R | no |
| B9R | |
| C11R | yes |
| C13L | no |
| C19L | no |
| C3L | |
| F5L | |
| G3L | |
| K2L | |
| M2L | no |

In certain experiments it was noted that IM vaccinations such as Prime/Boost scheme were very effective, that there was increased morbidity with prime only. An adjuvant may not be effective and that in certain experiments it was observed that there was an increase in morbidity & mortality with the flagellin. In other experiments, ID Vaccinations using all tested schemes provide complete protection with the least morbidity occurring with prime/boost. An adjuvant was not contributing and adjuvant alone does not provide protection.

Some dose ranges were tested in a mouse model for certain constructs disclosed herein. Some of the doses ranges were about $5\times10^5$ to about $5\times10^7$. Weight loss of test animals was one way to monitor effectiveness of vaccination formulations and constructs tested.

FIGS. 6A and 6B represent exemplary plots of parameters in mice after intramuscular (IM) introduction of various constructs of some embodiments described herein to the mice followed by challenge with influenza, A) Weight loss and B) Survival post-challenge.

FIGS. 7A and 7B represent exemplary plots of parameters in mice after intradermal (ID) introduction of various constructs of some embodiments described herein to the mice followed by challenge with influenza, A) Weight loss and B) Survival post-challenge/infection.

FIGS. 8A and 8B represent exemplary plots of parameters in mice after (A) intramuscular (IM) or (B) intradermal (ID) introduction of various constructs of some embodiments described herein to the mice followed by challenge with influenza. These exemplary experiments assess several clinical indications. The indications were graded in the mouse model on a scale of 0 to 4. 0=no signs of illness, 1=ruffled fur; 2=pitted coat, hunched posture, shivering and slow movement; 3=labored breathing, anorexia, little/no movement and 4=paralysis, moribund.

FIG. 9 represents an exemplary plot that illustrates viral titers in lung after introduction of various constructs of some embodiments described herein to the mice followed by challenge with influenza. Mice were sacrificed in each group on day 4 (post challenge/infection, 3 mice per group) and lungs were homogenized and tittered on MDCKs. Log virus titer is presented.

Table 1 represents some of the MVA influenza transfer vectors and constructs generated and tested.

Figure 10A:
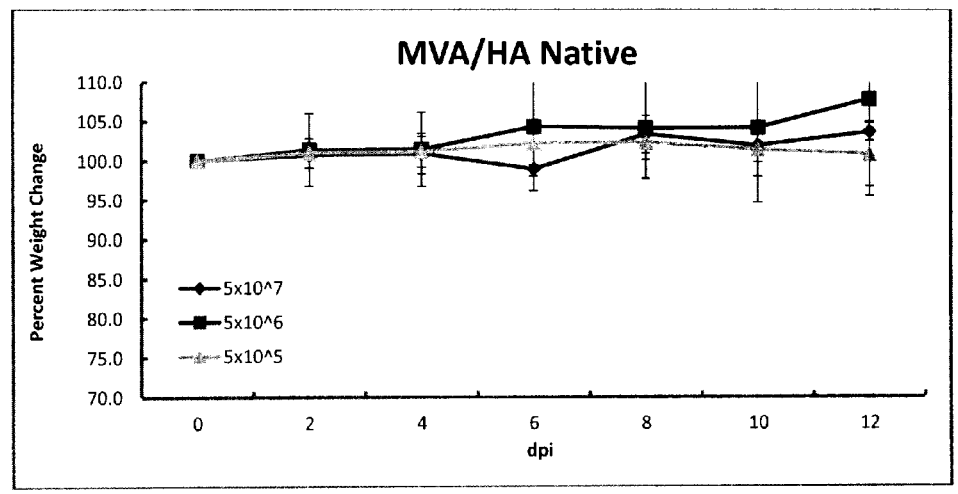
FIGS. 10A and 10B represent exemplary plots of percent weight change in mice after introduction of 2 different constructs of some embodiments described herein having the HA gene segment in each construct followed by challenge with influenza.
Figure 10B:
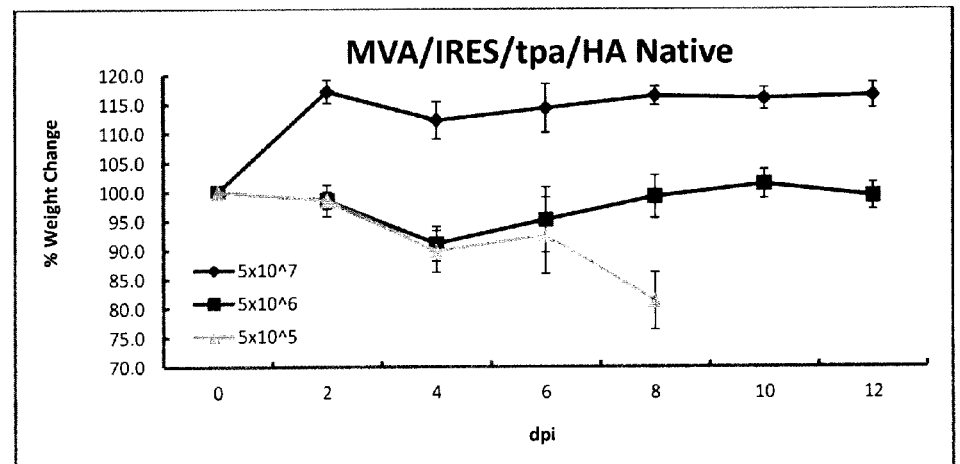

FIGS. 10A and 10B represent exemplary plots of percent weight change in mice after introduction of 2 different constructs of some embodiments described herein having the HA gene segment in each construct followed by challenge with influenza. These construct were administered at different doses ($5\times10^5$ to $5\times10^7$)

FIGS. 11A and 11B represent exemplary plots of percent weight change in mice after introduction of 2 different constructs of some embodiments described herein followed by challenge with influenza. In A), these construct were administered at different doses (5×105 to 5×107). In B. a traceable compound was linked to an MVA construct.

FIGS. 12A and 12B represent exemplary plots of percent weight change in mice after introduction of 2 different constructs at various concentrations of some embodiments described herein followed by challenge with influenza. These construct were administered at different doses (5×105 to 5×107).

Figure 13A:
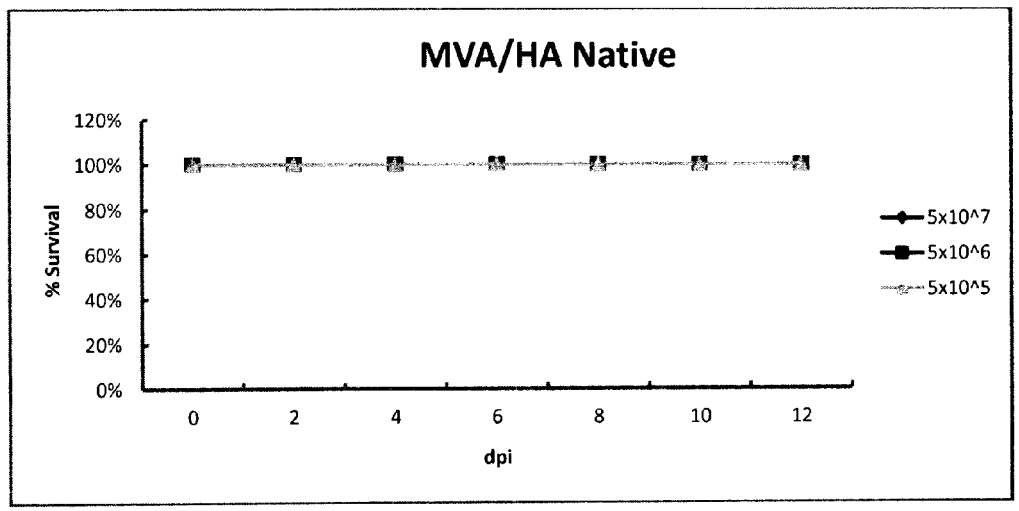
FIGS. 13A and 13B represent exemplary plots of survival in mice after introduction of 2 different constructs at various concentrations of some embodiments described herein followed by challenge with influenza.
Figure 13B:
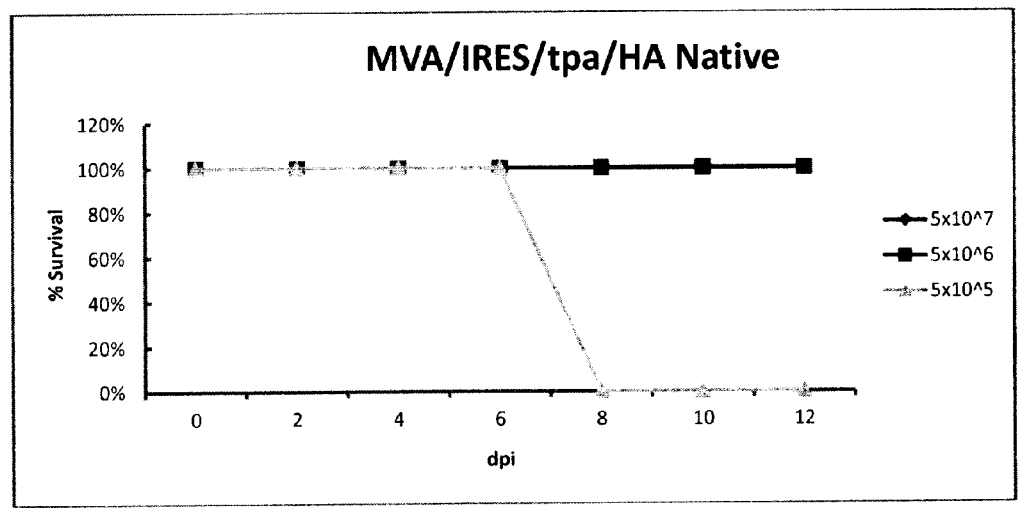

FIGS. 13A and 13B represent exemplary plots of percent survival in mice after introduction of 2 different constructs at various concentrations of some embodiments described herein followed by challenge with influenza. These construct were administered at different doses (5×105 to 5×107). Some of the constructs included additional elements, tPA and IRES. It was observed at day 8 that mice having constructs with an IRES and tPA element had decreased survival than MVA/HA alone in a construct.

Figure 14A:
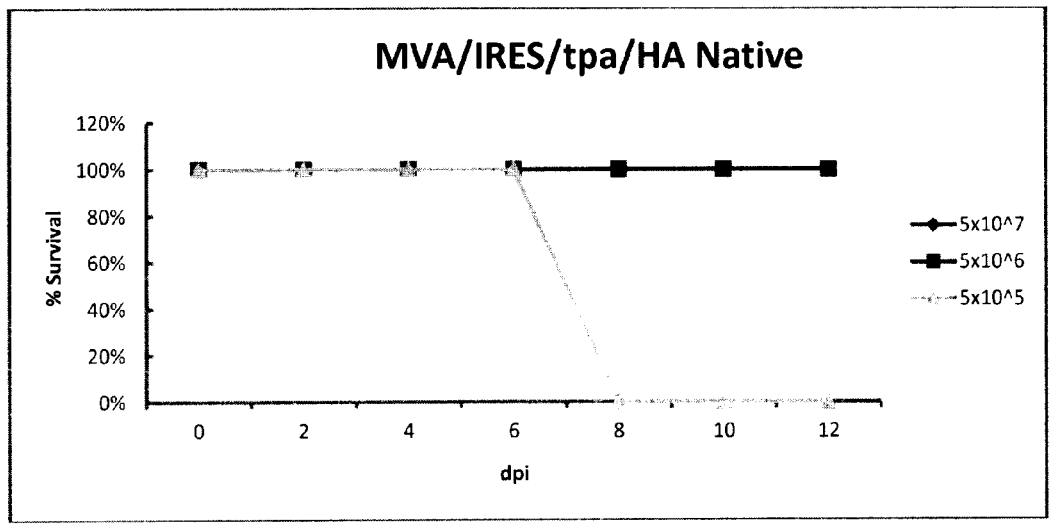
FIGS. 14A and 14B represent exemplary plots of survival in mice after introduction of 2 different constructs at various concentrations of some embodiments described herein followed by challenge with influenza.
Figure 14B:
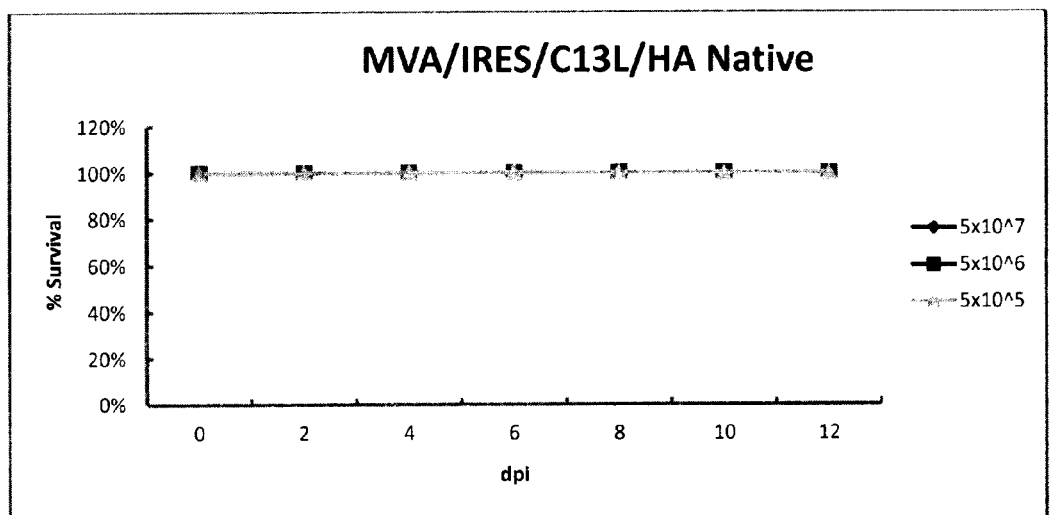

FIGS. 14A and 14B represent exemplary plots of survival in mice after introduction of 2 different constructs at various concentrations of some embodiments described herein followed by challenge with influenza. These construct were administered at different doses (5×105 to 5×107). Some of the constructs included additional elements, tPA and IRES sequences (A). It was observed at day 8 that mice having constructs with an IRES and tpa element had decreased survival than MVA/HA alone in a construct. When the tPA element was replaced with another secretory signal C13L, survival was 100 percent for the time period tested.

FIGS. 15A and 15B represent exemplary plots of survival in mice after introduction of 2 different constructs at various concentrations of some embodiments described herein followed by challenge with influenza (dpi represents days post infection). These construct were administered at different doses (5×105 to 5×107).

Figure 16A:
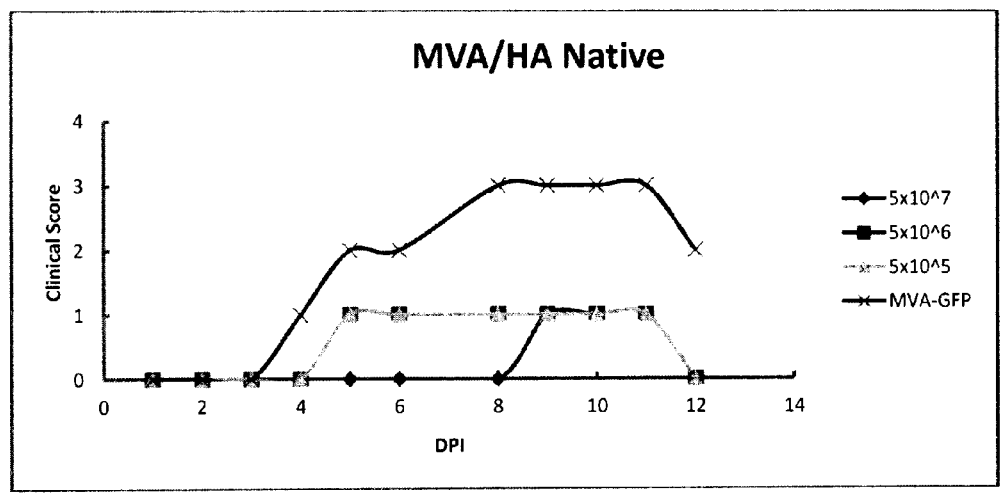
FIGS. 16A and 16B represent exemplary plots of clinical scores (e.g. physical and physiological parameters) in mice after introduction of 2 different constructs at various concentrations of some embodiments described herein followed by challenge with influenza.
Figure 16B:
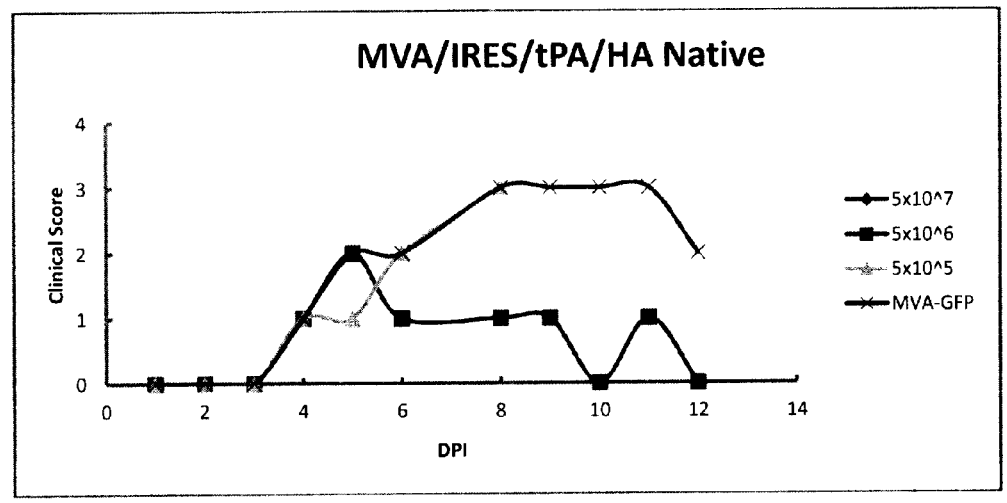

FIGS. 16A and 16B represent exemplary plots of clinical scores (e.g. physical and physiological parameters, see above scores from 0 to 4) in mice after introduction of 2 different constructs at various concentrations of some embodiments described herein followed by challenge with influenza. These construct were administered at different doses (5×105 to 5×107). In addition an MVA construct linked to a detectible marker was also introduced and followed in the mice.

Figures 17A, 17B:
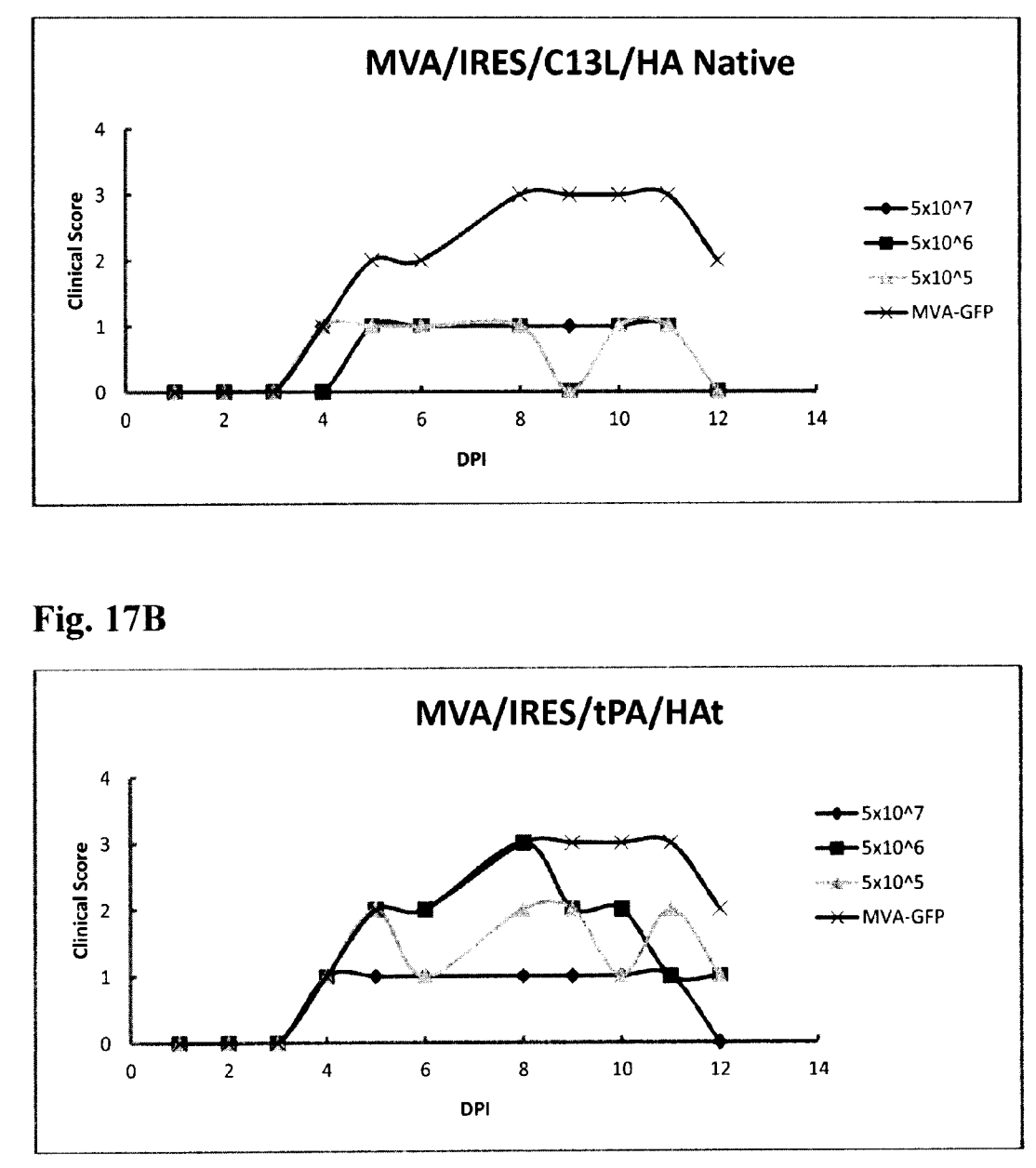

FIGS. 17A and 17B represent exemplary plots of clinical scores (e.g. physical and physiological parameters) in mice after introduction of 2 different constructs at various concentrations of some embodiments described herein followed by challenge with influenza. These construct were administered at different doses (5×105 to 5×107). In addition an MVA construct linked to a detectible marker (GFP) was also introduced and followed in the mice.

Figure 18:
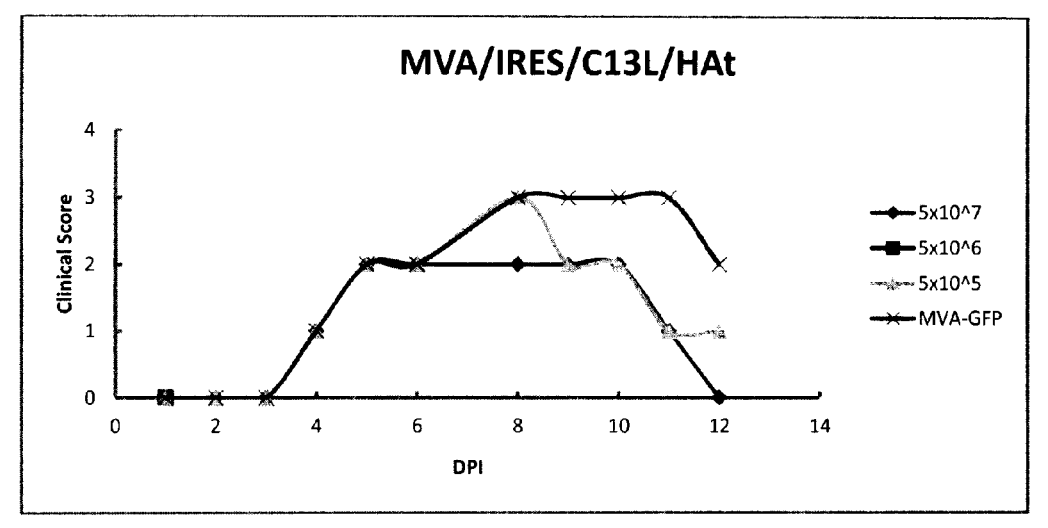

FIG. 18 represents an exemplary plot of clinical scores (e.g. physical and physiological parameters) in mice after introduction of a construct at various concentrations of some embodiments described herein followed by challenge with influenza. These construct were administered at different doses (5×105 to 5×107). In addition an MVA construct linked to a detectible marker (GFP) was also introduced and followed in the mice.

Example 6

Groups of mice (n=8) were inoculated intradermally with modified vaccinia Ankara (MVA) three month prior to intradermal vaccination with MVA/flu vaccines expressing hemagglutinin and/or nucleoprotein in with or without secretory signal (C13L).

TABLE 2 represents Antibody titers (Geometric mean titer—GMT) of serum samples following prime and booster (intradermal) vaccination with MVA/influenza vaccines in mice with pre-existing immunity to vaccinia:

| Vaccine Construct | Sampling | |
|---|---|---|
| | Pre-Boost | Post-Boost |
| MVA/HA | $3.61^c$ | $697.92^a$ |
| MVA/C13L/HA | $1.00^c$ | $65.42^b$ |
| MVA/C13L/NP | $1.00^c$ | $1.00^c$ |
| MVA/HA/C13L/NP | $2.11^c$ | $697.92^a$ |
| MVA/GFP | $1.00^c$ | $1.00^c$ |

$^{a-e}$groups with different letters differ significantly (P < 0.05) by ANOVA

Figure 19A:
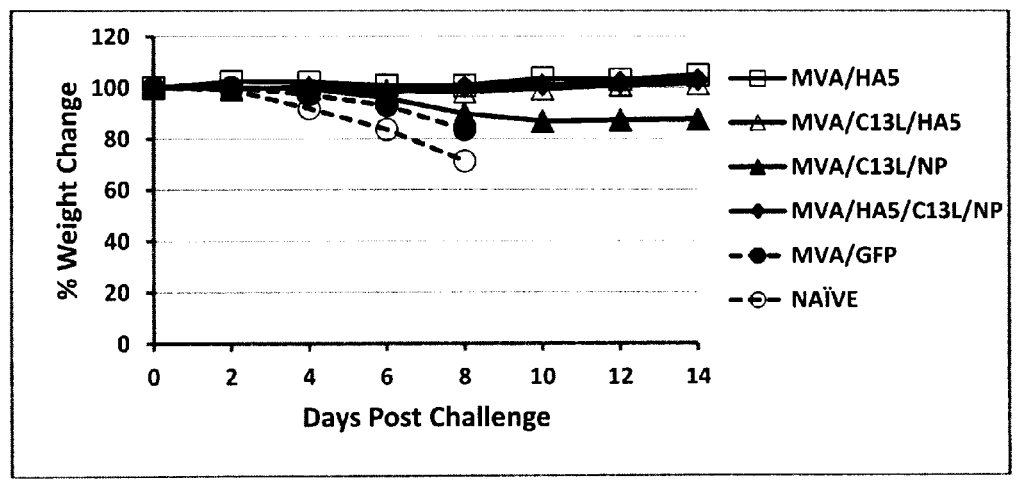
FIGS. 19A and 19B represent exemplary plots of percent weight change (FIG. 19A) and assessed clinical scores (FIG. 19B) in mice after introduction of different constructs in mice pre-exposed to vaccinia followed by challenge with influenza.
Figure 19B:
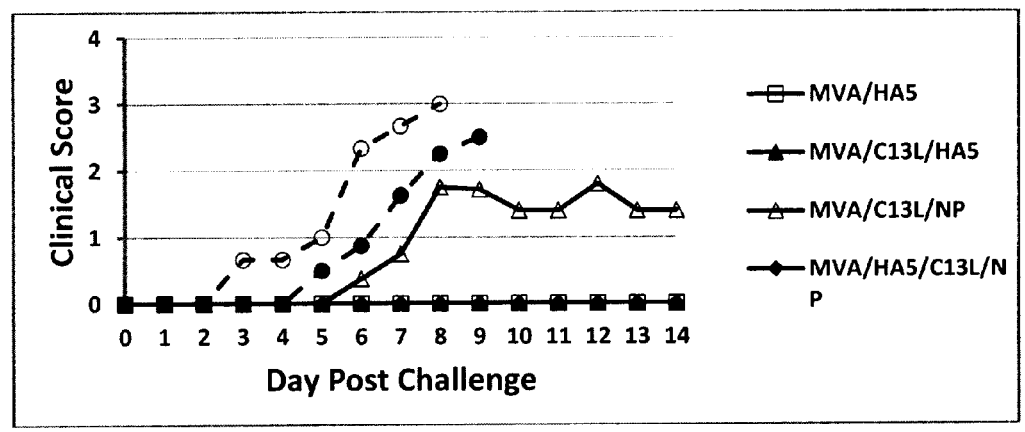
Figure 20:
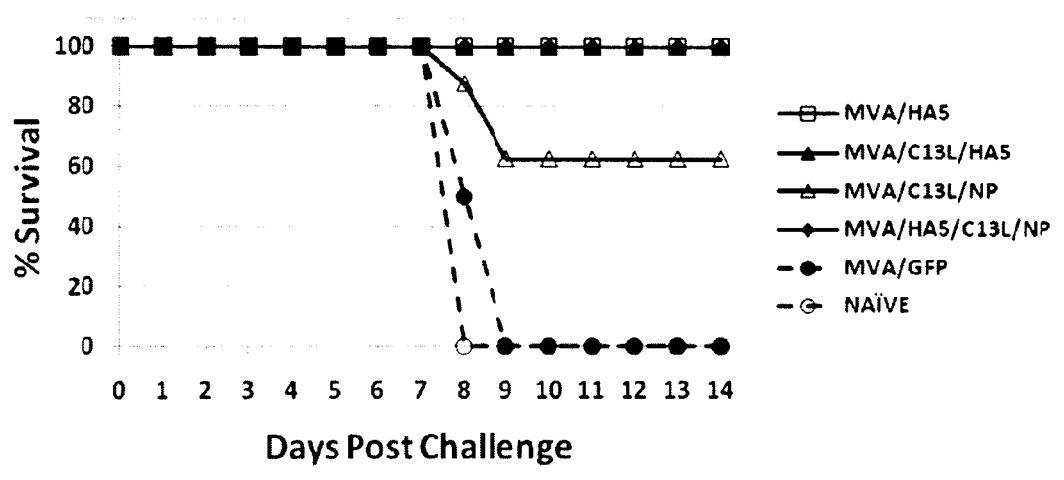

FIGS. 19A and 19B represent (A) mean weigh changes in immunized mice challenged with Influenza A/Vietnam/1203-H5N1 virus ($10^4$ $TCID_{50}$) 4 wks post-booster vaccination with MVA/Flu vaccines. Mice had pre-existing immunity to vaccinia. Mice immunized with MVA/Flu containing the hemagglutinin antigen did not lose weight; and (B) represents Clinical score of mice challenged with Influenza A/Vietnam/1203-H5N1 virus ($10^4$ $TCID_{50}$) 4 wks post-booster vaccination with MVA/Flu vaccines. Mice had pre-existing immunity to vaccinia prior to immunization of MVA/Flu vaccines. Clinical scores 0-4 are detailed above FIG. 20 represents survival rates of immunized mice (using the same constructs as in FIGS. 19A and B above) challenged with Influenza A/Vietnam/1203-H5N1 virus (104 TCID50) 4 wks post-booster vaccination with MVA/Flu vaccines. Mice had pre-existing immunity to vaccinia prior to immunization of MVA/Flu vaccines. All mice immunized with MVA/Flu containing the hemagglutinin antigen survived challenge with lethal dose of Influenza A/Vietnam/1203-H5N1 virus.

Example 7

In Vitro Expression of Influenza Virus Proteins by MVA/Flu Viruses

Figure 21:
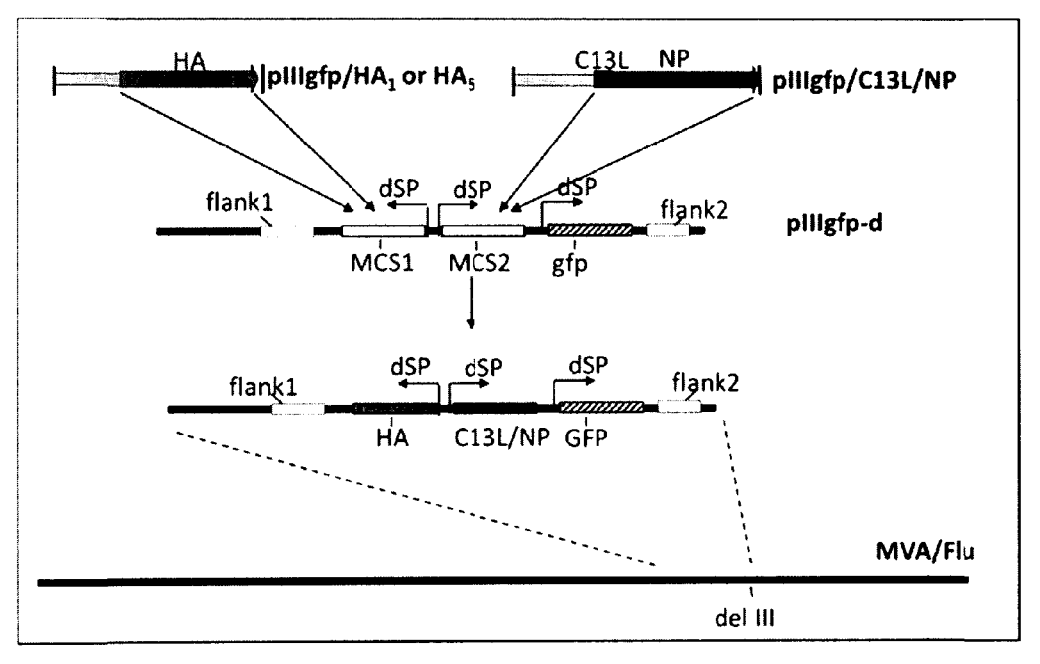

FIG. 21 represents a schematic construct of having two influenza gene segments from different subtypes each having a secretory signal associated with the gene segment. In certain examples, the secretory signal can be naturally occurring and in other examples it can be inserted next to or fused to the influenza gene segment, or a combination thereof.

In one exemplary method, expression levels of the HA1, HA5 and NP antigens of influenza virus were assessed by immunoblot analyses of proteins from CEF cells infected with the MVA/Flu recombinant viruses. Expression levels were evaluated in whole cell extracts and in cell culture supernatants 48 hr post-infection (FIG. 22). Both HA1 and HA5 proteins were detected (based on their predicted sizes) in whole cell extract (FIGS. 22Ai and 22Aii, FIGS. 22Bi and 22Bii) as well as in the culture supernatant (FIGS. 22Bi and 22Bii). To facilitate secretion of NP into the culture supernatant the C13L secretory signal sequence was fused to the 5' end of the NP protein. As illustrated in FIG. 22C NP expression was detected in both cellular and supernatant fractions from cells infected with the MVA/C13L/NP virus. The native NP protein had the expected molecular weight of 56 kD (FIG. 22C). In contrast, the C13L/NP fusion protein appears slightly larger than the native NP suggesting that the signal peptide is not cleaved upon expression or secretion (FIG. 22C). Results indicate that the C13L secretory signal increases NP secretion into the culture supernatant as compared to the native NP construct. As with the single antigen constructs, recombinant viruses expressing both HA and NP proteins (MVA/HA1/C13L/NP and MVA/HA5/C13L/NP) demonstrated increased levels of NP protein in cellular fractions than the supernatant fraction (data not shown).

Example 8

Efficacy of a Single Dose of MVA/Flu Vaccine Against Homologous Challenge

In another exemplary methods, groups of BALB/c mice (n=10) were vaccinated ID (intradermally) with a single dose of MVA/HA1 or MVA/HA5 recombinant vaccine and challenged by the IN route eight weeks later. Antibody titers were measured by hemagglutination Inhibition (HI) assays against A/Norway/3487-2/09(NW/09) or A/Vietnam/1203/04 (VN/1203), respectively and survival rates following challenge recorded. The vaccines elicited significantly higher ($P \leq 0.05$) HI titers (FIGS. 23A and 23B) compared to the control virus (MVA/GFP) and conferred complete protection against homologous challenge with NW/09 or VN/1203, respectively (FIGS. 23C and 23D). Although one out of three mice vaccinated with a single dose of MVA/HA1 or MVA/HA5 showed high titers of virus in their lungs on day 3 post challenge, the overall viral loads in the lungs of immunized mice were significantly lower ($p<0.05$) compared to those from MVA/GFP immunized mice (FIGS. 23E and 23F). Furthermore, mice receiving a prime and boost immunization with MVA/Flu vaccine in subsequent studies, cleared the virus from their lungs three days post-challenge (FIG. 24). Mice in the control group lost weight and were humanely euthanized when they reached 20% weight loss. No significant ($P>0.05$) weight losses were recorded in animals that received any of the MVA/Flu vaccines (MVA/HA1 or MVA/HA5) upon challenge with NW/09 or VN/1203, respectively (FIGS. 23G and 23H). In an ancillary long-term immunity study, mice were immunized with a single dose of MVA/HA5 and seven months later they were challenged with a lethal dose of VN/1203. All vaccinated animals were protected while control animals succumbed to challenge with a median survival day of seven.

Example 9

Cross-Protective Immunity of MVA/Flu Vaccines

In yet another exemplary method, cross-protective efficacy of MVA/Flu vaccines expressing for example, both HA and NP influenza proteins (MVA/HA1/C13L/NP and MVA/HA5/C13L/NP) were tested against IN challenge with 100 LD50 of the H5N1 strain A/Vietnam/1203/04 (VN/1203) ($1 \times 10^4$ pfu), the H1N1 pandemic strain A/Norway/3487-2/09 (NW/09) ($1.0 \times 10^6$ pfu), the H1N1 seasonal strain A/Puerto Rico/8/34 (PR8) ($3.99 \times 10^5$ pfu) or the H3N2 seasonal strain A/Aichi 2/68 (Aichi/68) ($2.5 \times 10^4$ pfu) virus. Following prime and booster vaccinations, strong antibody titers were induced against the homologous virus strains; however no cross-reactive antibodies were detected against heterologous viruses (Table 3).

In one example, the MVA/HA1/C13L/NP vaccine elicited strong HI antibody titers to NW/09 virus but failed to induce any antibody responses to the heterologous strains PR8\, VN/1203 or Aichi/68 viruses (Table 3). Despite the lack of cross-reactivity in HA titers, complete protection against challenge with PR8 or VN/1203 was observed (Table 3). In addition, the MVA/HA1/C13L/NP vaccine conferred partial protection (57.1%) against challenge with Aichi/68 virus (Table 3). In the case of the MVA/HA5/C13L/NP virus, it did not induce any detectable antibody responses to any of the H1N1 viruses (NW/09 and PR8) or H3N2 (Aichi/68) virus. However, it did protect immunized mice against challenge with the H1N1 PR8 strain (Table 3). Analysis of lung viral loads following challenge with the H1N1 pandemic NW/09 strain showed significantly higher ($P<0.05$) virus titers in mice vaccinated with MVA/HA5/C13L/NP or MVA/GFP virus as compared to mice immunized with MVA/HA1/C13L/NP virus (FIG. 24).

Figures 25A, 25B, 25C, 25D:
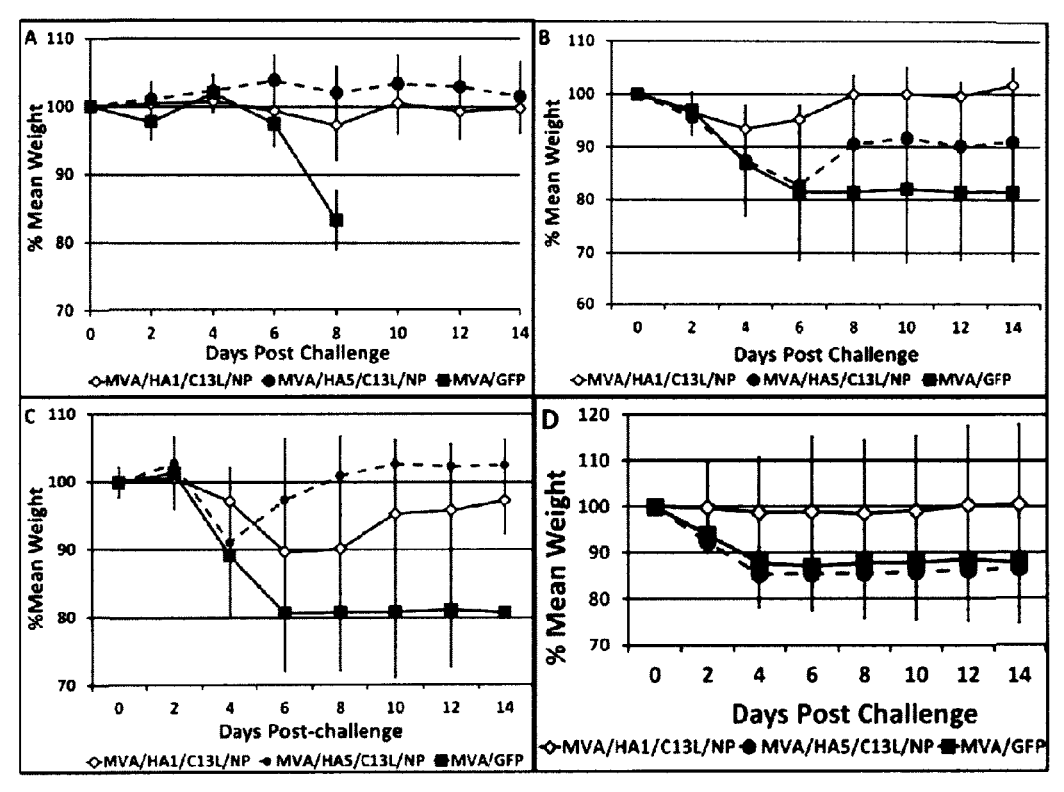

Mice immunized with MVA/HA1/C13L/NP vaccine had no significant weight loss following challenge with the H5N1 VN/1203 strain whereas those immunized with the MVA/HA5/C13L/NP virus had significant weight loss upon challenge with H1N1 pandemic NW/09 strain (FIGS. 25A and 25B). Mice in the control group consistently lost weight upon challenge with VN/1203, NW/09, PR8 or Aichi/68 virus (FIGS. 25A, 25B, 25C and 25D). In conjunction with the cross-protection survival data, mice immunized with MVA/HA5/C13L/NP demonstrated significant weight loss ($P<0.05$) compared to mice immunized with MVA/HA1/C13L/NP upon challenge with the $H_3N_2$ Aichi/68 virus (FIG. 25D); however no significant differences in weight were recorded in mice immunized with MVA/HA1/C13L/NP or MVA/HA5/C13L/NP vaccines following challenge with seasonal H1N1 PR8 virus (FIG. 25C). Taken together, these data indicate that certain constructs can provide broader cross-protective immunity that others, for example, the MVA/HA1/C13L/NP vaccine that conferred complete protection from all three group 1 A strains and partial protection against the group 2 H3N2 strain. Surprisingly, the MVA/HA5/C13L/NP strain completely protected against heterologous challenge with the seasonal H1N1 strain, but not pandemic H1N1 strain, nor the H3N2 strain.

Example 10

Vector Immunity

In another exemplary method, MVA was used to pre-expose a group of mice to an influenza vaccine having proteins from multiple subtypes. In these experiments, pre-exposure of mice to MVA significantly ($P<0.05$) affected the neutralizing antibody titers elicited post-priming with MVA/HA5 vaccine. This effect could be reversed following a booster vaccination with the same virus (FIG. 26A). Moreover, pre-existing immunity to MVA did not have any significant impact on the protective efficacy of the vaccine after prime and booster immunizations (FIG. 26B).

Example 11

Safety of the MVA/Flu Vaccine

In another method, SCID mice were injected intraperitoneally with the MVA/HA5 or MVA/C13L/NP viruses or the control MVA/GFP virus. These mice did not develop any pox lesions or any other signs of morbidity. In contrast, animals that were infected with vaccinia-Wyeth, developed pox lesions on their tails, feet and mouth region, and demonstrated gradual weight loss. By week four, the vaccinia-Wyeth group displayed average weight loss of approximately 11% in addition to ruffled fur, hunched posture and pox lesions (data not shown). Weight losses in the vaccinia-Wyeth group was significantly greater (P<0.0001) than in groups that were infected with MVA/Flu vaccines (FIG. 27).

GeneScript constructs using 5'HA1 ssp/3'HA1 or 5' HA5 ssp/3' HA5, respectively, (Table 3) to generate appropriate restriction sites and their native secretory signals and then sub-cloned into plasmid pdIIIGFP, generating plasmids pdII-IGFP/HA1 and pdIIIGFP/HA5 respectively. An alternative transfer plasmid with a secretory signal, pdIIIGFP/C13L, was generated by inserting a linker, 5'/3' C13L-ssp, (Table 3)

TABLE 3

Cross-protective immunity of MVA/Flu vaccines

| | Challenge virus | | | | | | | |
|---|---|---|---|---|---|---|---|---|
| | H5N1 (VN/1203) | | H1N1pdm (NW/09pdm) | | H1N1 seasonal (PR8) | | H3N2 seasonal (Aichi/68) | |
| Vaccines | Post-Boost Titer (GMT) | % Survival | Post-Boost Titer (GMT) | % Survival | Post-Boost Titer (GMT) | % Survival | Post-Boost Titer (GMT) | % Survival |
| MVA/HA$_1$/C13L/NP | <20[a] | 100 | 373 | 100 | <20 | 100 | <20 | 57.1 |
| MVA/HA$_5$/C13L/NP | 149 | 100 | <20 | 28.6 | <20 | 100 | <20 | 14.3 |
| MVA/GFP | <20 | 0 | <20 | 28.6 | <20 | 14.3 | <20 | 28.6 |

[a]Below limit of detection. Hemagglutination inhibition antibody titers are presented as geometric mean Materials and Methods
Cells and Viruses Mardin-Darby canine kidney (MDCK) cells obtained from the American Type Culture Collection (ATCC, Manassas, Va.) were propagated in Dulbecco's Modified Eagle's Medium (DMEM) supplemented with 10% fetal bovine serum (FBS) and 1% antibiotics. Stocks of chicken embryo fibroblasts (CEF) were produced as previously described. The CEF were used for propagating modified vaccinia Ankara (MVA) virus. Highly pathogenic avian influenza (H5N1) virus (A/Vietnam/1203/04), pandemic H1N1 virus (A/Norway/3487-2/09), seasonal H1N1 virus (A/Puerto Rico/8/34) and H3N2 virus (A/Aichi/2/68) were obtained. The influenza viruses were propagated and titrated by TCID50 in MDCK cells with DMEM that contained 1% bovine serum albumin and 20 mM HEPES and were stored as infectious stocks at −80° C. Viral stock titers were determined by endpoint dilution and recorded as 50% tissue culture infectious dose (TCID50) as previously described. Culture media for H1N1 and H3N2 viruses also included 1 µg/ml of trypsin treated with tosyl phenylalanyl chloromethyl ketone (TPCK). Work with H5N1 influenza virus was conducted in a BSL3+ facility in compliance with the UW Madison Office of Biological Safety.
Construction of Plasmids and Production of MVA Recombinant Vaccines In one exemplary embodiment, transfer plasmid pdIIIGFP encoding green fluorescent protein were used to generate recombinant MVA viruses expressing influenza virus antigens as previously described but other methods can be used. Hemagglutinin (HA1) gene from H1N1pdm (A/California/04/09) and HA5 gene from H5N1 (A/VN1203/04) virus were synthesized after codon optimization for mammalian expression by GeneScript (Piscataway, N.J.). Coding regions of HA1 and HA5 proteins were amplified by PCR from the fused with a secretory signal from vaccinia virus (from the N terminus of the C13L vaccinia gene) at the 5' end of the multiple cloning site (MCS) such that antigens could be inserted in frame with the secretory signal. The entire coding region of nucleoprotein (NP) of H5N1 influenza virus (A/Vietnam/1203/04) was amplified by PCR from cDNA clone and then inserted into plasmid pdIIIGFP/C13L to generate the plasmid pdIIIGFP/C13L/NP. A dual transfer vector pdIIIGFP-d was constructed by inverting the GFP cassette in pdIIIGFP and then inserting a second promoter/MCS cassette in an inverted orientation to the primary promoter cassette (FIG. 21). The coding regions of HA1, HA5 and C13L/NP were sub-cloned from the single expression constructs to generate dual expression constructs pdIIIGFP/HA1/C13L/NP and pdIIIGFP/HA5/C13L/NP, respectively (FIG. 21).

The recombinant MVA/Flu viruses were generated as described previously for each HA and NP constructs. Briefly, CEF cells grown in 35 mm 6-well plates were infected with wild-type MVA at a multiplicity of infection (MOI) of 0.05 pfu/cell for one hour (h) and then transfected with each of the expression plasmids using Lipofectamine™ (Invitrogen, Carlsbad, Calif.). At 48-72 h post-transfection, cell monolayers were harvested, centrifuged at 500×g for 5 min at 4° C. and disrupted by freeze-thaw and sonication (2 times for 15 seconds using a Virtis600 at setting 3). The disrupted cell extracts containing possible recombinant viruses expressing GFP were plated onto fresh CEF and overlaid with 0.8% agarose. After 48-72 h of incubation, recombinant virus-generated plaques were detected by fluorescence using an inverted microscope and picked into media with a glass pipette. The cell/virus samples were sonicated and plated as described above. After three consecutive rounds of plaque purification, high titer virus stocks were prepared in CEF for subsequent in vitro and in vivo characterization.

TABLE 4

Sequence of primers used for amplification of influenza virus proteins

| Primer | PCR Primer Sequence[a] | Restriction Enzyme |
|---|---|---|
| 5' HA$_5$ ssp | 5'-tctcCCCGGGatggagaaaatagtgcttcttttttgcaatagtcagt cttgttaaaagtgatcagatttgcattggttaccat-3' | XmaI (SEQ ID NO: 11) |
| 3' HA$_5$ | 5'-ggcGGATCCttaaatgcaaattctgcattgt-3' | NgomIV (SEQ ID NO: 12) |
| 5'HA$_1$ ssp | 5'-gtgaCCCGGGatgaaggccatcctggtcgtgctgctgtacaccttc gccaccgccaacgccgacacactgtgtatcgggtat-3' | XmaI (SEQ ID NO: 13) |
| 3'HA$_1$ | 5'-gatccGCTAGCtcagatacagat-3' | NheI (SEQ ID NO: 14) |
| 5' NP | 5'-gtgaGCCGGCgcgtctcaaggcaccaaa-3' | NgomIV (SEQ ID NO: 15) |
| 3'NP | 5'-gcGAATTCttaattgtcatactcctctgcattgt-3' | EcoRI (SEQ ID NO: 16) |
| 5' C13L-ssp | 5'-CCGGGatgatgatatacggattaatagcgtgtcttatattcgtgac ttcatccatcgctagtccaGCCGGCG-3' | XmaI, NgomIV, NheI (SEQ ID NO: 17) |
| 3' C13L-ssp | 5'-CTAGCGCCGGCtggactagcgatggatgaagtcacgaatataagac acgctattaatccgtatatcatcatC-3' | XmaI, NgomIV, NheI (SEQ ID NO: 18) |

[a]Restriction enzyme sites are capitalized.

In Vitro Expression of Influenza Virus Antigens

The in vitro expression of HA or NP antigens by recombinant MVA/Flu viruses was determined by immuno-blot analyses. CEF cells were seeded into 6-well plates and then infected with either of the recombinant viruses at a multiplicity of infection (MOI) of 0.5 pfu/cell under serum free conditions. At 48 h post-infection, the infected cells were harvested in the presence of a protease inhibitor cocktail (Mini Protease tabs, Roche Diagnostics, Indianapolis, Ind.), washed, resuspended in IX loading buffer and heated to 95° C. for 5 min. The supernatants from the infected cells were centrifuged and concentrated by ultrafiltration with a 3 kDa cutoff membrane (Nanosep 3K Omega, Pall, Inc., East Hills, N.Y.). The concentrated supernatants were then combined with an equal volume of 2× gel loading buffer and heated to 95° C. for 5 min Supernatant and cell samples were resolved by SDS polyacrylamide gel electrophoresis (SDS-PAGE) and transferred to a nitrocellulose membrane for immuno-blot analysis using anti-H1 (NR-15429, ferret polyclonal), anti-H5 (NR-2730, mouse monoclonal) or anti-NP (NR-4282, mouse monoclonal) antibodies (ATCC, BEI Resources, Manassas, Va.).

Animal Studies

All mouse studies were conducted at University of Wisconsin-Madison animal facilities and were approved by its Interinstitutional Animal Care and Use Committee (IACUC). Challenge experiments involving H5N1 virus (ANietnam/1203/04) were conducted in an ABSL3+ facility in compliance with the University of Wisconsin-Madison Office of Biological Safety.

Vaccine Efficacy

A series of experiments were performed to assess the immunogenicity and protective efficacy of MVA/Flu viruses (MVA/HA1, MVA/HA5, MVA/C13L/NP, MVA/HA1/C13L/NP and MVA/HA5/C13L/NP). Groups (n=10) of five week old BALB/c mice (Harlan, Indianapolis, Ind.) were vaccinated with 1×10$^7$ plaque forming unit (pfu) of recombinant MVA/Flu virus contained in 50 µl of PBS via the intradermal (ID) route. The animals received a single dose or two vaccine doses (28 days apart) and then blood samples were collected 28 and 56 days post-primary vaccination, respectively for serological analysis. At 56 days post-primary vaccination, mice were challenged by intranasal (IN) instillation under isoflurane anesthesia with 100 LD50 of either A/Vietnam/1203/04 (VN/1203) (1×10$^4$ pfu), A/Norway/3487-2/09 (NW/09) (1.0×10$^6$ pfu), A/Puerto Rico/8/34 (PR8) (3.99×10$^5$ pfu) or A/Aichi/2/68 (Aichi/68) (2.5×10$^4$ pfu) virus contained in 50 µl of PBS. At day three post-challenge, three mice from each group were euthanized and lung tissues were collected and homogenized using a mechanical homogenizer (MP Biochemicals, Solon, Ohio). Viral titers in the homogenates were quantified by plaque assay on MDCK cells. Body weight was measured on alternative days and survival rates were recorded daily for 14 days. Mice showing 20% or more of body weight loss were considered to have reached the experimental end point and were humanely euthanized.

Vector Immunity

To assess the effect of pre-existing immunity to the vector virus on MVA/Flu vaccines, groups of 4 week old BALB/c mice (n=7) were first injected ID with MVA/GFP (1×10$^7$ pfu) virus and then vaccinated with the recombinant MVA/FLU vaccine (same route and dose) three months later. Following the initial MVA/GFP inoculation, mice were vaccinated with 2 doses (28 days apart) of either 1×10$^7$ pfu of MVA/HA5 or MVA/GFP virus followed (28 days post-boost) by a challenge with 100 LD50 of VN/1203 virus. Mice were monitored for morbidity and survival rates recorded over 14 days.

Vaccine Safety

Safety of MVA/Flu viruses was evaluated in severe combined immunodeficiency (SCID) BALB/c mice. Briefly, 4-6 week old SCID mice (n=6) were injected intraperitoneally with 1×10$^8$ pfu of the MVA/HA5, MVA/C13L/NP, MVA/GFP virus, or 1×10$^6$ pfu of wild-type (WT) vaccinia virus (Wyeth strain). Mice were monitored for 9 weeks for morbidity including weight loss and appearance of pox lesions.

Serology

Blood samples were collected from all animals via the maxillary vein at different time-points post-vaccination and prior to challenge to determine antibody titers by hemagglutination inhibition (HI) or by microneutralization assays.

Briefly, aliquots of serum samples were treated with receptor destroying enzyme (RDE, Denka Seiken, TKY). One volume of pooled serum was added to three volumes of RDE, incubated at 37° C. for 16 hours, then heat-inactivated at 56° C. for 1 h. Hemagglutination inhibition (HI) assay was conducted by mixing 25 µl of two-fold serial dilutions of sera in with 8 HA units of virus re-suspended in the same volume of PBS and incubated in 96-well plates for 45 min at room temperature (RT). Following this, 50 µl of turkey red blood cells (0.5%) were added and plates were incubated at RT for 45 min. HI titers of sera were determined as the highest dilution that displayed hemagglutinin inhibition activity. For microneutralization assay, 50 µl of serially (two-fold) treated serum samples were added to 50 µl of virus containing 200 TCID50 units and then incubated at 37° C. for 1 hour. The virus-serum mixture from each dilution was added to duplicate wells of MDCK cells in 96-well plates, incubated at 37° C. for 72 hours, fixed and stained with 10% crystal violet in 10% formalin to determine the TCID. The titer was defined as the serum dilution resulting in complete neutralization of the virus.

Statistical Analysis

One way ANOVA was used to evaluate the vaccine group effects on pre-boost and pre-challenge antibody titers. If the vaccine group effect was statistically significant (P<0.05 by Kruskal-Wallis test), an all pair-wise comparison among groups was performed using an unadjusted P-value of 0.05. Survival analyses were performed to assess vaccine effectiveness against challenge viruses; reported P-values are from Fisher's exact test. Probability values<0.05 were considered significant using the GraphPad Prism 5 software (La Jolla, Calif.) for all statistical analyses.

FIG. 21: Represents a schematic of a recombinant plasmid construction. Expression cassettes were generated by PCR for each of the influenza virus hemagglutinin antigens, HA1 and HA5 as described in the materials and methods. The cassettes were cloned into the pdIIIGFP vector and the resulting plasmids were designated as pdIIIGFP/HA1 and pdII-IGFP/HA5. The coding regions of HA1, HA5 and C13L/NP were sub-cloned from the single expression constructs to generate dual expression constructs pdIIIGFP/HA1/C13L/NP and pdIIIGFP/HA5/C13L/NP. Homologous recombination into MVA was successfully completed and recombinant MVA/Flu viruses were identified by GFP expression. HA, NP and C13L are represented with orange, green and pink color codings. MCS1 and MCS2-multiple cloning sites; Flanks1 and Flanks2-open box, GFP-striped box; dSP-orthopoxvirus secretory signals, either p11 (gfp) or synthetic early/late promoter (MCS1/2) and delIII-MVA deletion region III.

FIG. 22 illustrates expression of influenza virus proteins by recombinant MVA/flu viruses in infected cells. Monolayers of CEF cells were infected with exemplary recombinant MVA/flu constructs including, MVA/C13L/NP, MVA/HA1, MVA/HA5, MVA/HA1/C13L/NP or MVA/HA5/C13L/NP virus at MOI of 0.05 pfu/cell. At 48 h post-infection cells were harvested and subjected to SDS-PAGE followed by Western blot analysis. (A) HA expression in CEF cell (c) and supernatant (s) fractions detected with anti-H1 antibody in (Ai) MVA/HA1 and (Aii) MVA/HA1/C13L/NP. (B) HA expression in CEF cell (c) and supernatant (s) fractions detected with anti-H5 antibody in (Bi) MVA/HA5 and (Bii) MVA/HA5/C13L/NP. 50 ng of HA5 protein was loaded as a positive control for size (C) NP expression in CEF cell (c) and supernatant (s) fractions detected with anti-NP antibody in MVA/NP and MVA/C13L/NP. M indicates molecular weight markers.

FIG. 23 represents an example of efficacy of MVA/Flu vaccine against homologous challenge: Mice were immunized with the (n=10) were challenged against pandemic H1N1 (NW/09) (A, C, E, G) or H5N1 (VN/1203) (B, D, F, H). Fifty-six days following primary immunization antibody titers were determined by HI assay (A, B). Mice were challenged 56 days post primary immunization and survival rates were recorded (C, D). Three days post-challenge lung viral load were determined (E, F) and clinical scores (weight) measured over 14 days post-challenge (G, H).

FIG. 24 represents an example of lung viral titers in vaccinated and control animals following challenge with NW/09pdm: Mice (n=3) immunized with two doses (28 days apart) of MVA/HA1/C13L/NP or MVA/HA5/C13L/NP vaccine were challenged with A/H1N1pdm (NW/09) virus 28 days post-boost. Three days post-challenge lungs from mice were harvested and analyzed for viral load by plaque assay. Data points represent antibody titers per gram of tissue (PFU/g) in individual mice. Horizontal bars indicate the mean.

FIG. 25 represents and example of cross protective efficacy of MVA/Flu vaccines: Mean weight of immunized mice (n=7) following challenge with A (VN/1203), B (NW/09), C (PR8) or D (Aichi/68).

FIG. 26 represents an example of effects of vector immunity on vaccine efficacy: Cohorts of mice (n=7) were first injected with MVA vector and then received two doses of MVA/Flu vaccine three months later. Following prime and booster vaccinations, antibody titers were measured by microneutralization (A) and twenty eight days following the booster vaccination, mice were challenged with VN/1203 and survival rates were recorded (B).

FIG. 27 represents an example of safety of MVA-vectored vaccines in SCID mice: Following inoculation of mice (n=6) with MVA/Flu vaccine (1×108 pfu) or with Wyeth strain of vaccinia virus (1×106 pfu), mice were monitored 9 weeks for (A) ruffleness, hunched posture, pox lesions and (B) for weight loss. Mean body weights are presented.

FIG. 28 illustrates an exemplary plasmid construct of some embodiments disclosed herein. FIG. 29 illustrates a histogram plot of cross-protective activity using certain constructs described herein.

\* \* \*

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations may be applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A construct comprising:
   a modified vaccinia virus construct encoding at least one vaccinia virus secretory signal sequence associated with a first influenza protein, and at least a second influenza protein;
   wherein the at least one vaccinia virus secretory signal sequence comprises, at least one of a secretory signal sequence of C13L or B8R;
   wherein the influenza proteins in the construct are capable of inducing an immune response in a subject.

2. The construct of claim 1, wherein the first or second influenza protein comprises hemagglutinin (HA), neuraminidase (NA), nucleoprotein (NP), or matrix (M) or a combination thereof.

3. The construct of claim 1, wherein the vaccinia virus secretory signal sequence is fused to the influenza protein.

4. The construct of claim 1, further comprising one or more translational control sequences.

5. The construct of claim 1, wherein the vaccinia virus is a modified vaccinia Ankara (MVA) virus.

6. The construct of claim 1, wherein at least one of the influenza proteins comprises a naturally-occurring influenza protein with a naturally-occurring influenza secretory signal sequence.

7. The construct of claim 1, wherein the influenza proteins are from different influenza subtypes or different influenza strains.

8. The construct of claim 1, wherein at least one influenza protein is from an influenza A, B or C virus.

9. The construct of claim 1, wherein the first influenza protein comprises the influenza protein nucleoprotein (NP); and the second influenza protein comprise the influenza protein hemagglutinin (HA).

10. A pharmaceutical composition comprising the construct of claim 1; and a pharmaceutically acceptable excipient.

11. The pharmaceutical composition of claim 10, further comprising one or more additional poxvirus constructs having non-poxvirus antigens or fragments thereof.

12. A method for inducing an immune response to an influenza virus in a subject comprising:
   administering the pharmaceutical composition of claim 10 to the subject in an amount sufficient to induce an immune response.

13. The method of claim 12, wherein at least one of the influenza proteins comprises hemagglutinin (HA), neuraminidase (NA), nucleoprotein (NP), or matrix (M).

14. The method of claim 12, wherein at least one influenza protein is obtained from an influenza A, B or C virus.

15. The method of claim 12, further comprising administering a second composition comprising:
   one or more poxvirus constructs prior to or at the same time as administering the pharmaceutical composition of claim 10 to the subject, wherein the second composition is also capable of inducing an immune response in the subject.

16. The method of claim 15, wherein the pharmaceutical composition is administered to the subject 6 months or less prior to the second composition.

17. The method of claim 12, wherein administration of the pharmaceutical composition comprises administering the composition intradermally, subcutaneously, intravenously, orally, intranasally, or by inhalation.

18. A vaccine kit comprising;
   the pharmaceutical compositions of claim 10; and
   at least one container.

* * * * *

UNITED STATES PATENT AND TRADEMARK OFFICE
CERTIFICATE OF CORRECTION

PATENT NO.        : 9,005,632 B2                              Page 1 of 1
APPLICATION NO.   : 13/555026
DATED             : April 14, 2015
INVENTOR(S)       : Dan T. Stinchcomb et al.

It is certified that error appears in the above-identified patent and that said Letters Patent is hereby corrected as shown below:

In the Specification

Col. 1, lines 20-24 under FEDERALLY FUNDED RESEARCH should read:

"This invention was made with Government support under R43 AI061940 and R41 AI074308 awarded by the National Institutes of Health. The Government has certain rights in this invention."

Signed and Sealed this
Eighteenth Day of August, 2015

Michelle K. Lee
*Director of the United States Patent and Trademark Office*